(12) United States Patent
Dietz

(10) Patent No.: US 11,311,738 B2
(45) Date of Patent: Apr. 26, 2022

(54) DEVICES AND METHODS FOR STIMULATING THE IMMUNE SYSTEM TO TREAT DAMAGED OR ABNORMAL TISSUE USING COMPRESSED STATIC MAGNETIC FIELDS

(71) Applicant: Dan Dietz, Richmond, TX (US)

(72) Inventor: Dan Dietz, Richmond, TX (US)

( * ) Notice: Subject to any disclaimer, the term of this patent is extended or adjusted under 35 U.S.C. 154(b) by 0 days.

(21) Appl. No.: 17/174,980

(22) Filed: Feb. 12, 2021

(65) Prior Publication Data
US 2021/0283411 A1    Sep. 16, 2021

Related U.S. Application Data

(60) Provisional application No. 62/989,022, filed on Mar. 13, 2020.

(51) Int. Cl.
*A61N 2/00* (2006.01)
*A61N 2/06* (2006.01)

(52) U.S. Cl.
CPC ............... *A61N 2/004* (2013.01); *A61N 2/06* (2013.01)

(58) Field of Classification Search
CPC . A61N 2/02; A61N 2/008; A61N 1/40; A61N 2/006; A61N 2/002; A61N 2/06; A61N 2/00
See application file for complete search history.

(56) References Cited

U.S. PATENT DOCUMENTS

| | | | | |
|---|---|---|---|---|
| 4,556,051 A | * | 12/1985 | Maurer ..................... | A61N 2/02 600/14 |
| 5,782,743 A | * | 7/1998 | Russell ..................... | A61N 2/06 600/15 |
| 8,137,257 B1 | * | 3/2012 | Berdut Teruel ........ | A61N 2/004 600/9 |

* cited by examiner

*Primary Examiner* — Christine H Matthews
*Assistant Examiner* — Joshua Daryl D Lannu
(74) *Attorney, Agent, or Firm* — WPAT, PC

(57) ABSTRACT

The devices and methods of stimulating the immune system to treat damaged and abnormal tissue using compressed static magnetic fields provides for noninvasive treatment of damages tissue and removal of abnormal tissue. At least two magnets are positioned to have their static magnetic fields compressed at the damaged or abnormal tissue and at the immediately surrounding healthy tissue. The compressed static magnetic fields stimulate the immune system in the immediately surrounding healthy tissue which treats the damaged or abnormal tissue. The treated tissue fully regenerates without additional medical intervention. The devices provide for efficient exposure to compressed magnetic fields and ease of use at different locations on a body and different types of animal species.

3 Claims, 83 Drawing Sheets

Alzheimer's Brain

Face

Side

Back

DEVICES AND METHODS FOR STIMULATING THE IMMUNE SYSTEM TO TREAT DAMAGED OR ABNORMAL TISSUE USING COMPRESSED STATIC MAGNETIC FIELDS

BACKGROUND

1. Field

The disclosure of the present patent application relates to stimulating the immune system to repair damaged or abnormal tissue. Specifically, the present disclosure is directed at applying compressed magnetic fields to the tissue surrounding damaged or abnormal tissue which stimulates the immune system in the healthy tissue for repairing the damaged or abnormal tissue.

2. Description of the Related Art

Malignant tumors are presently treated by a variety of different methods, including, but not limited to, chemotherapy, radiation therapy, surgery, immunotherapy and laser therapy. Although proven to be effective, each of these methods is typically seen to be undesirable for the patient due to the inherent risks of the treatment itself as well as the various negative side effects associated with each treatment. Each of these methods is also costly, time consuming and requires highly specialized equipment and medical practitioners.

The use of non-ionizing magnetic fields to treat tumors has shown promise in a number of in vitro and animal studies. Such treatment is not painful, relies only on conventional magnets or electromagnets and, unlike chemotherapy and ionizing radiation treatments, does not also harm normal tissues. Similarly, blocking tumor blood vessel growth, and the associated starving of tumors of their blood supply, is of great interest for tumor treatment due to the lack of damage to healthy tissue and general absence of pain and side effects for the patient. It would obviously be desirable to be able to effectively treat tumors using non-invasive and easily administered magnetic techniques. Thus, a method of treating tumors and causing full regrowth and regeneration of tissue solving the aforementioned problems is desired.

SUMMARY

The devices and methods of stimulating the immune system to treat damaged and abnormal tissue using compressed static magnetic fields provides for noninvasive treatment of damaged tissue, removal of abnormal tissue, and regrowth of the tissue. At least two magnets may be positioned to have their magnetic fields intersect at the damaged or abnormal tissue and the immediately surrounding healthy tissue. The compressed magnetic fields stimulate the immune system in the immediately surrounding healthy tissue which treats the damaged or abnormal tissue. The treated tissue fully regenerates without additional medical intervention. The devices provide for efficient exposure to compressed magnetic fields and ease of use for different locations on a human body, as well as multiple animal species.

These and other features of the present subject matter will become readily apparent upon further review of the following specification.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1A:
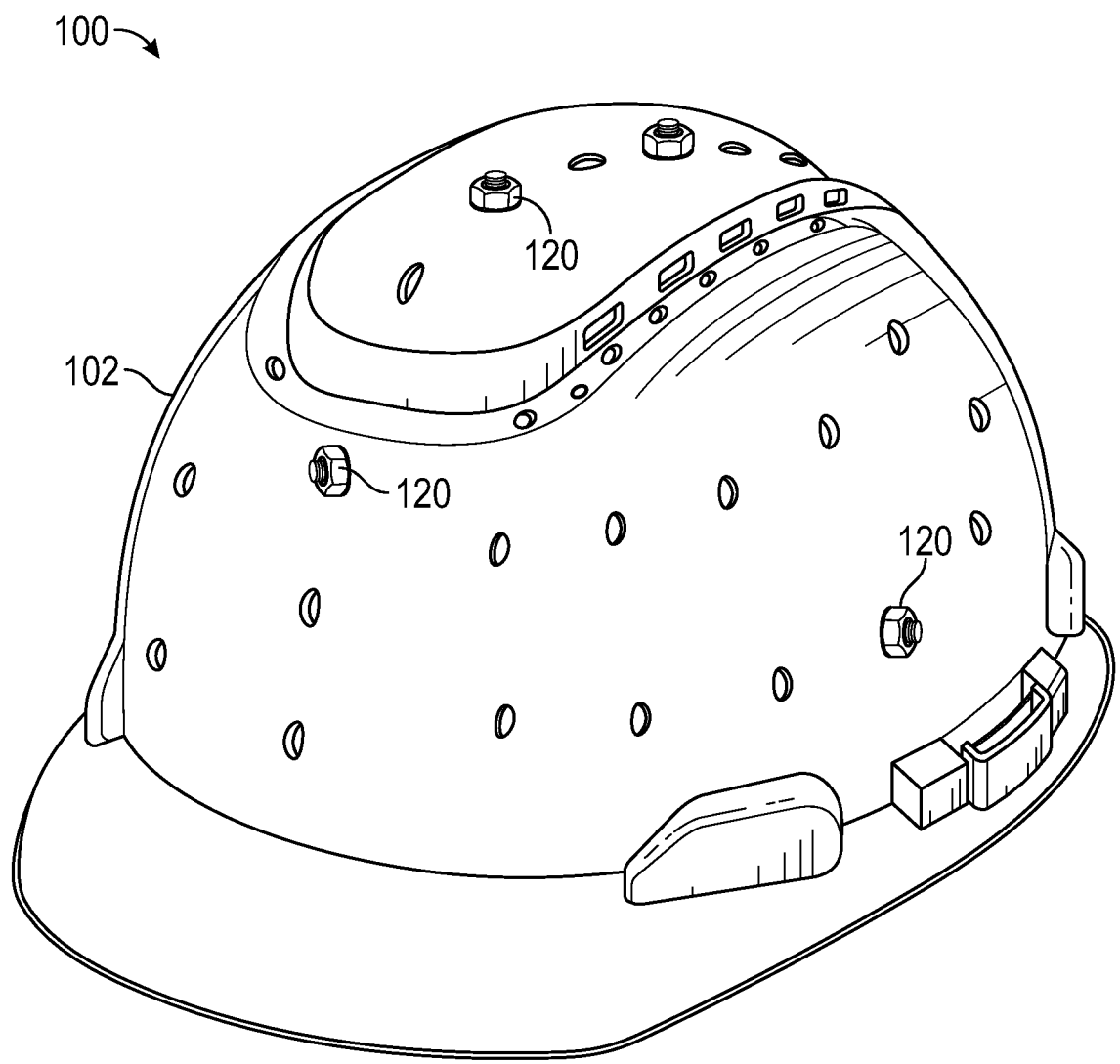
FIG. 1A is a perspective view of a magnetic therapy helmet.

The method of stimulating the immune system to treat damaged or abnormal tissue involves providing compressed, static magnetic fields, from static magnetics, in the area immediately surrounding the damaged or abnormal tissue, and on the damaged or abnormal tissue ("treatment tissue"). By compressing the static magnetic fields, a condensed, static magnetic field is formed in the area of the compressed fields. A condensed, static magnetic field interacts with the electrical charges and/or currents present in the healthy tissue surrounding the treatment tissue, which stimulates the patient's immune system in the healthy tissue. For example, the condensed, static magnetic field may draw electrical current to the targeted health tissue which in turn stimulates the immune response of the healthy tissue. The stimulated immune response from the healthy tissue located adjacent the treatment tissue will act on the treatment tissue to remove abnormal tissue, as well as provide tissue repair and regeneration. In many scenarios, the interaction between the compressed static magnetic field and the tissue will provide an increased presence of stem cells.

Any embodiment of the device and methods for stimulating the immune system to treat damaged or abnormal tissue using compressed static magnetic fields may use mounting magnets to produce the static magnetic fields. A mounting magnet is static magnet surrounded by a spacer (typically a polymer) and a steel (or other non-magnetically charged magnetic materials) cup. The steel cup extends over one pole ("weak pole") of the magnet to direct the magnetic field towards the opposing pole ("strong pole"), thus resulting in a more powerful static magnetic field extending out from strong pole of the magnet. Accordingly, in some embodiments, the strong pole of the magnets will be directed at the treatment tissue, which will also encompass the healthy tissue immediately surrounding the treatment tissue. Any discussion of directing magnetic fields in the below description is referring to pointing the strong pole of a mounting magnet in that direction. In some embodiments, the magnets may be oriented so the compressed magnetic fields are all north pole magnetic fields, all south pole magnetic fields, or a combination of the two. In some non-limiting embodiments, the magnets may have a width and length in the range of 1 to 10 inches, a thickness in the range of 0.25 to 2 inches, a central opening in the range of 0.25 to 2 inches, and/or a grade in the range of N42 to N55. Magnets with higher grades may be used when they become available.

The strength of the static magnetic field at the treatment tissue and immediately surrounding treatment tissue is related to the distance between the magnet and the target tissue. Accordingly, the magnets may be secured at locations that provide the shortest distance between the magnet and the treatment tissue, which will provide the strongest magnetic field to the healthy tissue immediately surrounding the treatment tissue. The following Figures depict non-limiting embodiments of magnetic therapy devices which may be used to provide compressed, static magnetic fields (condensed magnetic fields) in treatment tissue and the healthy tissue immediate surrounding the treatment tissue for different treatment sites on multiple types of patients (humans, dogs, or any other mammal).

Figure 1B:
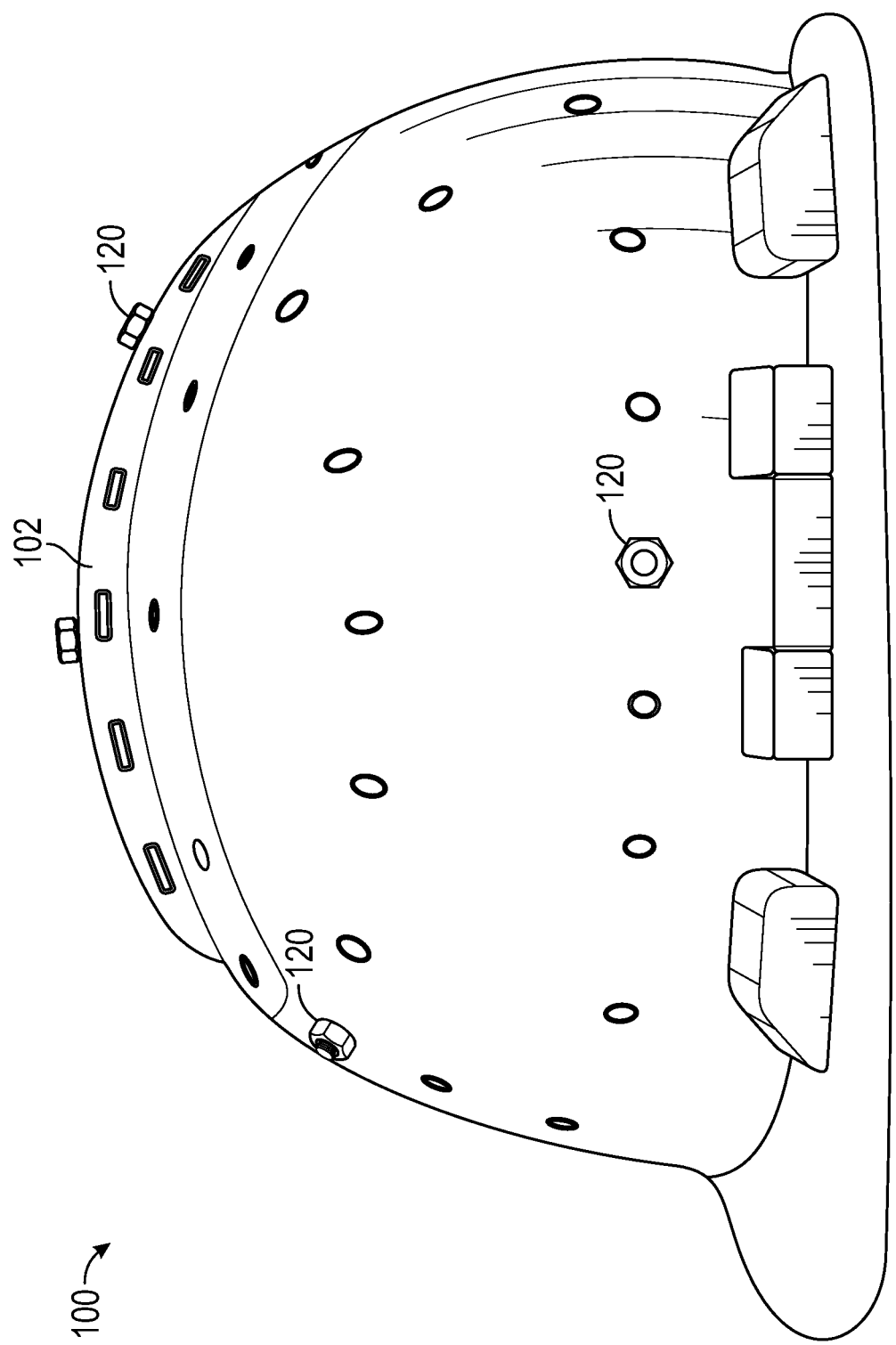
FIG. 1B is side view of the magnetic therapy helmet of FIG. 1.
Figure 1C:
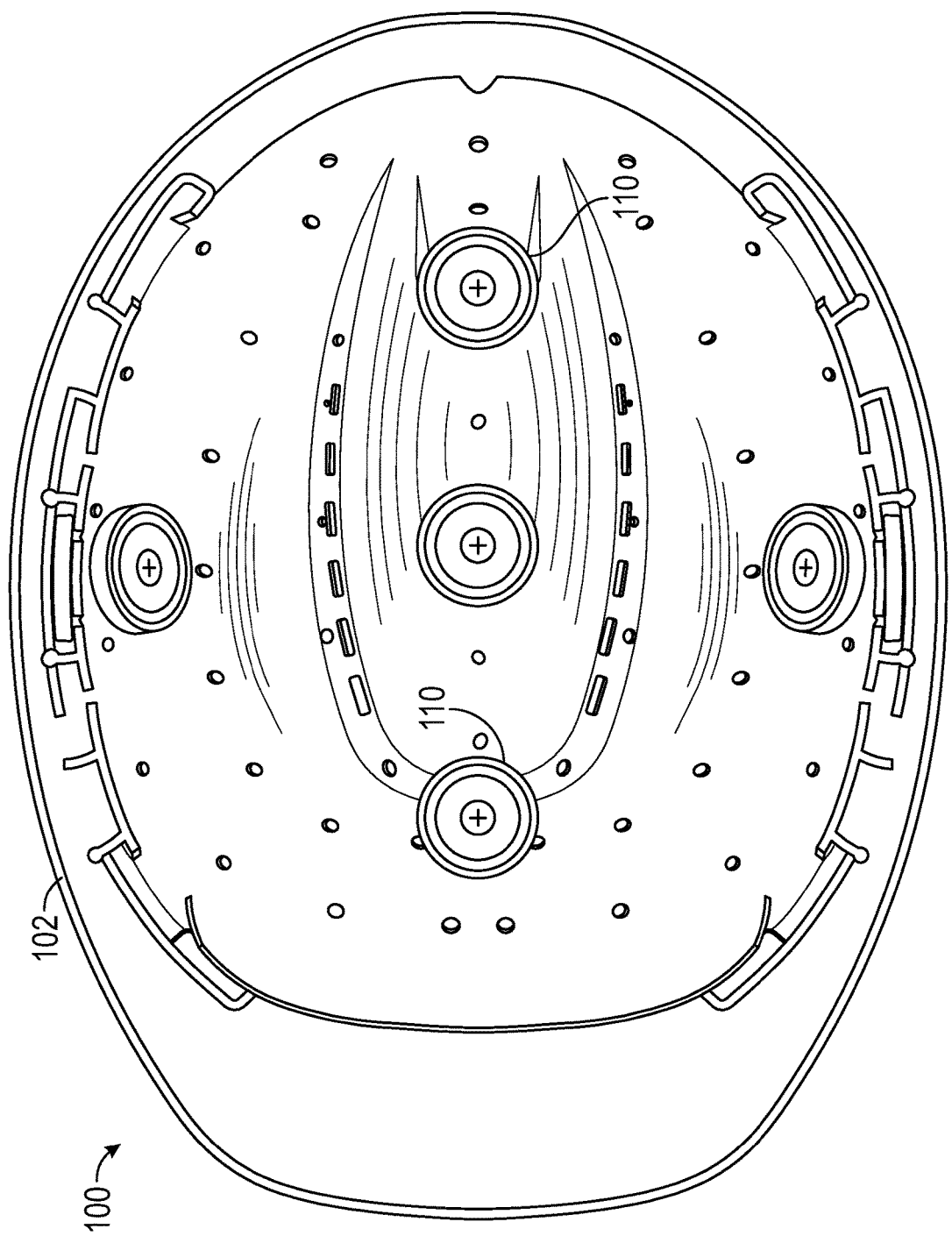
FIG. 1C is a bottom view of the magnetic therapy helmet of FIG. 1.
Figure 2:
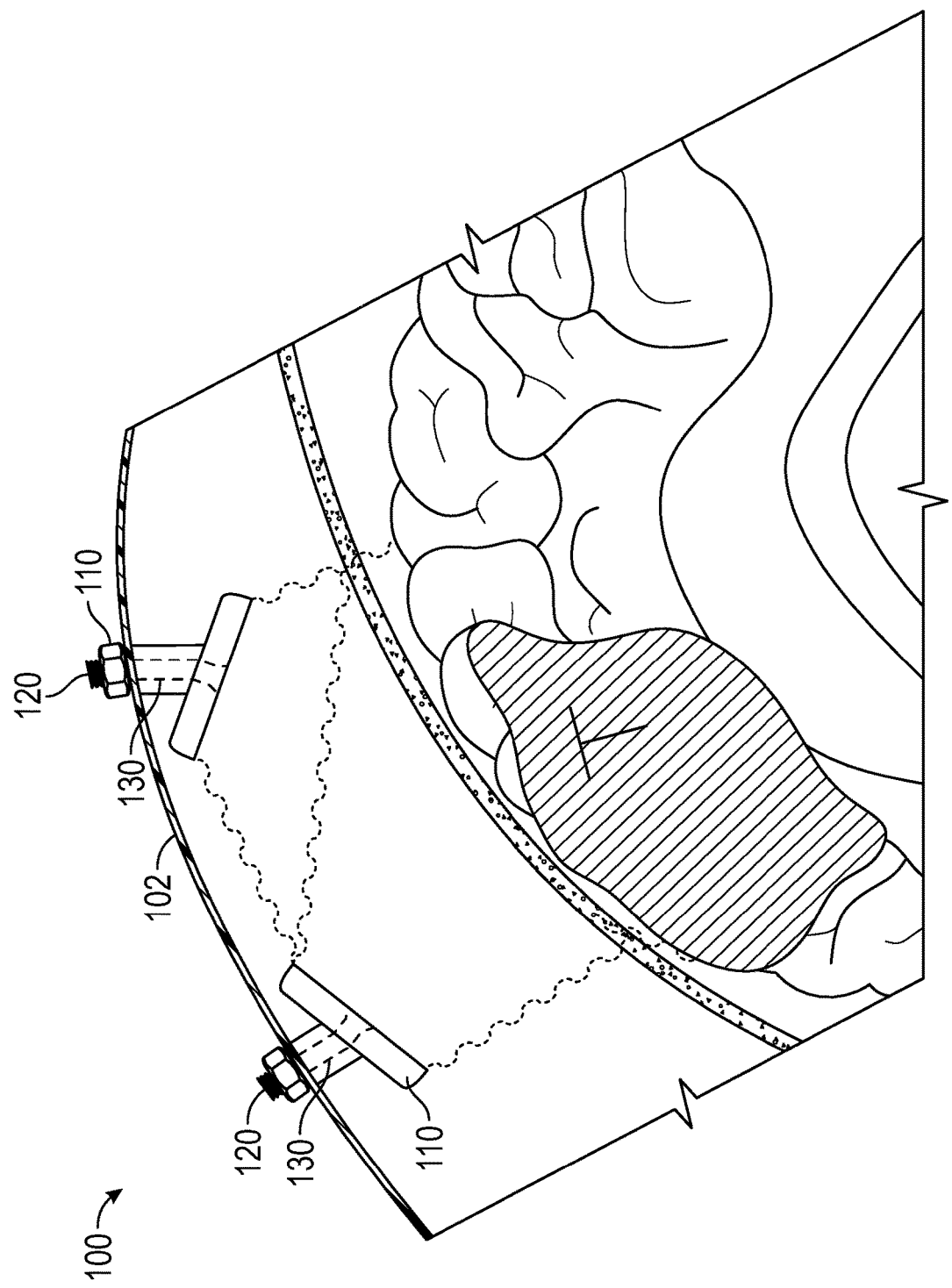
FIG. 2 is a sectioned view of the magnetic therapy helmet of FIG. 1 when on a user's head, showing the magnetic fields produced by the magnets of the helmet.
Figure 3:
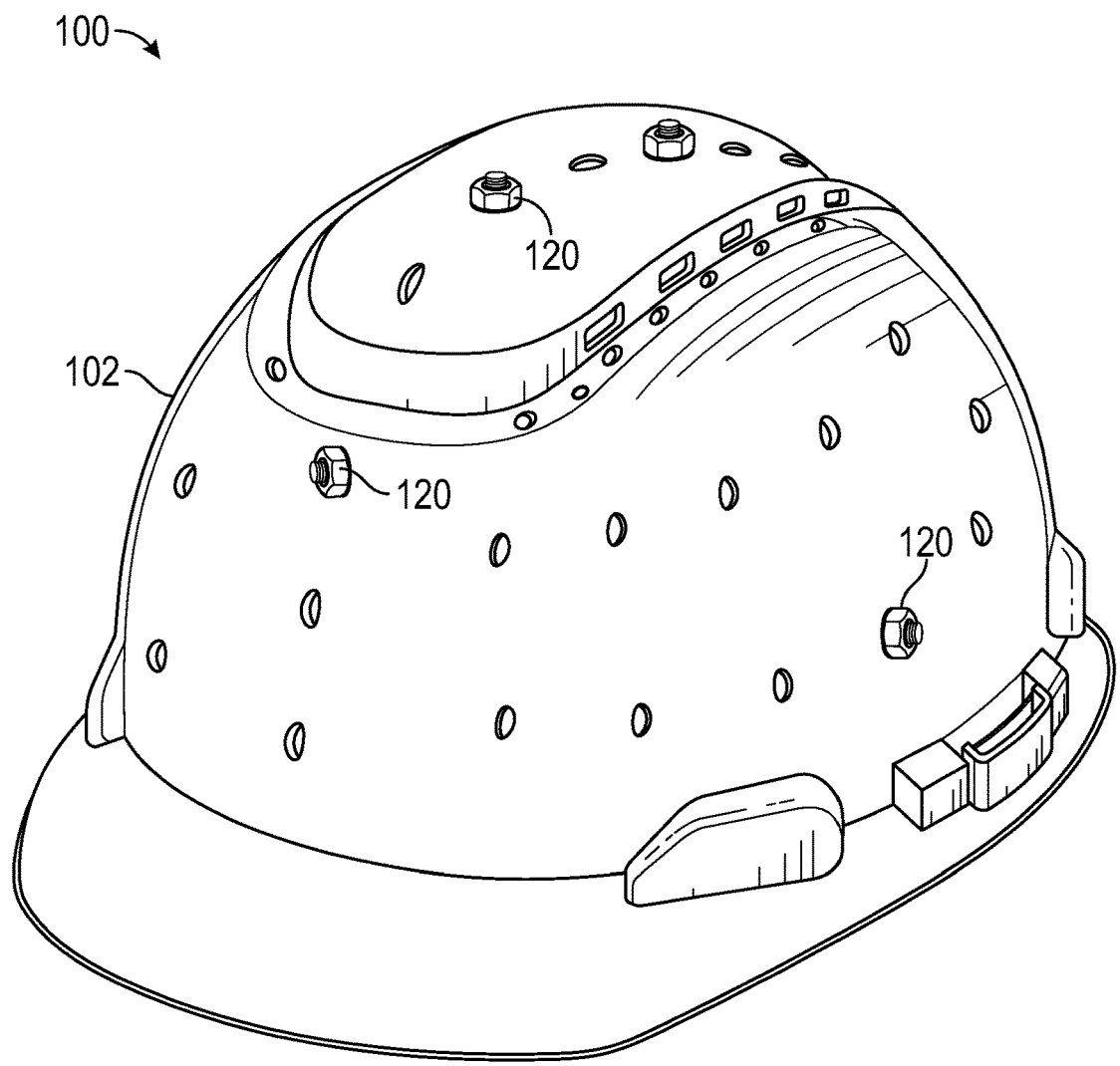
FIG. 3 is a perspective view of magnetic therapy system including the magnetic therapy helmet of FIG. 1A and a magnetic therapy mouth guard.
Figure 3:
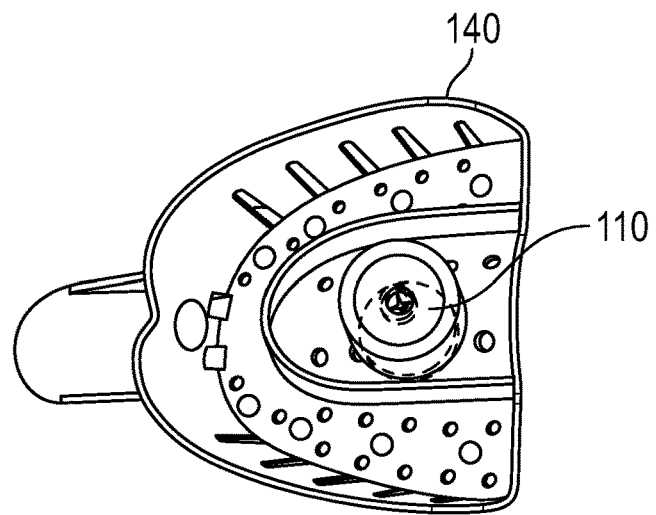

FIGS. 1A-1C depict an embodiment of a magnetic therapy helmet 100 for providing compressed static magnetic fields to a head of a user. The helmet 100 may be any device that provides a rigid body for supporting magnets around a patients head. For example, in some non-limiting embodiments, the helmet 100 may be hard hat, as seen in FIG. 1-3, a hockey helmet, a football helmet, or a bicycle helmet. Static magnets 110 may be attached to the inside of the helmet by a nut and bolt connection 120, as seen in FIGS. 1-4, or any connection known in the art. In some embodiment, the connections 120 may be removable to allow a user to adjust the location of the magnets based on the needs of a patient. Each of the magnets 110 may be directed inwards towards the area a head would reside within the helmet 100.

The non-limiting magnet 110 locations shown in FIG. 1C may be used for treating a damaged or abnormal tissue, such as a tumor (T), on the left side of a patient's brain. Each magnet 110 may be connected perpendicular to the curvature of the helmet body 102 at its location of attachment, to provide compressed, static magnetic fields in the left side of a patient's brain when the helmet 100 is being worn. As previously discussed, if the exact location of the treatment tissue is known, the magnets 110 can be moved to locations that provide maximum strength compressed, static magnetic fields at the healthy tissue immediately surrounding the treatment tissue, as well as on the treatment tissue. For example, the magnets 110 can be connected to the multiple holes defined in the hard hat, or new holes may be created for custom attachment.

Figure 4:
FIG. 4 is an environmental view of the magnetic therapy system of FIG. 3 being worn by a user.

FIG. 2 depicts a magnetic therapy helmet 100 configuration similar to the embodiments of FIGS. 1-3 with the magnets 100 on pivotable bushings 130 for directing the static magnetic fields. One or more of the magnets 100 may be attached to a bushing 130 at an angular offset. As a result, rotating the bushing 130 will change the direction of the static magnetic field. As seen in FIG. 4, two or more magnets 110 may be strategically pointed so their magnetic fields are compressed at the healthy tissue immediately surrounding the treatment tissue and on the treatment tissue, which in the case of FIG. 4 is a tumor (T). Other methods known in the art may be used for pivoting the magnets 110 to adjust the direction of their magnetic field such as a ball joint or a dial axis hinge joint.

FIGS. 3-4 shows a magnetic therapy system including a magnetic therapy helmet 100 and a magnetic therapy mouth guard 140. The helmet 100 may produce static magnetic fields directed horizontally inwards and downwards. To provide an additional compressed magnetic field, a mouth guard 140 having a magnet 110 directed upwards may be worn by a user. In some embodiments, the magnet 110 on the mouth guard 140 may be pivotable for directing the magnetic field towards the exact location of the treatment tissue. For example, as shown in FIG. 1B, the mouth guard magnet 100 may be connected to the mouth guard body 142 by a ball joint 144. In alternate embodiments, the magnet 110 may be connected to the mouth guard body 142 by any pivotable connector known in the art. FIG. 4 shows a user be treated with the helmet 100 being worn on a top of the head and the mouth guard 140 being inserted into the mouth with the magnet facing upwards.

Figure 5:
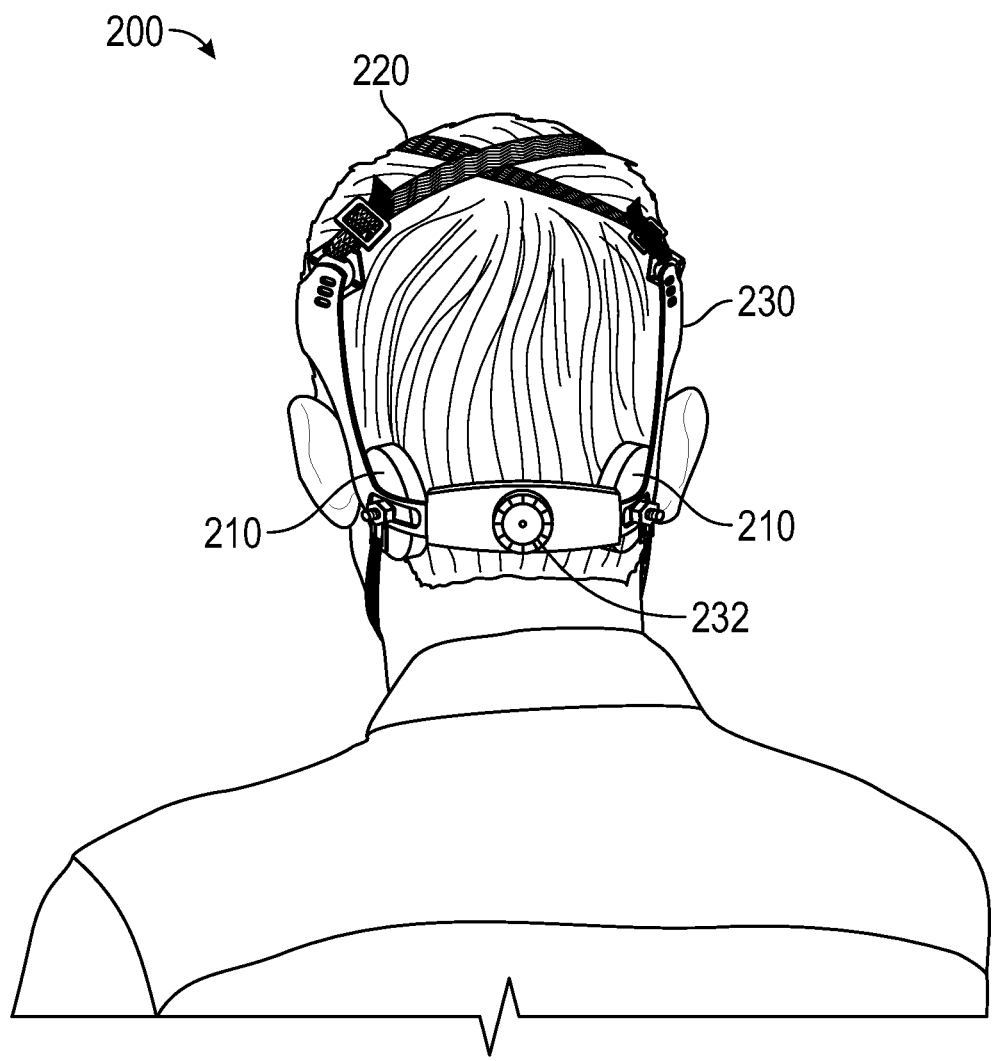
FIG. 5 is an environmental view of a magnetic therapy head harness being worn by a user.
Figure 6:
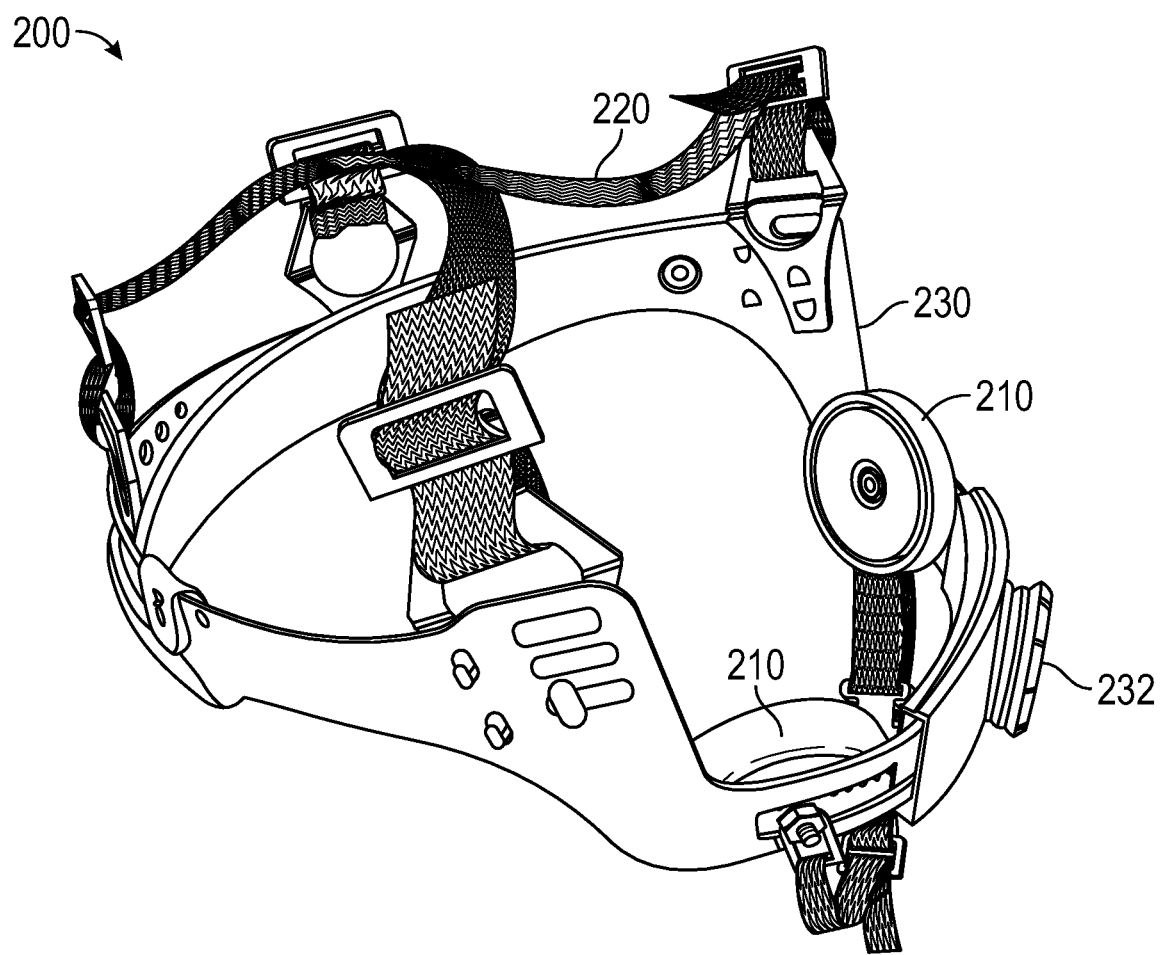
FIG. 6 is a perspective view of the magnetic therapy head harness of FIG. 5.
Figure 7:
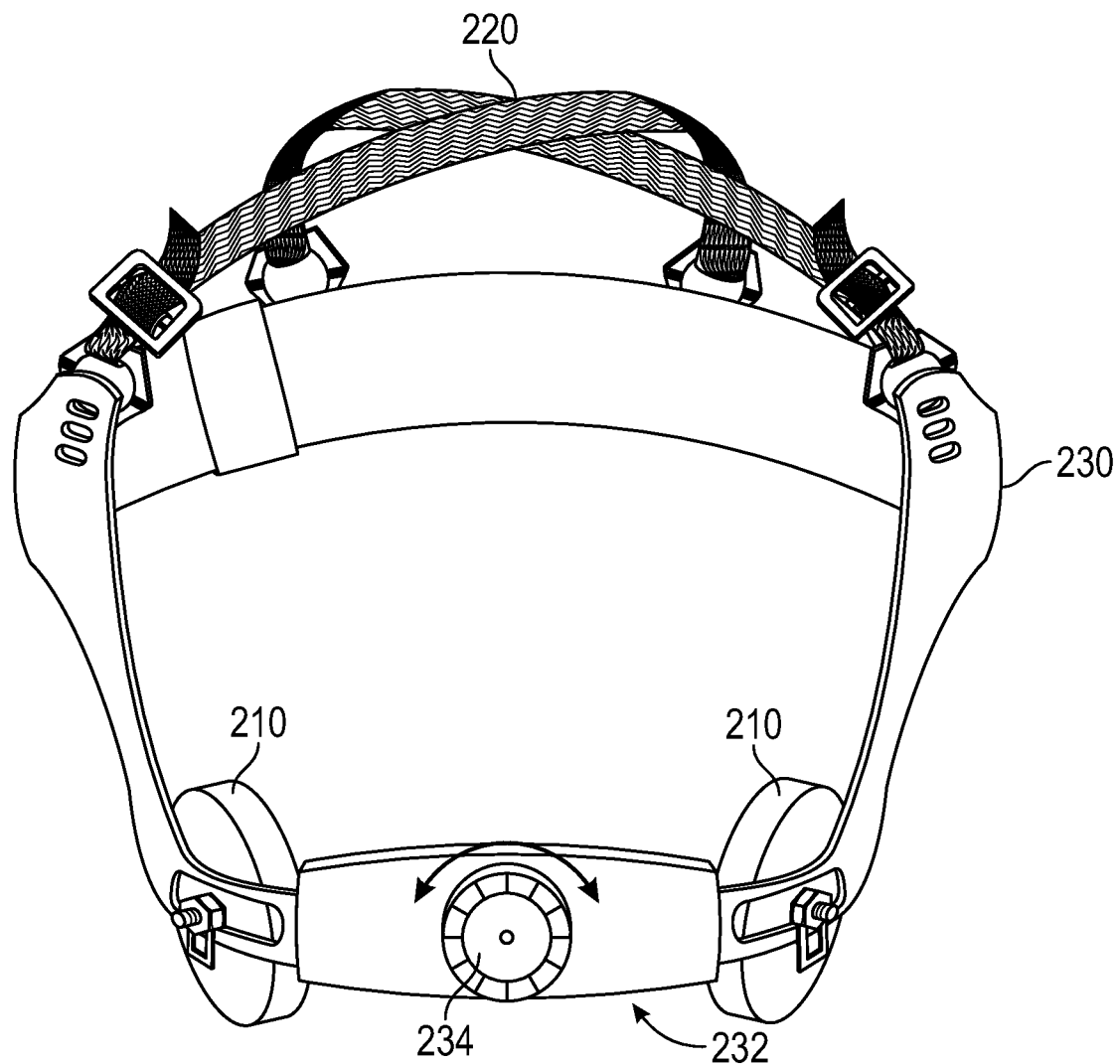
FIG. 7 is a rear view of the magnetic therapy head harness of FIG. 5.
Figure 8:
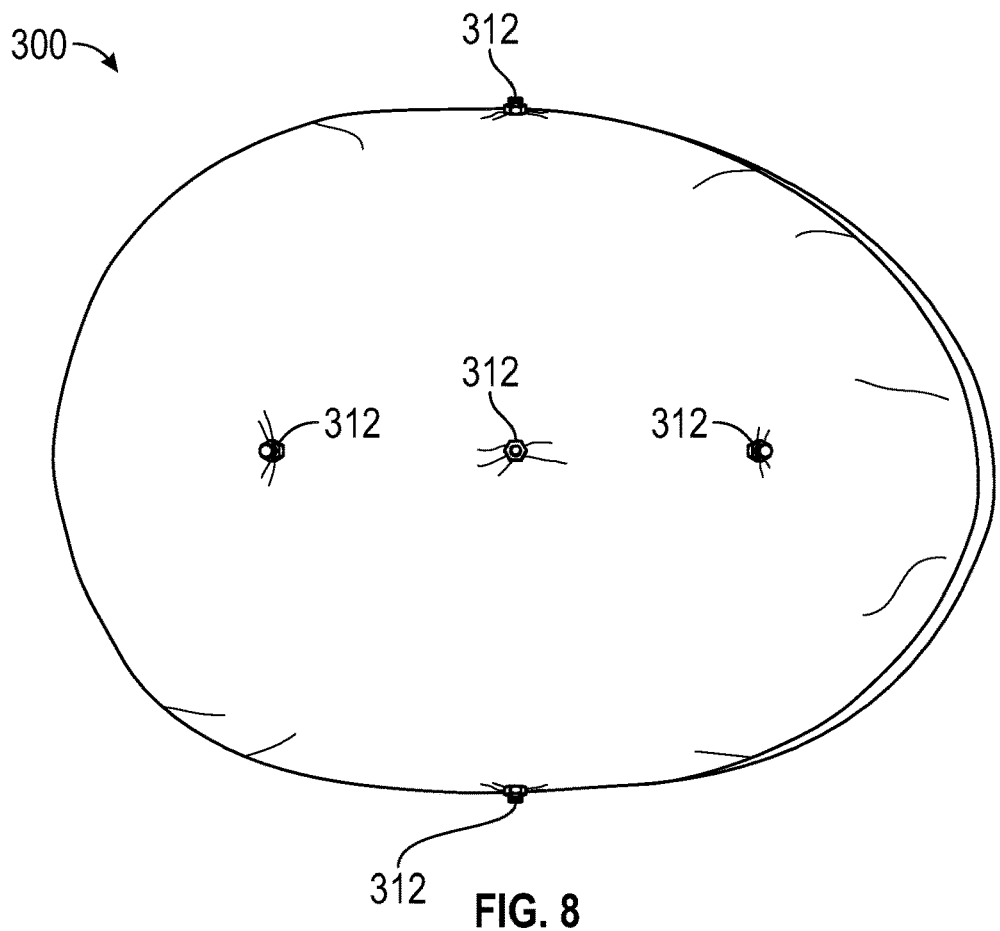
FIG. 8 is a top view of a magnetic therapy hat.
Figure 9:
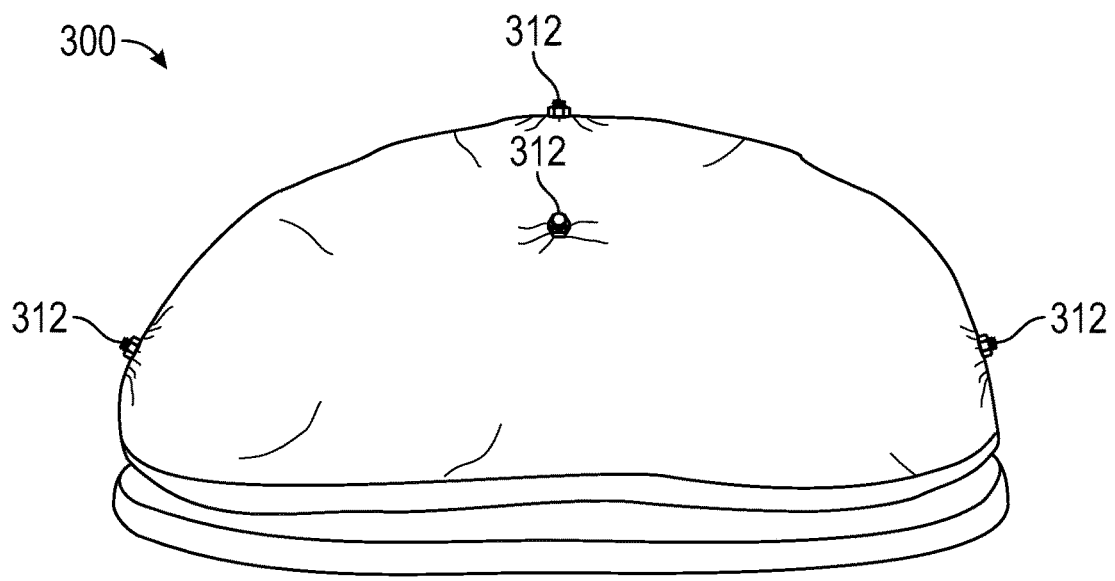
FIGS. 9-10 are opposing side views of the magnetic therapy hat of FIG. 8.
Figure 10:
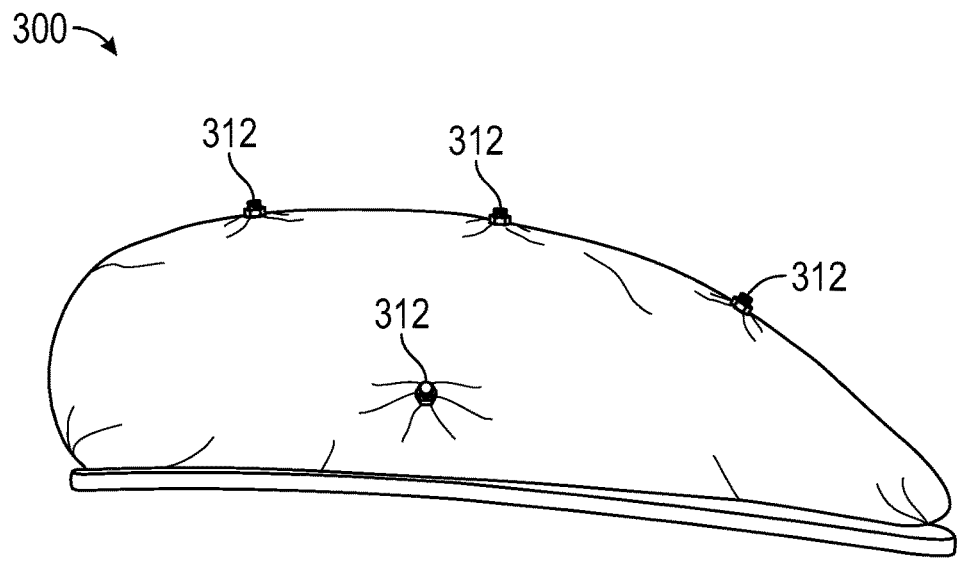
Figure 11:
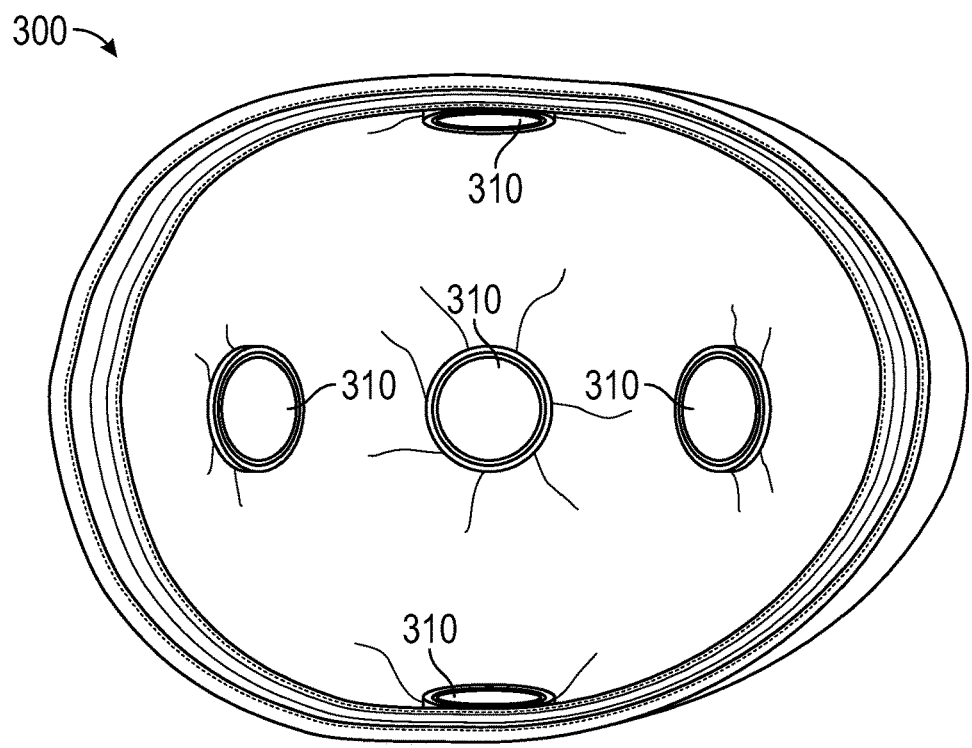
FIG. 11 is a bottom view of the magnetic therapy hat of FIG. 8.
Figure 12:
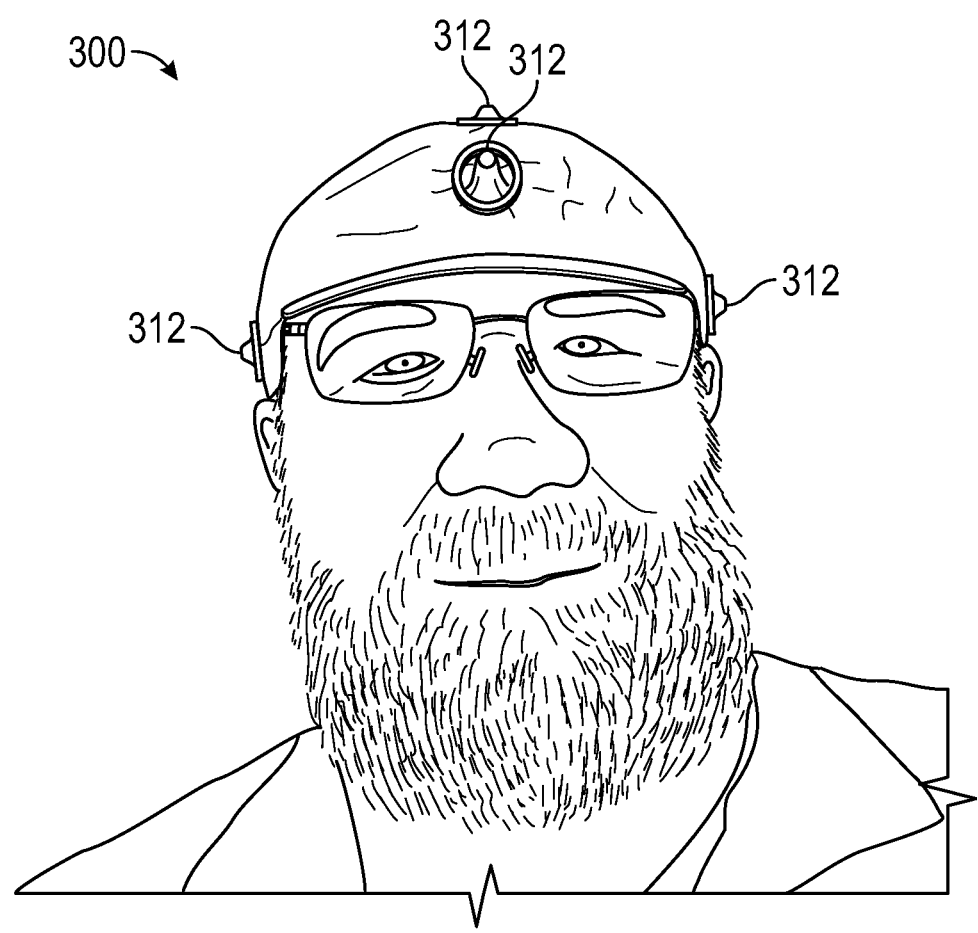
FIG. 12 is an environmental view of the magnetic therapy hat of FIG. 8 being worn by a user.

FIGS. 5-7 depict a magnetic head harness 200 for holding magnets 210 at a base of a patient's brain. The harness 200 may include a rigid body 230 with flexible upper support straps 220. The rigid body 230 may include an adjustment mechanism 232 for accommodating different sized heads. For example, as seen in FIG. 7, a dial 234 may be rotated to increase and decrease the circumference of the body 230.

The straps 220 may also be adjustable for properly positioning a height of the magnets 210. The magnets 210 may be attached to the rear portion of the rigid body 220 and oriented with the strong pole facing inwards (towards the head).

The head harness 200 shown in FIGS. 5-7 may be used to treat abnormal or damaged tissue in the cerebellum or brain stem. An example of a disease treated by the head harness may be ataxia, which is degeneration of the cerebellum. In other embodiments, magnets 210 may be attached to any location of the rigid body 230 based on the location of the treatment tissue. The magnets 210 may be positioned so the treatment tissue is being exposed to a maximum strength compressed magnetic field though approximating the magnets 210 to the treatment tissue and adjusting the direction at which the strong pole of the magnetic 210 is directed. In some embodiments, the magnets may be 3 inches in diameter.

FIGS. 8-15 depict a magnetic hat 300 which may be used to provide static magnetic fields that compress within a head of a user. In the embodiment shown in FIGS. 8-13, the hat 300 may include five magnets 310, one magnet 310 for positioning directly on top of the head and one magnet 310 for positioning on each of the front, back, left side, and right sides of the head. Each magnet 310 may be attached to the hat through any means known in the art, such as a nut and bolt connection 312 as seen in FIGS. 9-12. In some non-limiting embodiments, the magnets 310 may be held in place by additional ring magnets on the outside of the hat via the clamping force between the magnets. Embodiments having the magnets 310 held in place by ring magnets may be used in situations that require frequent removal and adjustment of the magnets 310. Additionally, additional ring magnets may be used to attach magnets 310 that do not have a central opening for receiving a bolt 312.

Figure 13:
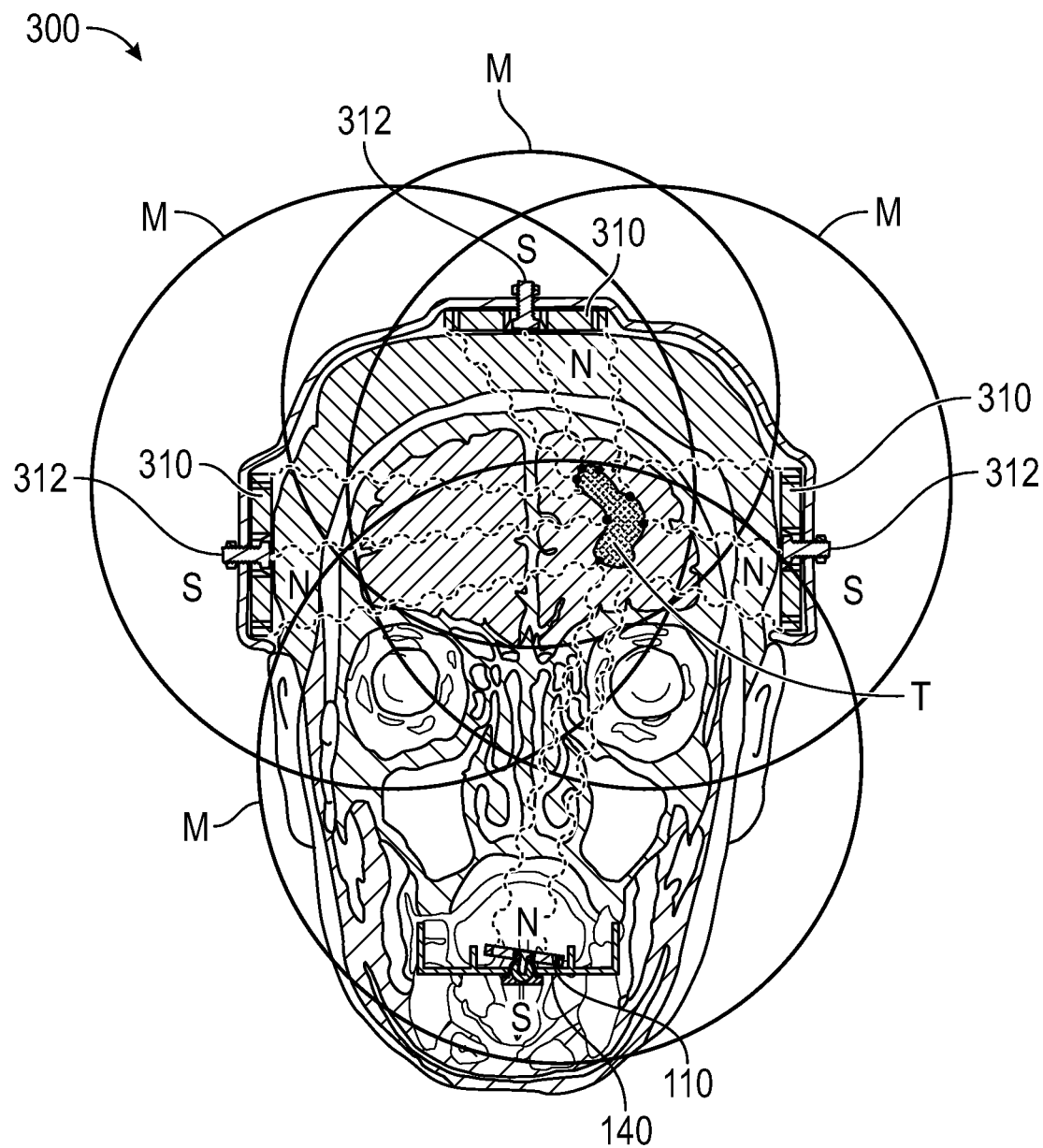
FIG. 13 is a sectioned view of the magnetic therapy hat of FIG. 8 on a user's head and the magnetic therapy mouth guard of FIG. 3 in the user's mouth, showing the magnetic fields produced by the magnets of the helmet and mouthguard.

FIG. 13 shows a cross-section, taken through the center of the top and side magnets 310 of the hat 300 on the head of a user (line 13 shown in FIG. 8), and the associated compressed, static magnetic fields provided by the hat 300. In the non-limiting embodiment shown in FIG. 13, each magnet 310 is a mounting magnet which includes a ring magnet surrounded by a spacer and a steel cup. The steel cup extends over the south pole of the magnet to direct the magnetic field towards the north pole, thus resulting in a more powerful magnetic field extending out from the north pole of the magnet 310 and into the patient's head. As seen in FIG. 13, the magnetic fields of the three shown magnets 310 are all compressed in the patient's brain. The magnets 310 in the front and back of the head, which are not shown in this cross-sectional view, would also be providing magnetic fields that are interesting with the shown magnetic fields. As such, the brain tissue of the patient resides within an intersection of five magnetic fields from the hat 300. In some embodiments, each magnet may be directing a south facing magnetic field into the patient's brain or, alternatively, some of the magnets may be directing south facing magnetic fields, while others are direct north facing magnetic fields, into the brain.

A user may also place a magnetic therapy mouth guard 14 in his/her mouth to provide an additional magnetic field. The mouth guard may include a centrally located magnet 110. The magnet 110 may be pivotally attached to the mouth guard by a ball joint or other pivoting mechanisms known in the art. As seen in FIG. 13, a user will be able to direct the magnetic field of the mouth guard, due to the pivotal relationship, at the target tissue to provide an additional compressed magnetic field.

FIG. 13A shows an example of a patient with a brain tumor (T). As seen by the circles (M) representing example static magnetic fields of the magnets 310, 110 (the example magnetic fields (M) are show in their before compression state to clarify the interaction between the fields), the tumor is being exposed to at least four compressed magnetic fields in addition to the magnetic fields of magnets 310 not located on the cross-section. As seen by the dashed lines, each magnet 310, 110 will provide a different strength magnetic field at the location of the tumor due to the differences in distance from the tumor. A larger distance from the magnet 310, 110 (longer dashed line) will result in a weaker magnetic field. In most cases, a stronger magnetic field provides greater results. Accordingly, in some cases, when the location of damaged or abnormal tissue is known, the magnets 310, 110 can be strategically placed so each compressed magnetic field is at its strongest.

Figure 14A:
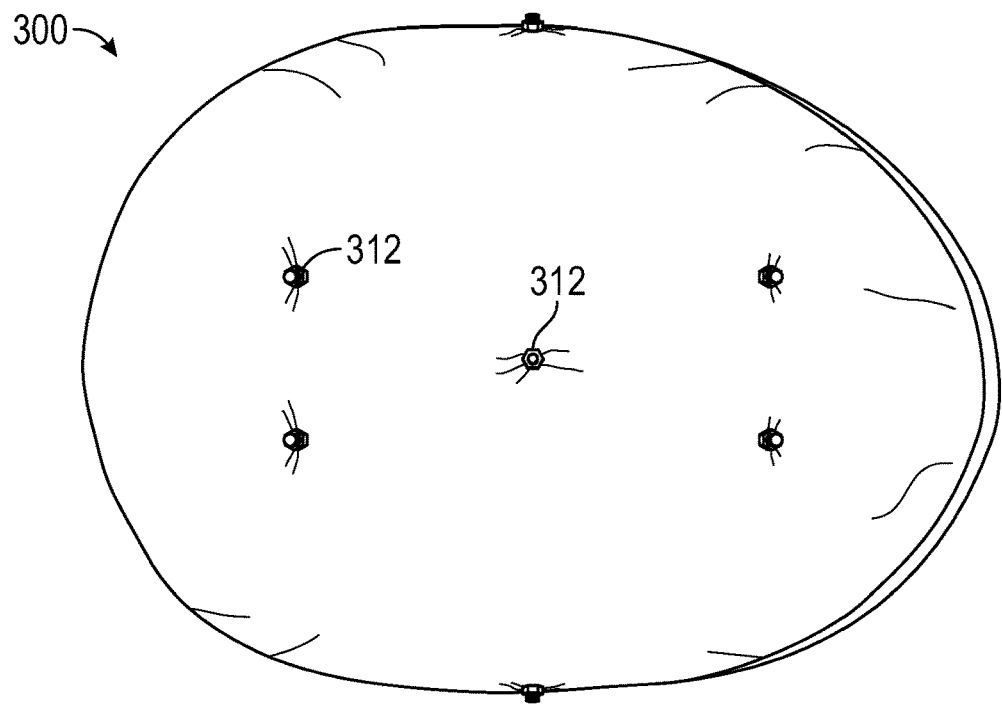
FIG. 14A is a top view of a second embodiment of a magnetic therapy hat.
Figure 14B:
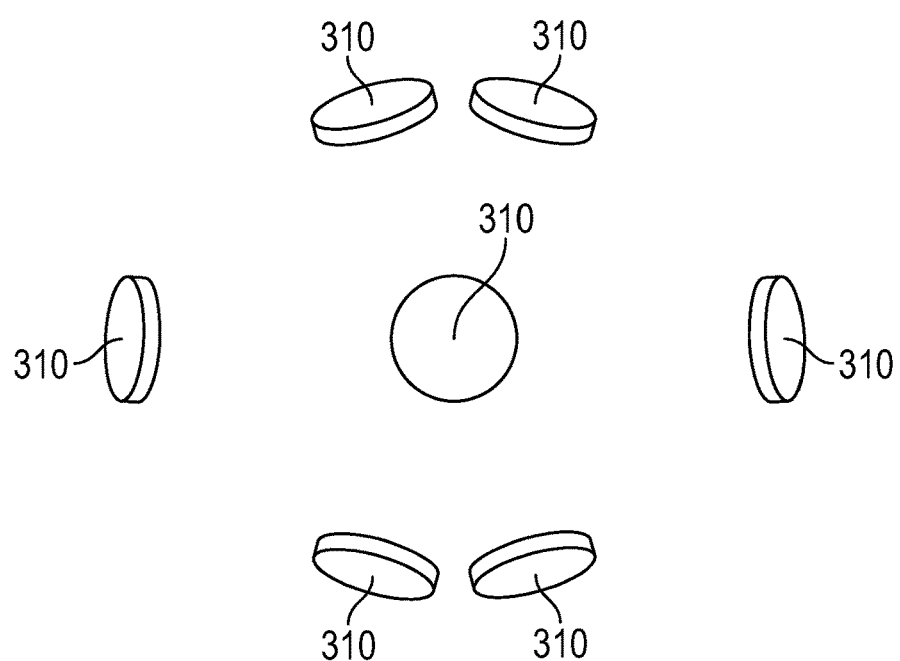
FIG. 14B is a diagram showing placement of the magnets within the hat of FIG. 14A.

FIGS. 14A and 14B depict the magnetic therapy hat 300 containing seven static magnets 310. The embodiment of FIGS. 14 and 15 includes additional magnets 310 in the front and back of the hat, as compared to the embodiment shown in FIGS. 8-13, which will be resting on the top of the head when the hat 300 is being worn by a user. The additional magnets 310 will provide more compressed magnetic fields at the targeted healthy tissue surrounding the treatment tissue, thus resulting in a more condensed magnetic field at and around the treatment tissue.

The previously discussed magnetic therapy helmet 100, magnetic therapy head harness 200, and the magnetic therapy hat, as well as any other device describe herein or any combination of magnets within the scope of this description may be used to treat neurological conditions such as chronic traumatic encephalopathy (CTE). CTE caused the neurons in the brain to die. Without intervention, dead neurons will not be regenerated. Exposing the dead neurons to a condensed magnetic field may result in an increase of stem cells at the location of the dead tissue resulting in new neurons being created.

To treat Alzheimer's disease, or other neurodegenerative diseases, a magnetic therapy helmet 100 may be placed on the patient's head to produce a compressed magnetic field around the patient's brain. In addition to the increased presence of stem cell due to the compressed magnetic fields, an injection tube 199 may be used to provide additional stem cells to the patient's brain.

Figure 15:
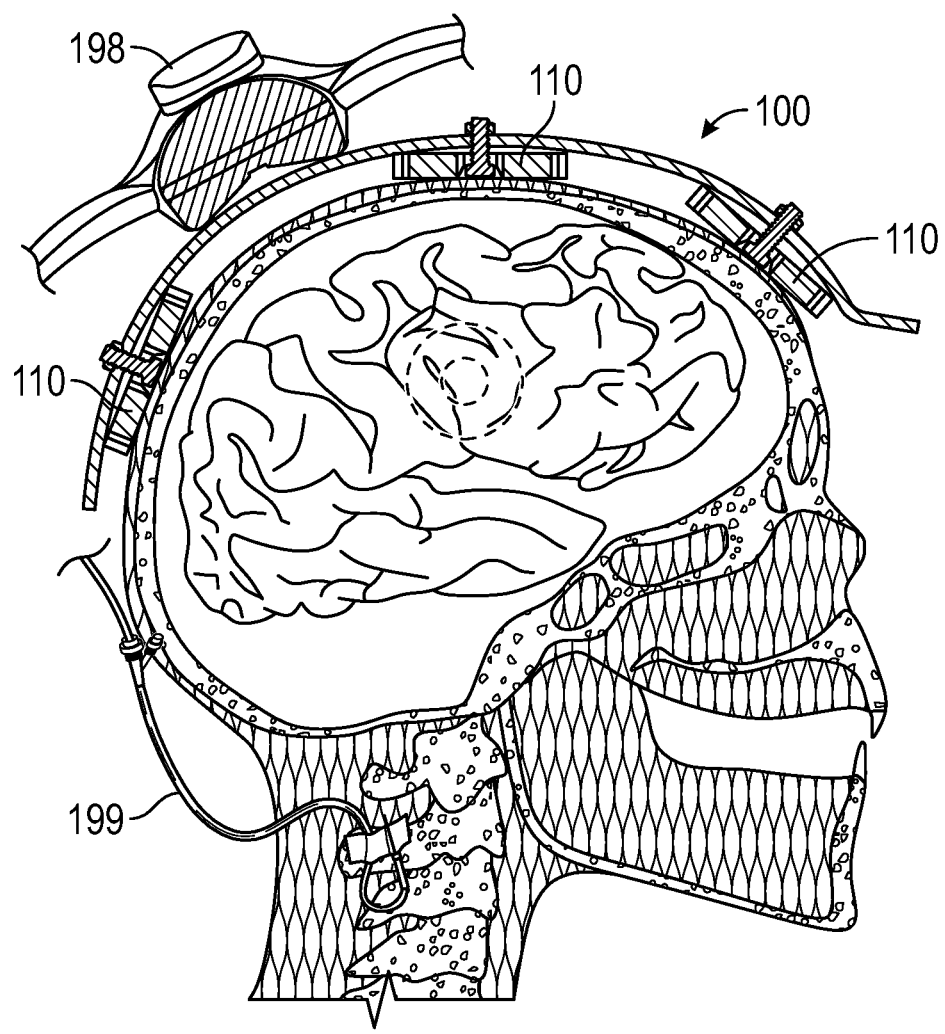
FIG. 15 is a sectional view of a head of a patient wearing the helmet of FIG. 1 for treating Alzheimer's.

FIG. 15 shows an embodiment of a static magnetic therapy helmet 100 being used to treat Alzheimer's disease. Alzheimer's disease is a result of neuron degeneration in the brain. The presently discussed magnetic therapy can be used to regenerate neurons through the increased presence of stem cells in the area of the compressed magnet fields. Additional stem cells may be delivered to the user by a delivery lumen 199.

Transcranial magnetic stimulation (TMS) may be used in conjunction with static magnetic therapy to further treat Alzheimer's disease. As seen in FIG. 15, a TMS device 198 may provide electromagnetic fields to the brain at the same time as the static magnetic fields of the magnets 110. The electromagnetic fields may prevent binding of beta-amyloid proteins to capillary walls by drawing electrical charge to the capillary wall which in turn repels the charged beta-amyloid protein. The repetitive nature of the electromagnetic field produced by the TMS device 198 may also break apart beta-amyloid protein clumps on the capillary walls. Additionally, a pulsed electromagnetic field generator, such as a Bemer 3000™, may be used with the static magnetic field therapy, or the combination of the static and electromagnetic field therapy discussed above, to further treat Alzheimer's disease. Quantitative electroencephalography (qEEG) may be used to map the brain during treatment to precisely align the static magnets 110 and the electromagnetic field of the TMS device 198.

Figure 16:
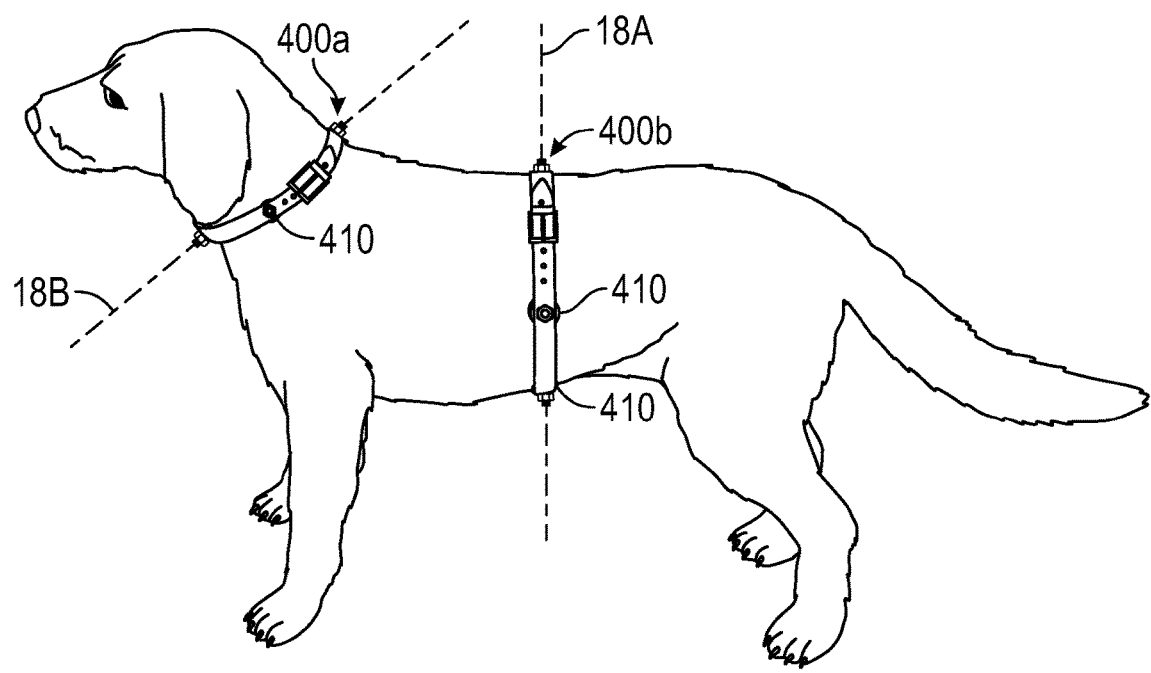
FIG. 16 is an environmental view of magnetic therapy belts being worn by a dog.
Figure 17:
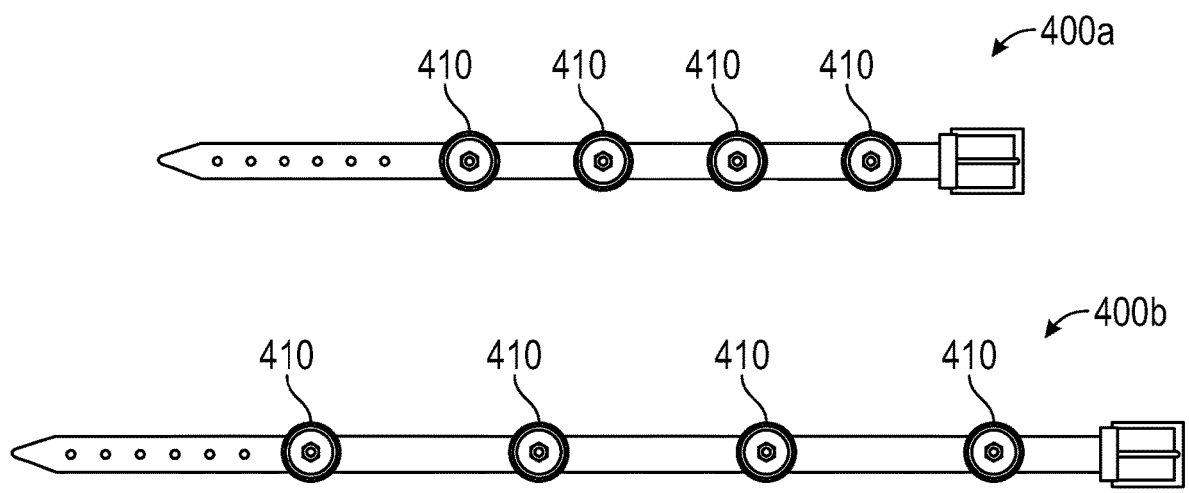
FIG. 17 is a bottom view of the belts of FIG. 16.

FIGS. 16-18B depict magnetic belts 400a, 400b which provide compressed, static magnetic fields within a portion of a body surrounded by the belt 400a, 400b. For example, as shown in FIG. 16 the belts 400a, 400b can be used on and animal, such as a dog, with a first belt 400b acting as a torso belt and a second belt 400a acting as a collar. Each belt 400a, 400b may support at least two magnets 410 along its length on a body facing surface of the belt 400a, 400b. In some non-limiting embodiments, the magnets 410 may be equally spaced to provide consistent coverage to the wrapped body part as a whole. In other non-limiting embodiments, the magnets 410 may be positioned to provide more powerful compressed magnetic fields at a specific location. The locations and amounts of magnets, as well as the animal shown, in FIG. 16 are provided as examples. The belts 400a, 400b may be used on any type of animal and may be wrapped around any part of the body that may require, or benefit from, magnetic treatment. In some embodiments, the belts 400a, 400b may include between 2 and 25 magnets.

Figure 18A:
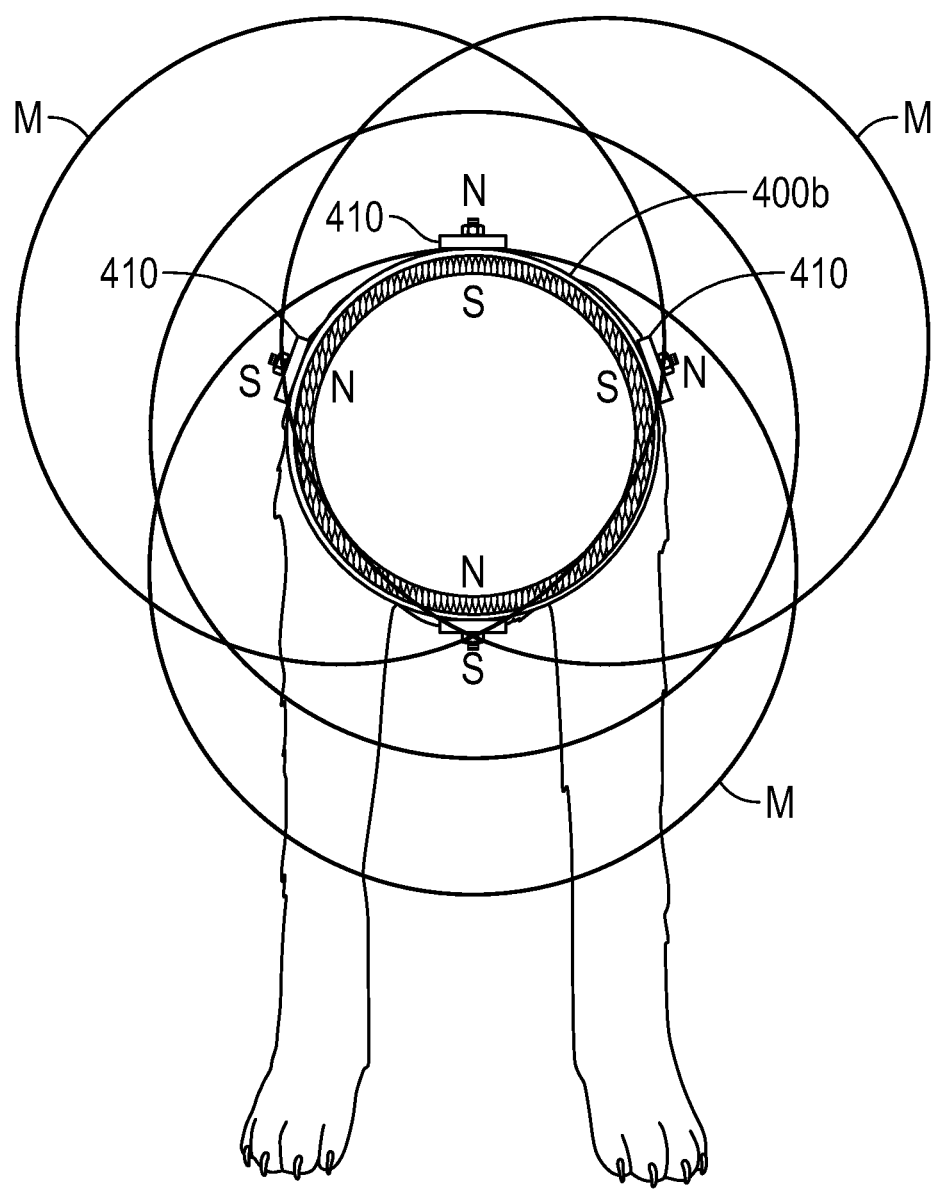
FIG. 18A is a sectioned view of the magnetic therapy belt and dog of FIG. 16 taken at line 18A.
Figure 18B:
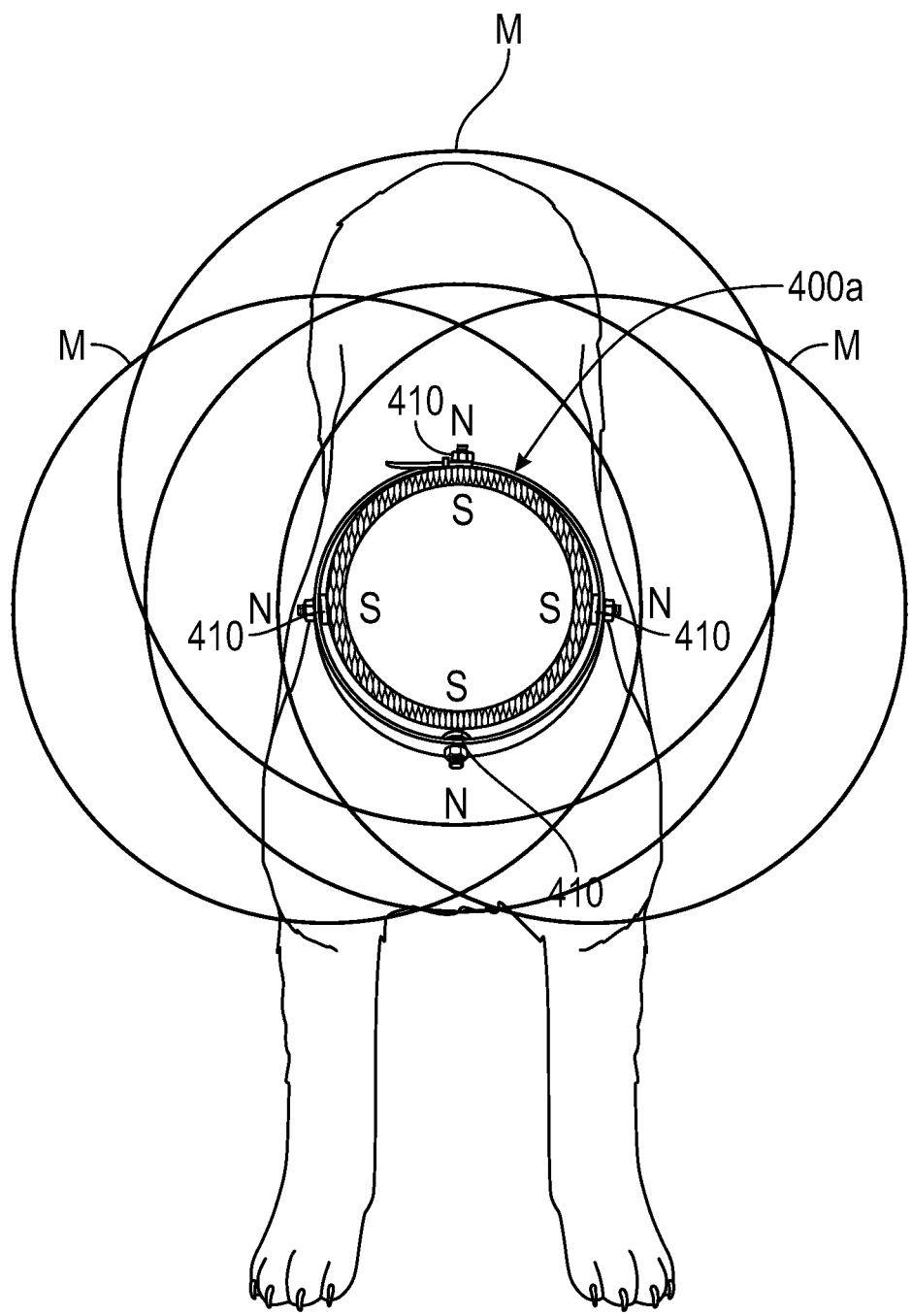
FIG. 18B is a sectioned view of the magnetic therapy belt and dog of FIG. 16 taken at line 18B.
Figure 19:
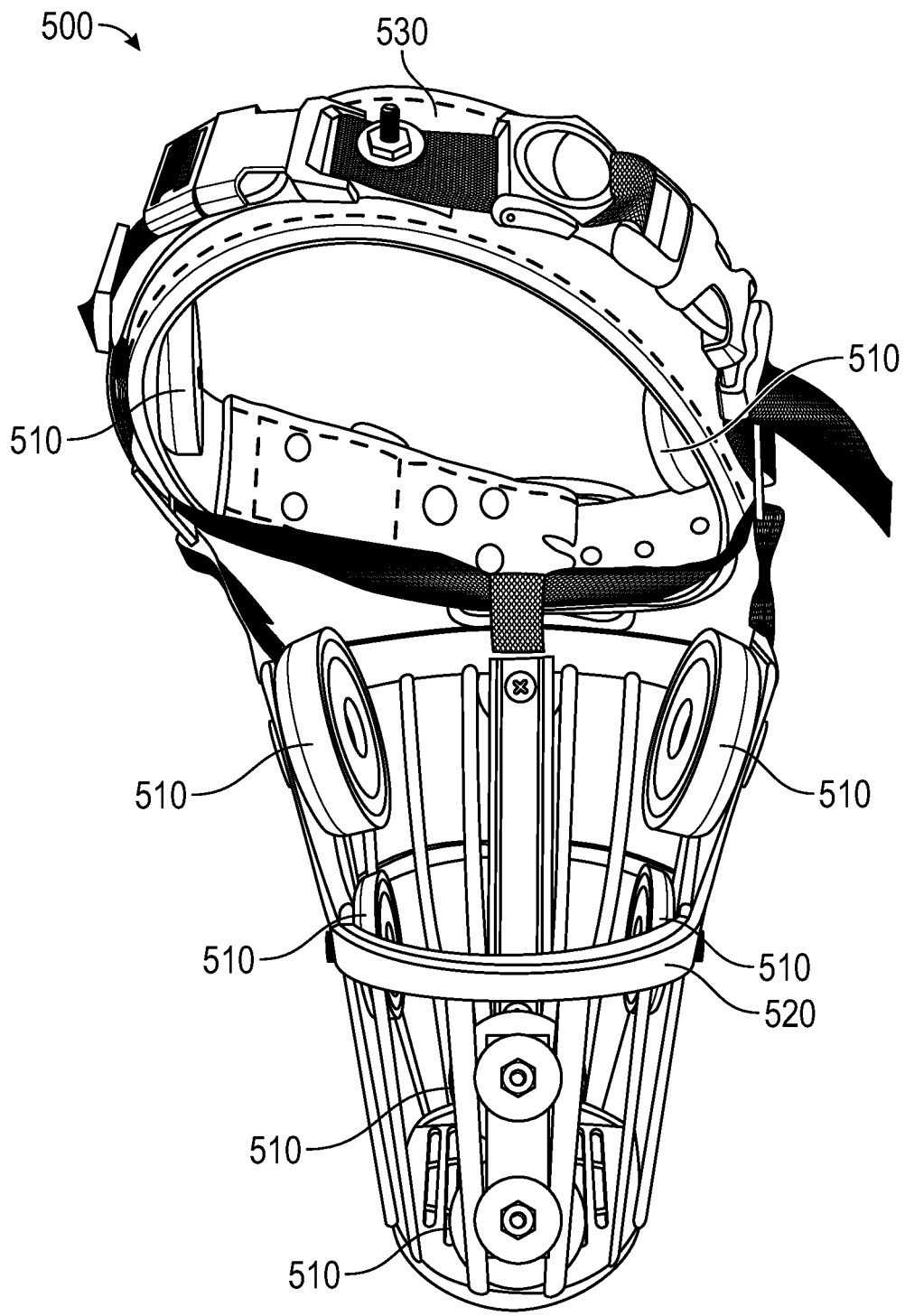
FIG. 19 is an overhead perspective view of a magnetic therapy muzzle.
Figure 20:
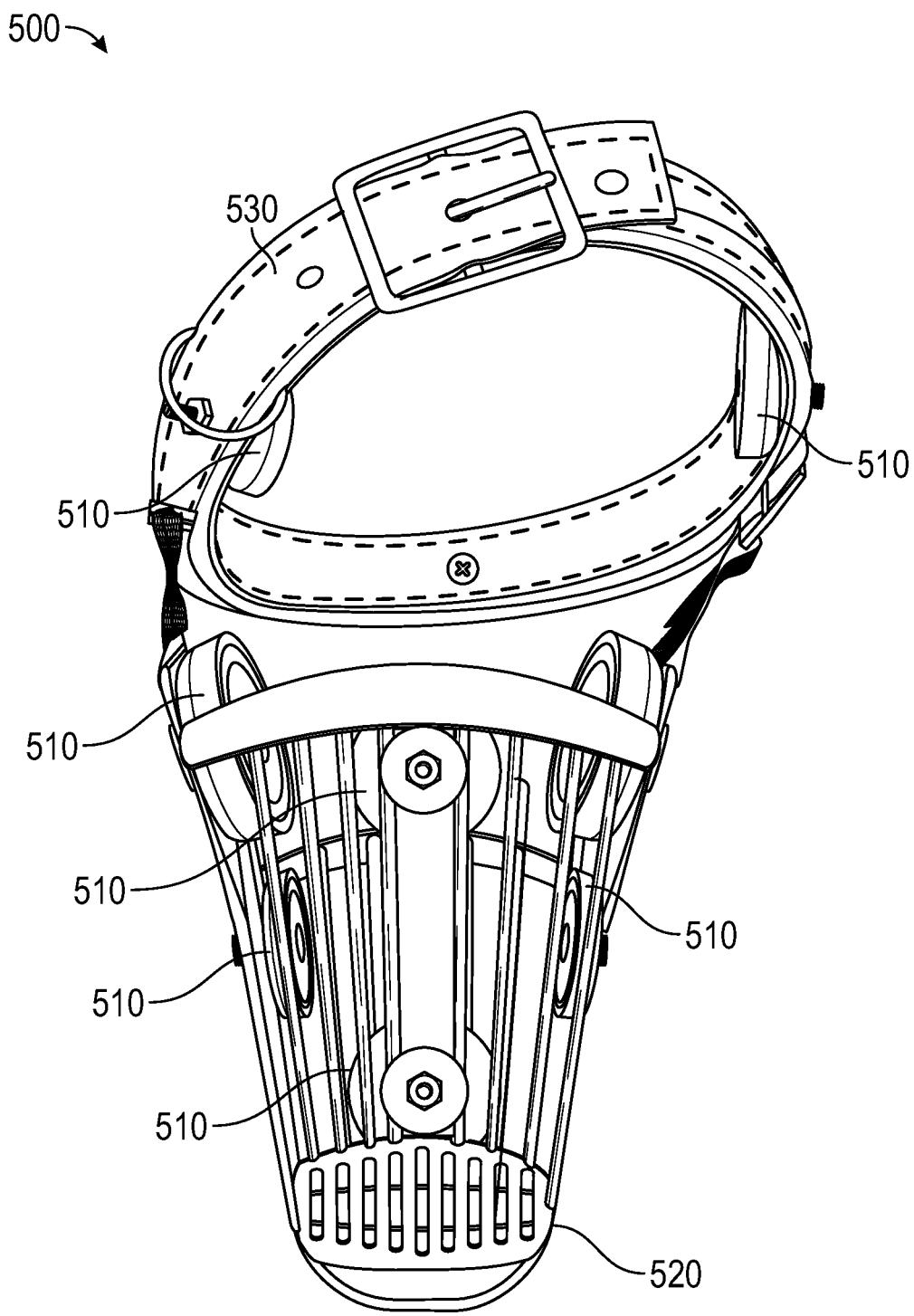
FIG. 20 is a perspective view of the magnetic therapy muzzle of FIG. 19 from below.
Figure 21:
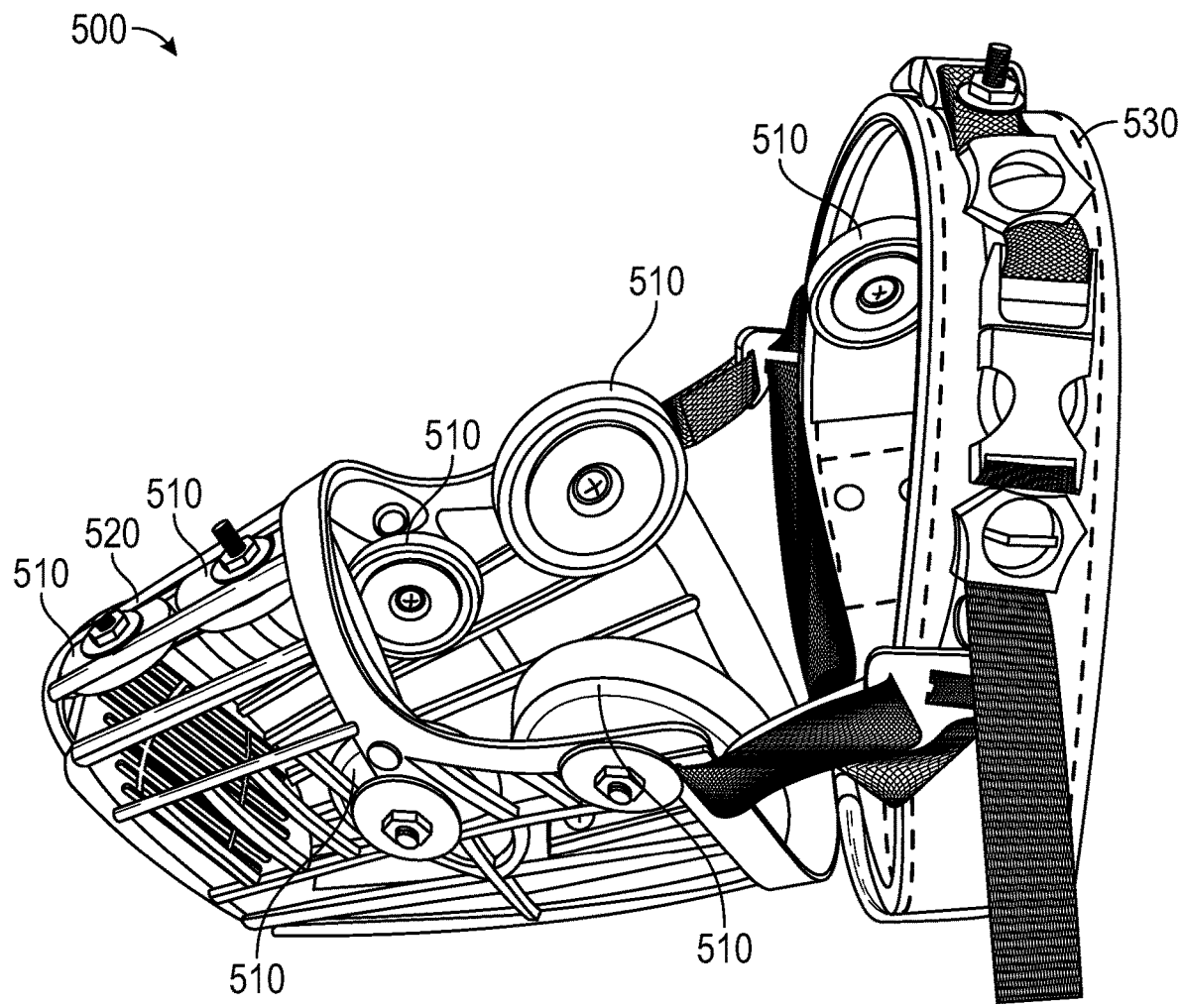
FIG. 21 is a perspective view of the magnetic therapy muzzle of FIG. 19 from the side.
Figure 22:
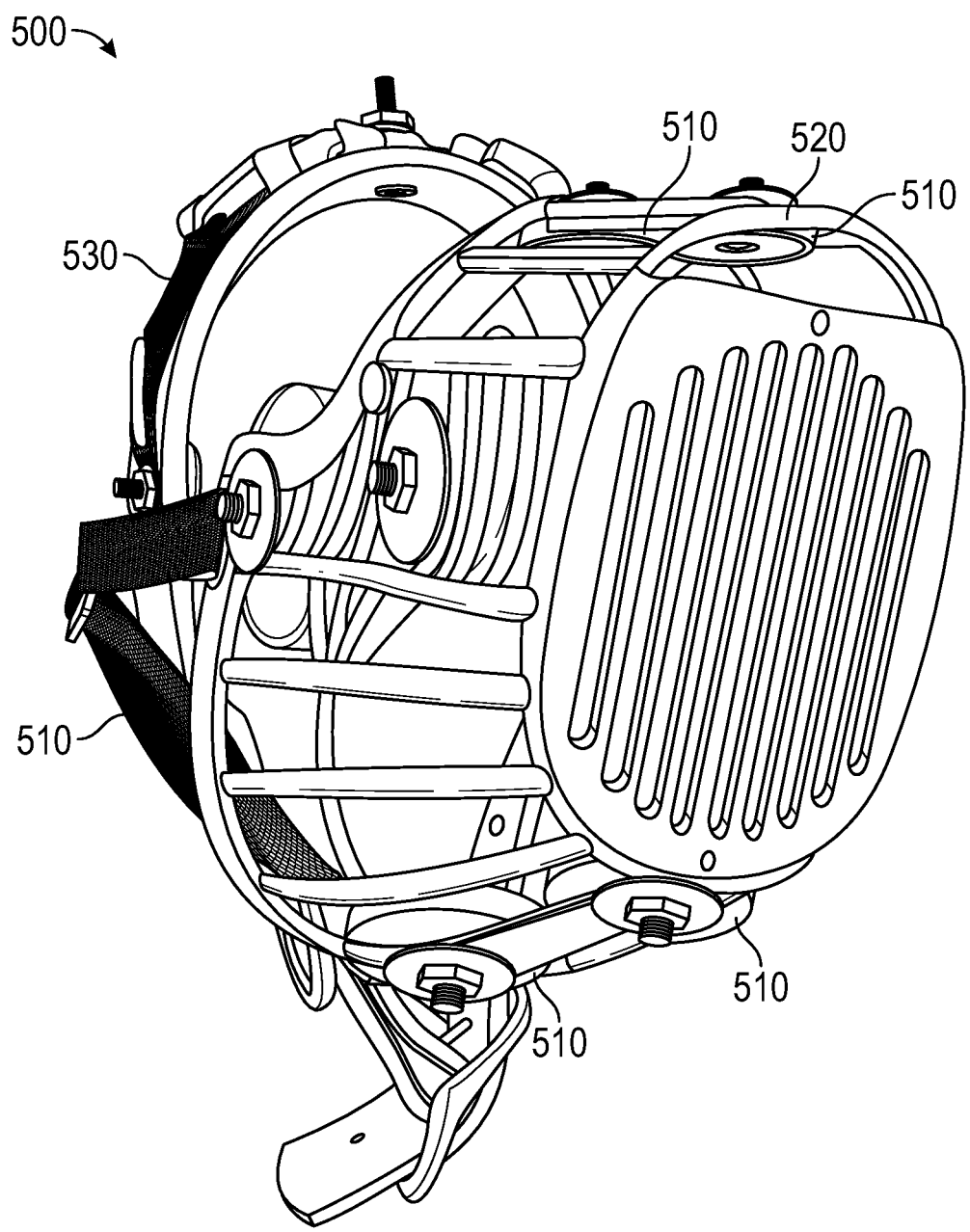
FIG. 22 is a perspective view of the magnetic therapy muzzle of FIG. 19 from the front.

FIGS. 18A and 18B depict cross-sections of FIG. 16 at each belt 400a, 400b, as well as circles (M) indicating examples of the associated magnetic fields (the fields (M) are shown in a non-compressed state to clarify the interaction between the fields). FIG. 18A shows a cross-section of the torso belt 400b based on line 18A of FIG. 16. In the non-limiting embodiment of FIG. 18A, two magnets 410 are oriented with the north pole facing inwards and two magnets are oriented with the south pole facing inwards. As shown in FIG. 18A, the torso of the dog will be exposed to the intersection of the strongest portions of the magnetic fields of each magnet 410. The belt 400a, shown in FIG. 18B which is based on line 18B of FIG. 16, alternatively has each magnet 410 oriented so the south pole is facing inwards to produce compressed static magnetic fields through the neck of the dog.

FIGS. 19-23 depict a magnetic therapy muzzle 500 which provides compressed, static magnetic fields through the snout, mouth, and jaw of the muzzled animal. The muzzle 500 includes a rigid cage 520 with multiple attached magnets 510 which may be directed into the cage. Multiple magnets 510 may be located on each side of the jaw, as well as on the top and bottom of the jaw. In some non-limiting embodiments, each side of the cage 520 may be fitted with between 1 and 10 magnets and the top and bottom of the cage 520 may each be fitted with between 1 and 10 magnets. The location and size of the magnets 510 may be selected based on the treatment sought and/or size of the animal. In some embodiments, each magnet 510 may have a complimentary magnet 510 on the opposing side of the cage 520, as shown in the embodiment of FIGS. 19-23. A collar 530 may be attached to the cage 520 to assist in securing the cage 520 to the face of the animal. The collar 530 may also include two or more magnets 510, similar to the embodiments of FIGS. 16-18B. The shape of the rigid cage 520 may be adjusted for different animals with different snout sizes.

Figure 24:
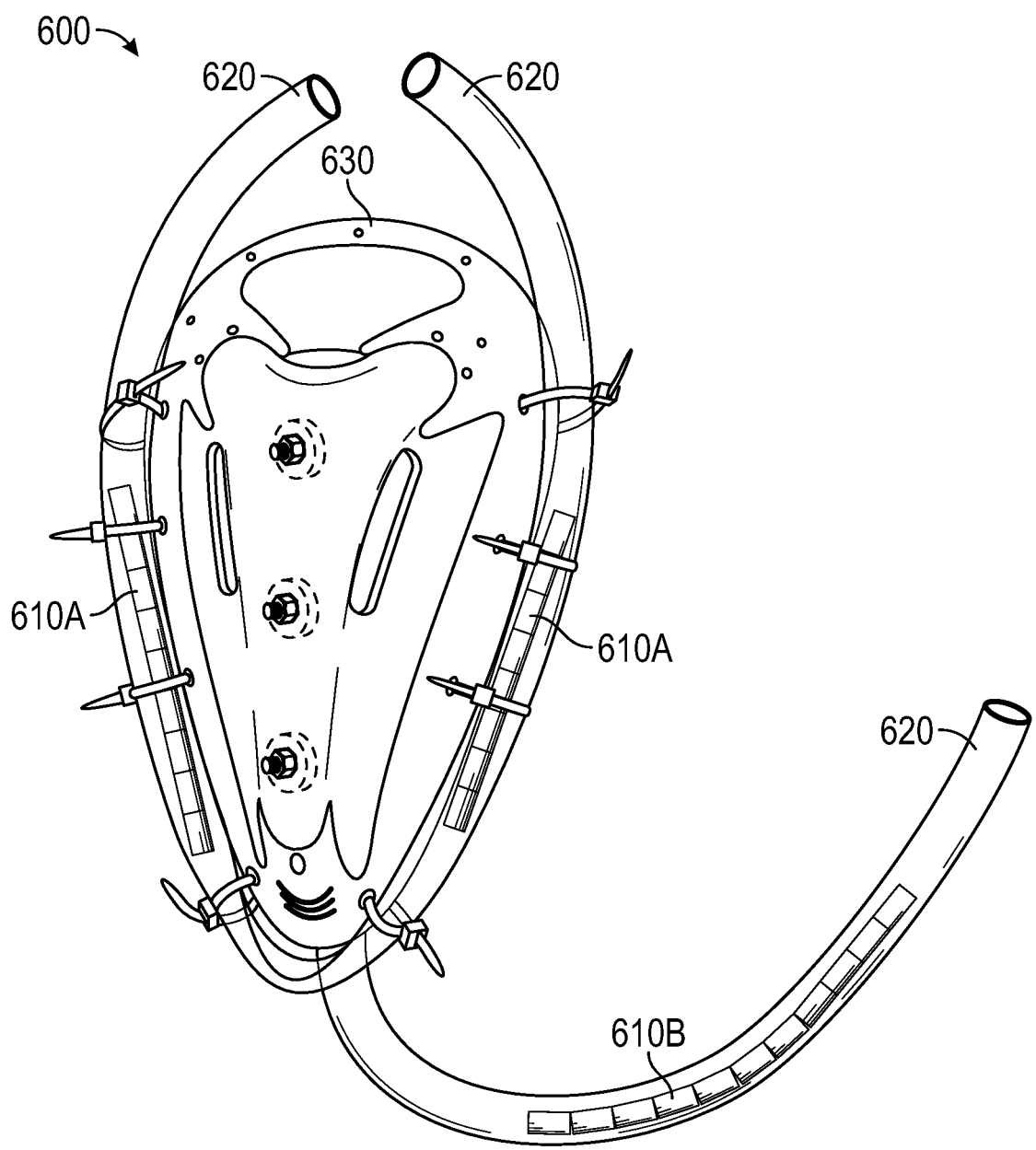
FIG. 24 is a perspective view of a magnetic therapy jock from the front.
Figure 25:
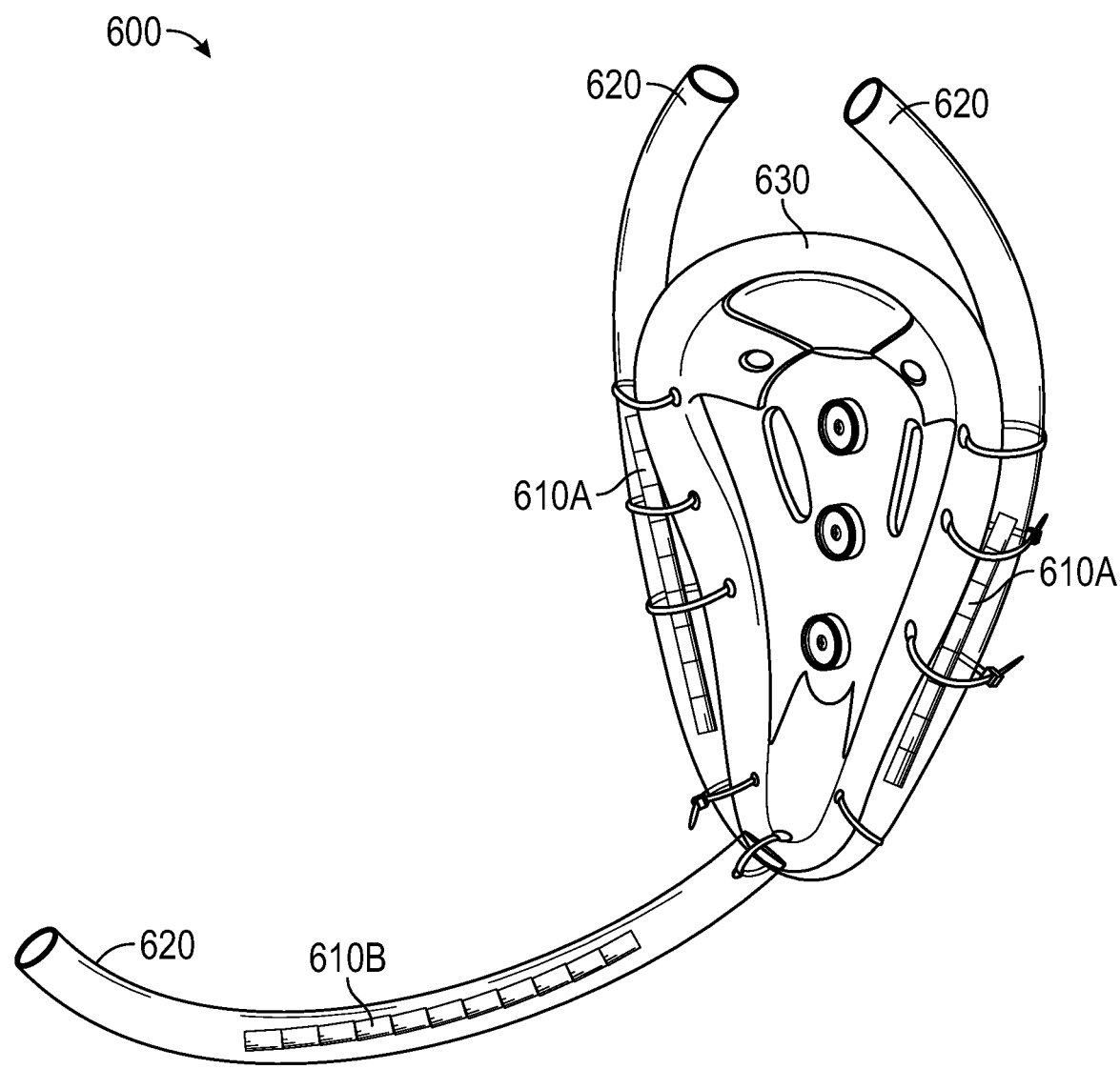
FIG. 25 is a perspective view of the magnetic therapy jock of FIG. 24 from the rear.

FIGS. 24 and 25 depict a magnetic therapy jock 600 which may be used to provide compressed, static magnetic fields through the groin area of a patient. The jock 600 may include a male athletic cup 630, as shown in FIGS. 24-25, or a female athletic pelvis protector. Left and right frontal magnets 610A may be provided around a periphery of the cup 630. A strip of rear magnets 610B may extend down from a bottom of the cup 630 for being placed within the intergluteal cleft. Mounting magnets 610C may be attached to the cup and directed inwards towards a user. In the non-limiting embodiment shown in FIGS. 24 and 25, cylindrical magnets 610A, 610B are contained within tubes 620 attached to the sides of the cup 630. In other embodiments, the magnets 610A, 610B may be attached to the cup 630 by other means known in the art. A strap (not shown in the FIGS.), such as an adjustable belt or jock strap, may connect the tubes 620 and cup 630 to assist in holding the magnets 610 in the desired positions. The magnetic jock 600 may include a magnetic belt similar to the belts shown in FIGS. 16-18. In some non-limiting embodiments, a rigid "V" or "U" shaped structure may hold the left and right frontal magnets 610A without the use of a cup 630 or pelvic protector.

In use, the magnetic jock 600 may be warn similar to an athletic jock with the left and right frontal magnets 600A on respective sides of the front of the groin region with the rear magnets 600B residing within the intergluteal cleft. The magnetic field of each magnet 600A, 600B will resultantly compress within the groin region and may be used for treating the urinary tract, bladder, reproductive tissue, and rectum tissue.

Figure 26:
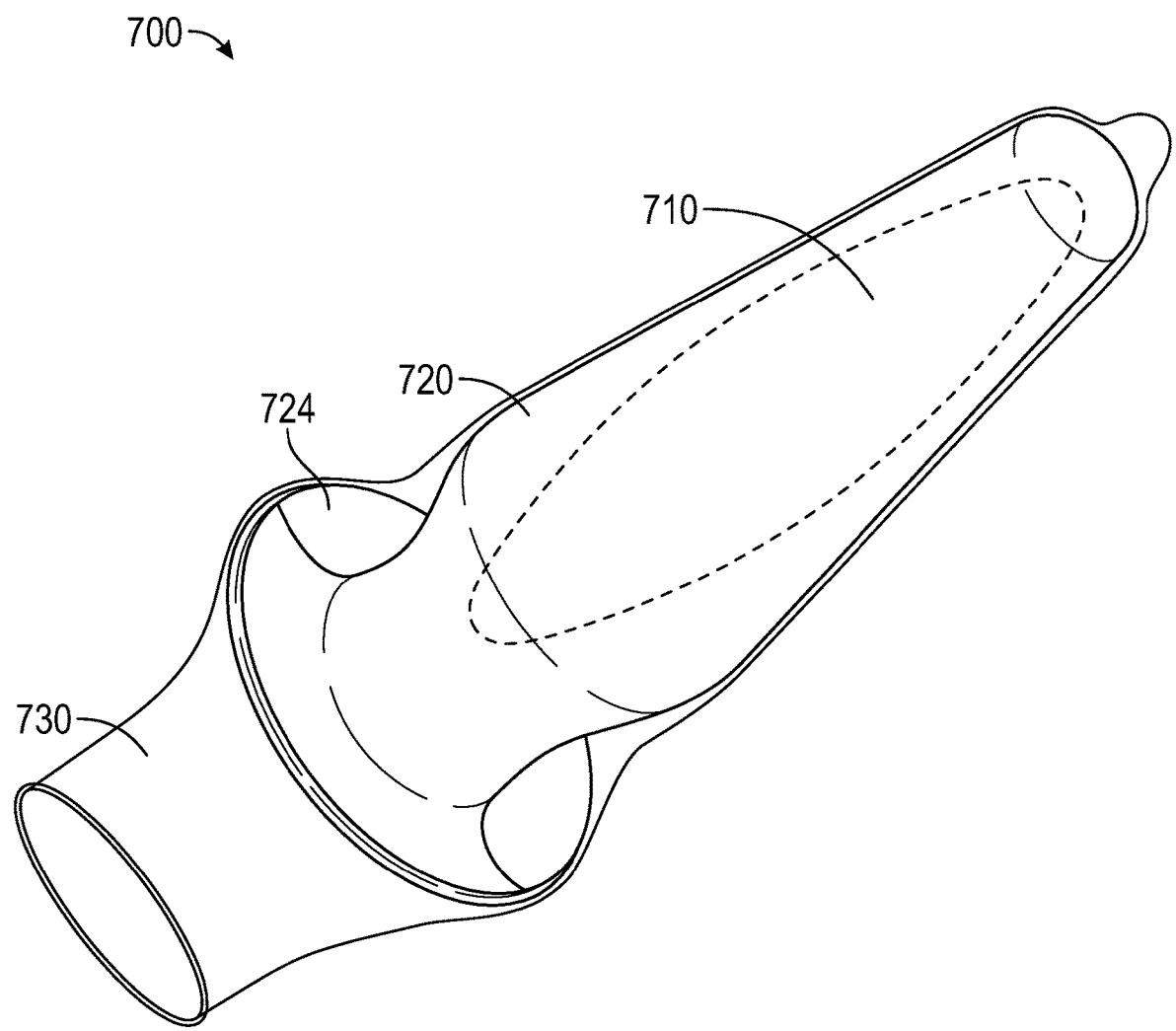
FIG. 26 is a perspective view of a rectal magnetic therapy device.
Figure 27:
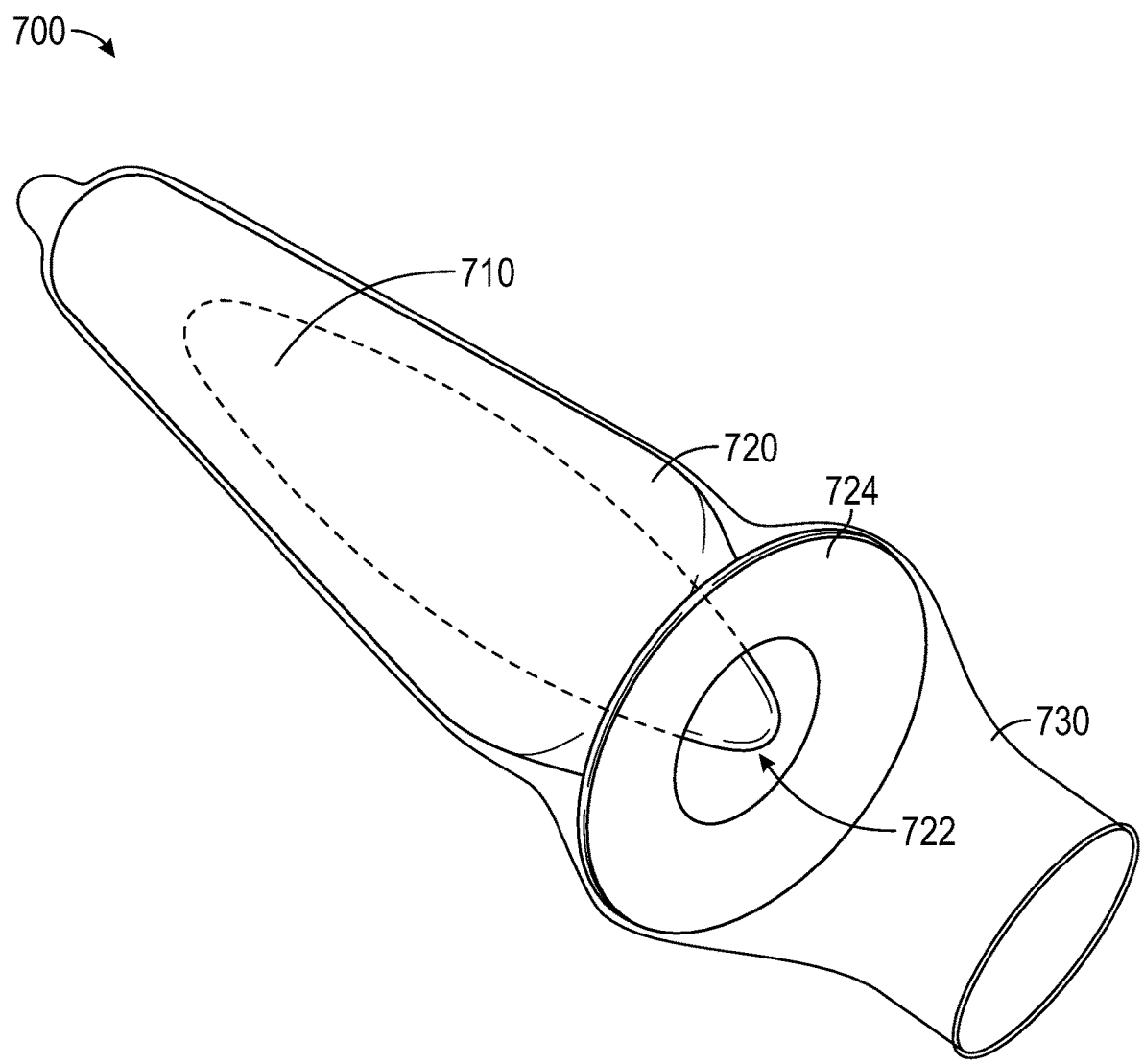
FIG. 27 is a perspective view of the rectal magnetic therapy device of FIG. 26 from below.
Figure 28:
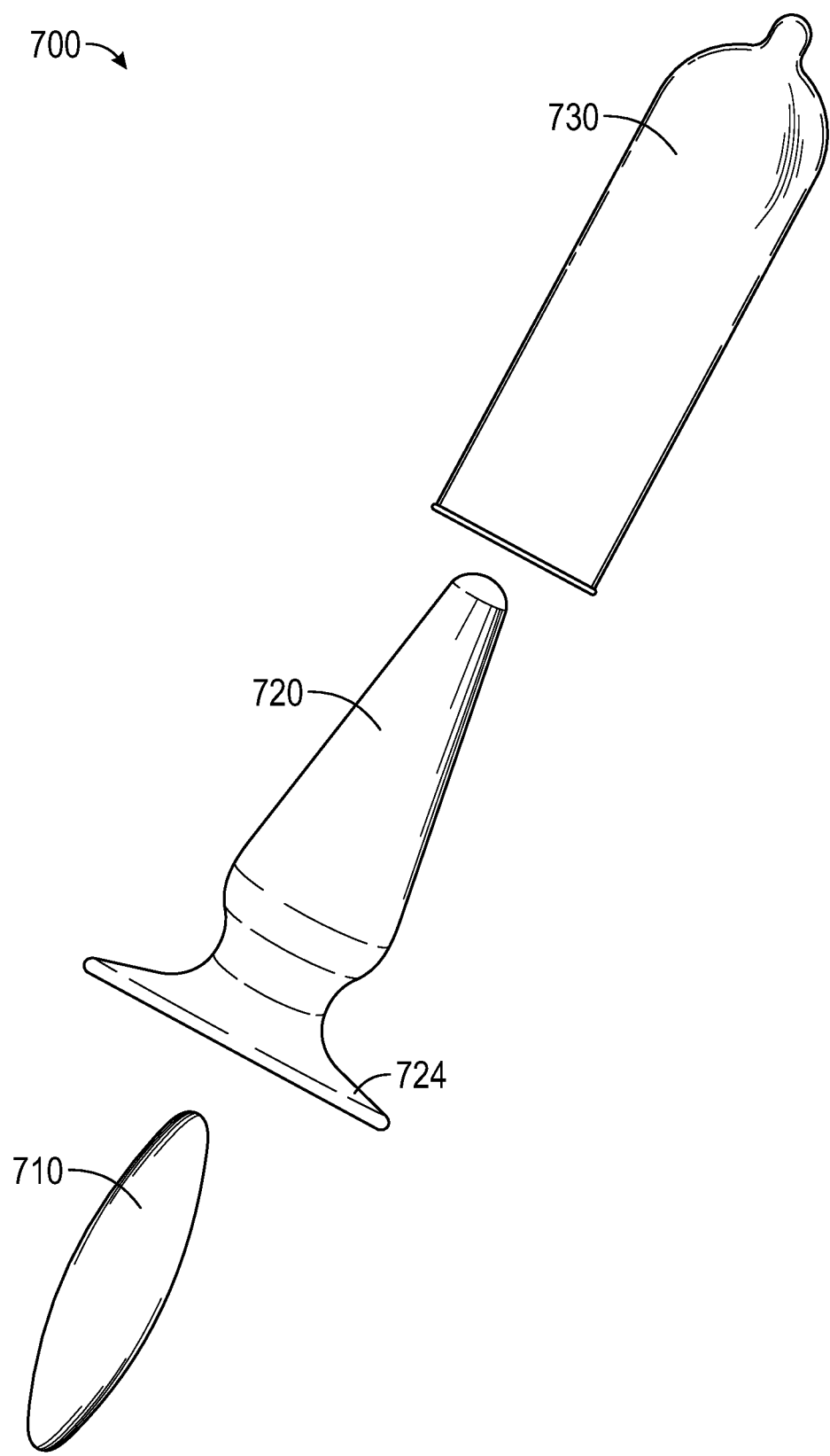
FIG. 28 is an exploded view of the rectal magnetic therapy device of FIG. 26.

FIGS. 26-28 depict an embodiment of a rectal magnetic therapy device 700 for providing a static magnetic field extending into the body from the rectum. The device 700 may include an outer body 720 defining a cavity 722 and a flange 724. A magnet 710 may be housed within the cavity 722. In some non-limiting embodiments, the magnet 710 may be cylindrical or egg shaped. A disposable sheath 730 may be used to cover the body 720 during use. During use, the body 720 of the device 700 may be inserted into the rectum and held in place by the flange 724, thus positioning the magnet 710 within the rectum of the user. The rectal magnet 70 may be used with other magnetic therapy devices such as the magnetic jock 600 of FIGS. 24-25 and/or the belts 400A, 400B of FIGS. 16-18 to provide an additional magnetic field from within the body. The poles of the device 700 may be oriented based on other compressed magnetic fields. For example, if the magnets 410 from a belt 400B worn around a patient's waste are all oriented with the north pole facing inwards, the north pole may be oriented towards the tip of the device 700.

Figure 29:
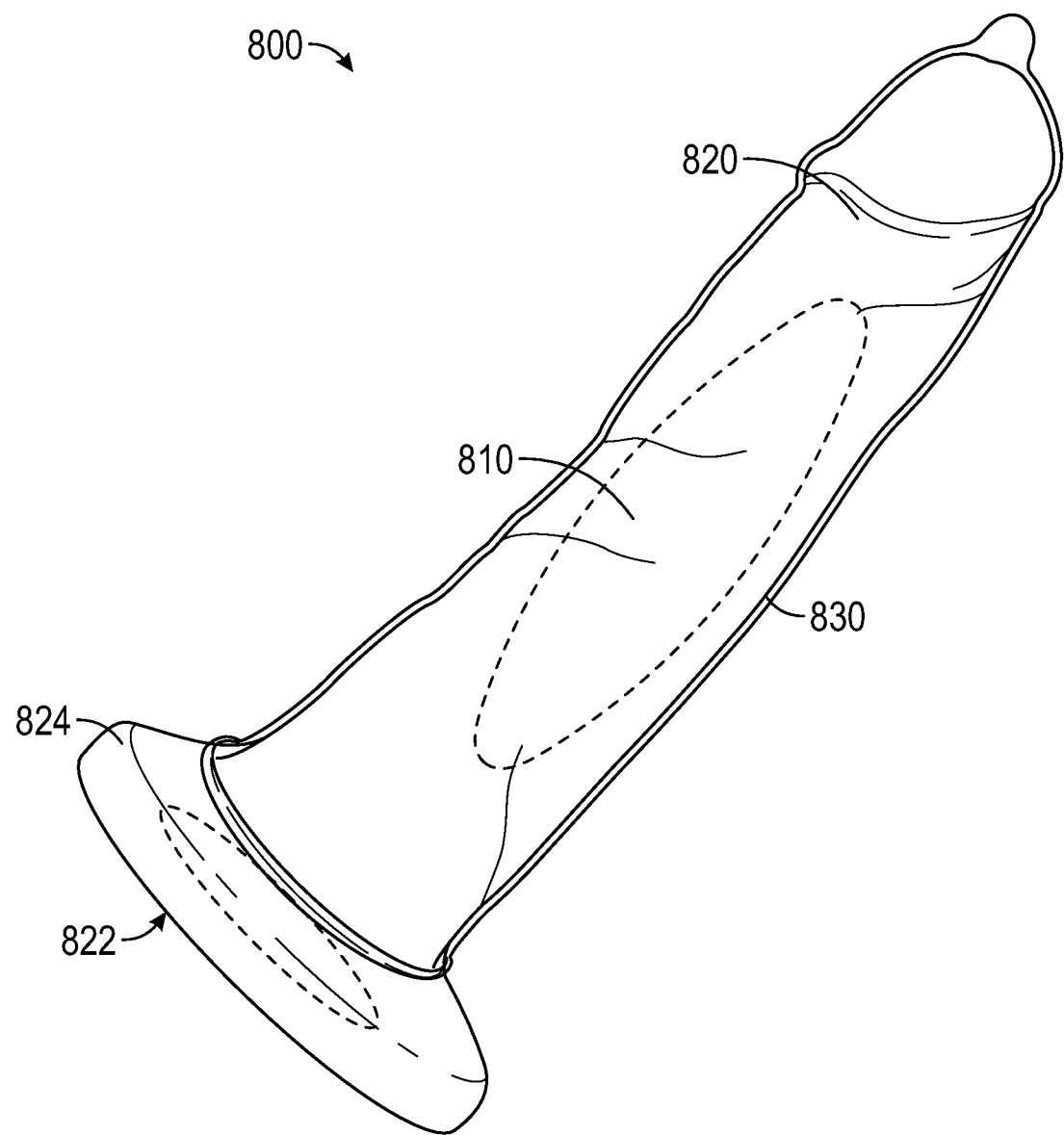
FIG. 29 is a perspective view of a vaginal magnetic therapy device.
Figure 30:
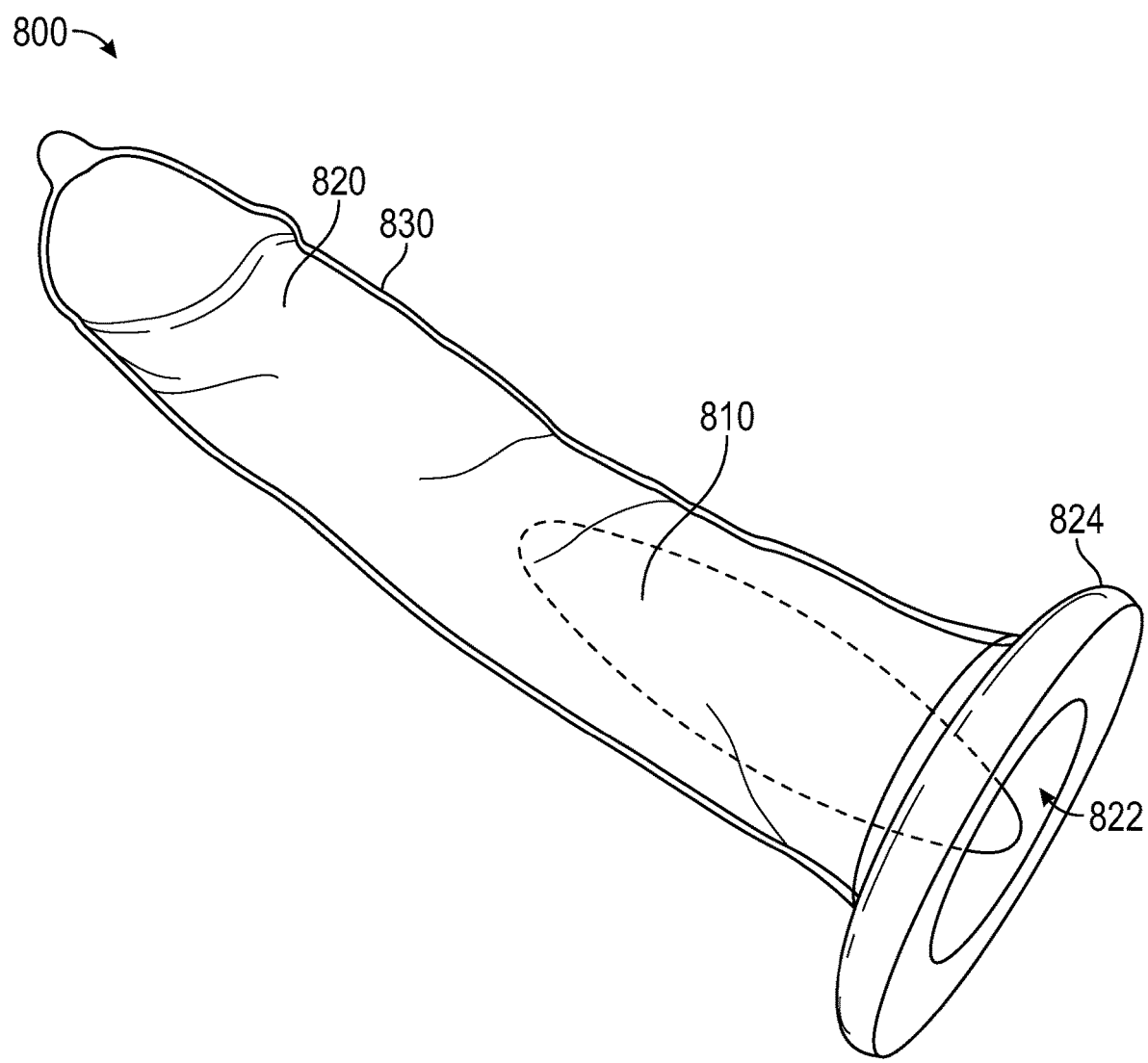
FIG. 30 is a perspective view of the vaginal magnetic therapy device of FIG. 29 from below.
Figure 31:
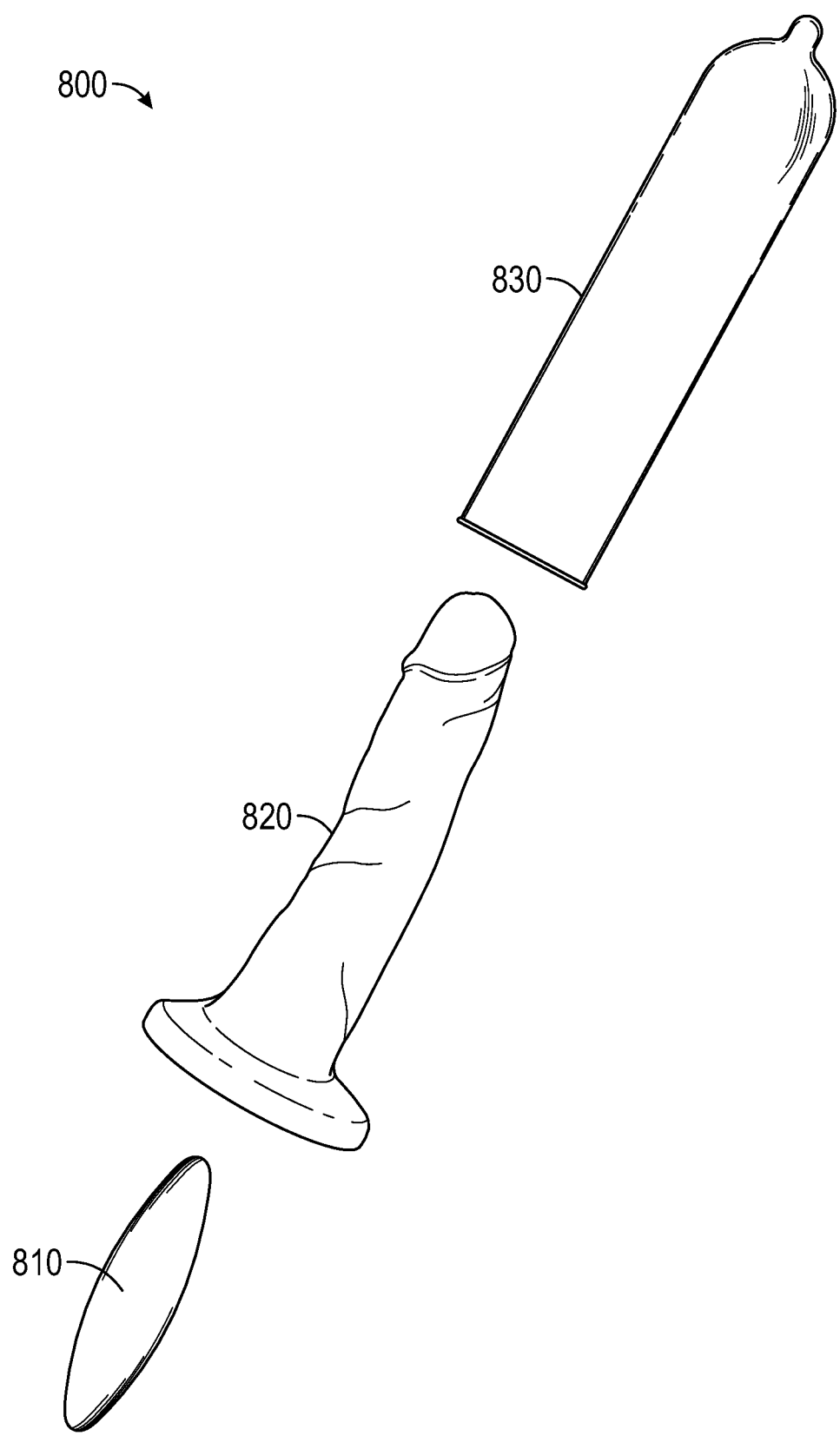
FIG. 31 is an exploded view of the vaginal magnetic therapy device of FIG. 29.

FIGS. 29-31 depict an embodiment of a vaginal magnetic therapy device 800 for providing a static magnetic field extending into the body from within the vaginal canal. The device 800 may include an outer body 820 defining a cavity 822 and a flange 824. A magnet 810 may be housed within the cavity 822. In some non-limiting embodiments, the magnet 810 may be cylindrical or egg shaped. A disposable sheath 830 may be used to cover the body 820 during use. During use, the body 820 of the device 800 may be inserted into the vagina and held in place by the flange 822, thus positioning the magnet 810 within the vaginal canal of the user. The device 800 may be used with other magnetic therapy devices such as the magnetic jock 600 of FIGS. 24-25, the belts 400A, 400B of FIGS. 16-18, and/or the rectal magnet 700 of FIGS. 26-28 to provide an additional magnetic field from within the body. The poles of the vaginal magnet 700 may be oriented based on other compressed magnetic fields. For example, if the magnets 410 from a belt 400B worn around a patient's waste are all oriented with the north pole facing inwards, the north pole may be oriented towards the tip of the device 800.

Figure 32:
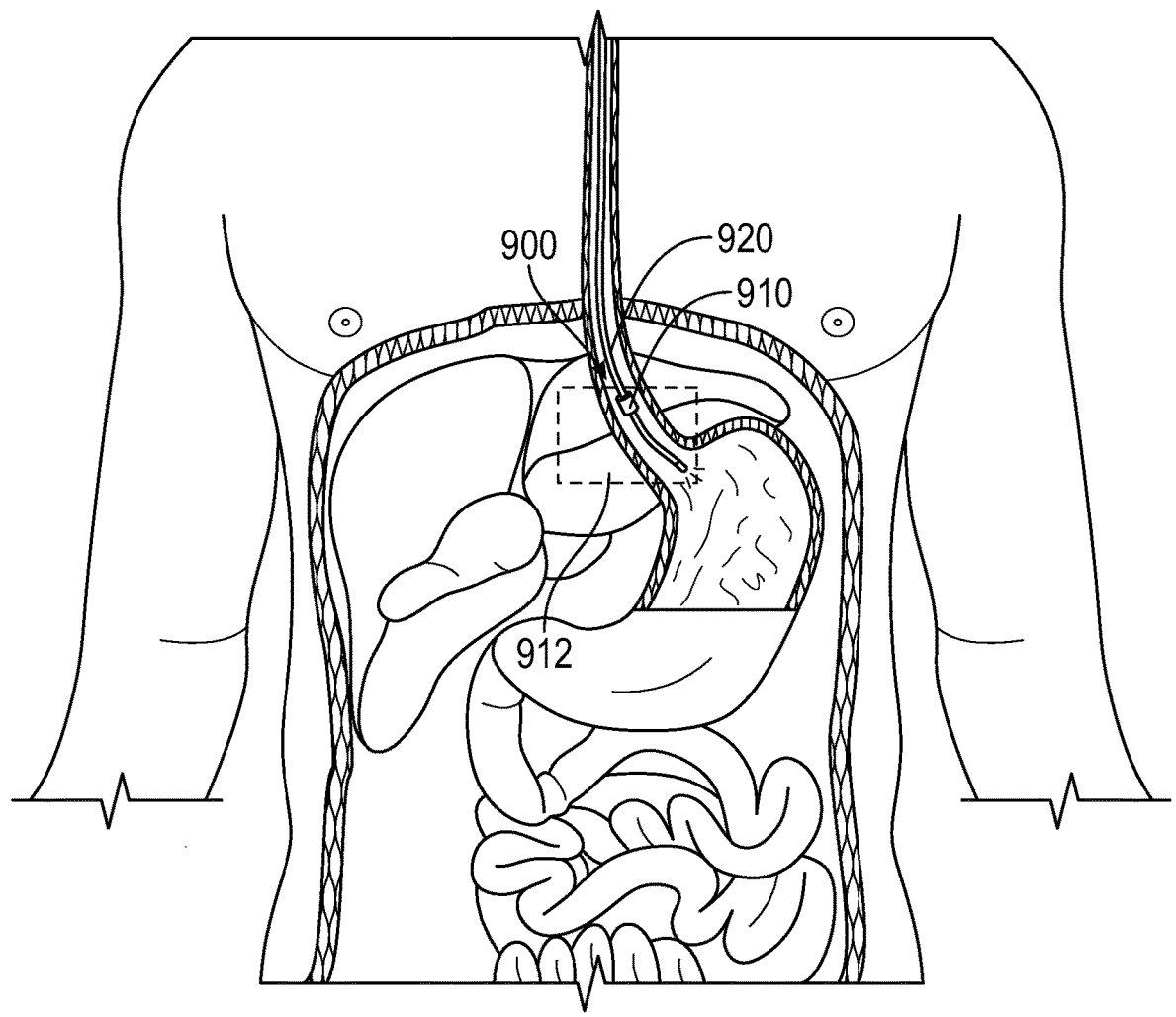
FIG. 32 is an environmental view of a gastrointestinal magnetic therapy device within a frontal, sectioned view of a human body.
Figure 33:
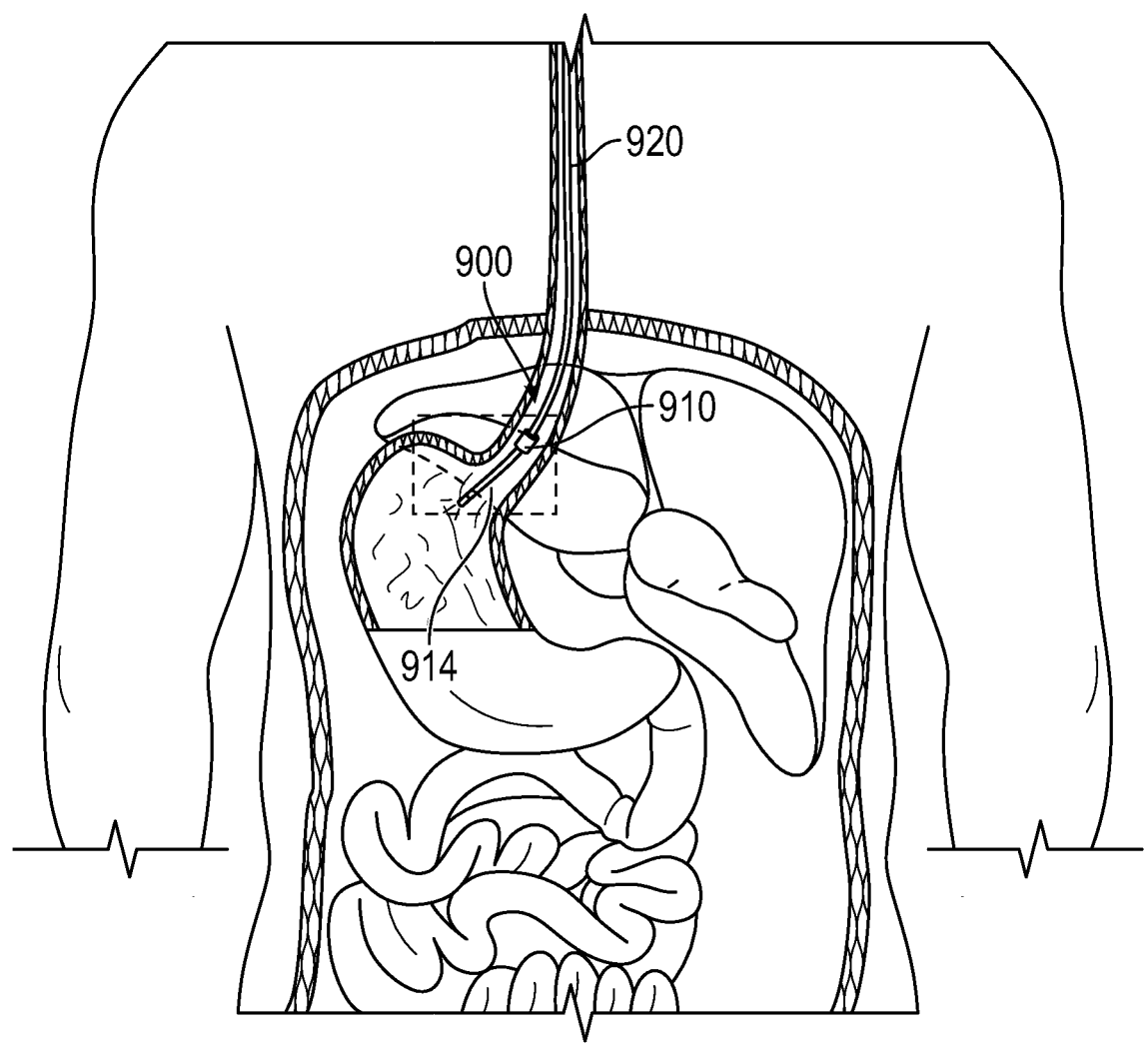
FIG. 33 is an environmental view of the gastrointestinal magnetic therapy device of FIG. 32 within a rear, sectioned view of a human body.
Figure 34:
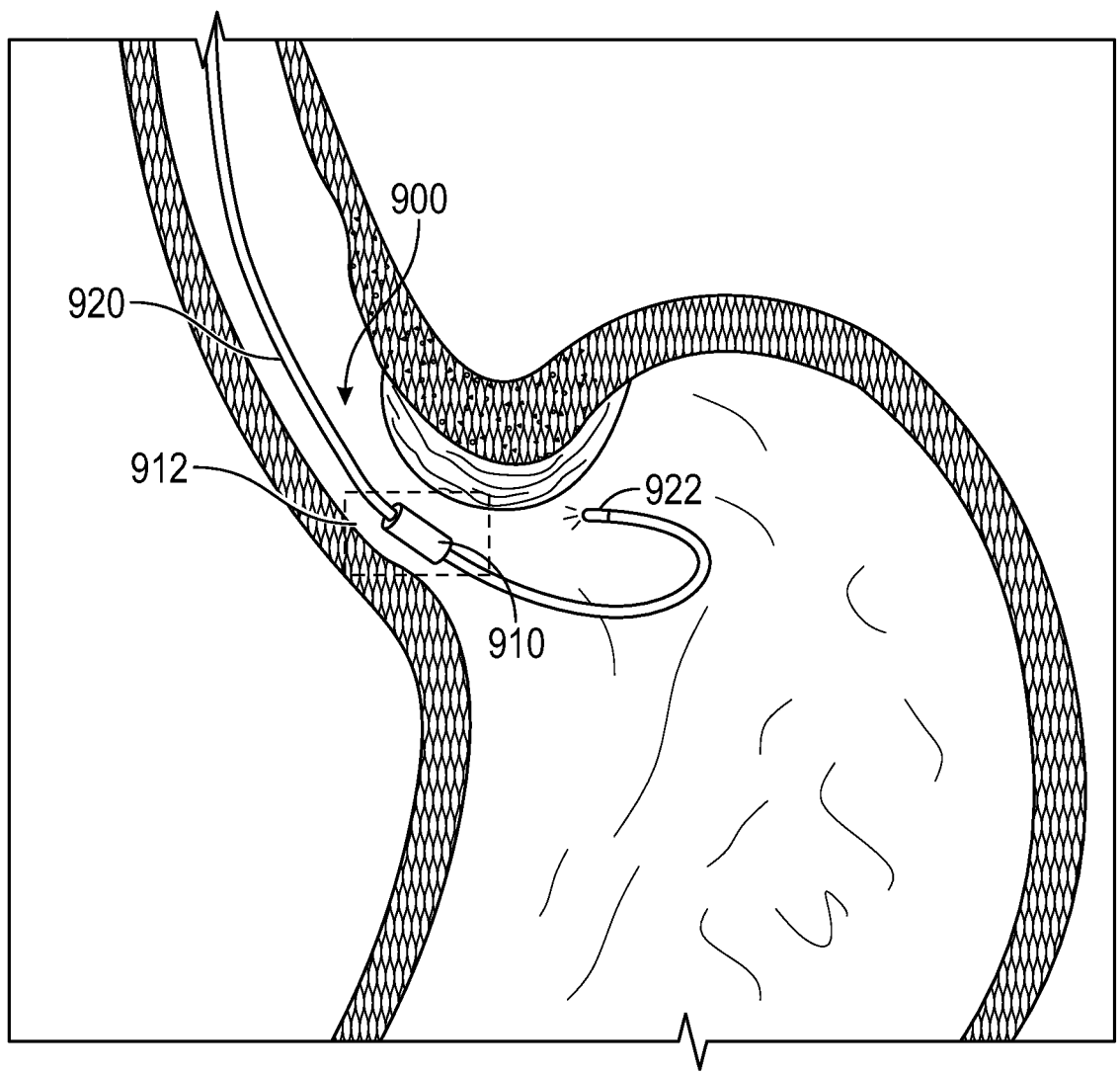
FIG. 34 is a zoomed in environmental view of the gastrointestinal magnetic therapy device of FIG. 32 within a sectioned view of a human gastrointestinal tract.

FIG. 32-34 depict an embodiment of a gastrointestinal "GI" magnetic therapy device 900 and a method of use. The GI device 900 may include an endoscope 920 or steerable rod having a static magnet 910 attached along its length. In some non-limiting embodiments, the magnet 910 may be a ring magnet wrapped around the endoscope 920. In some embodiments, the magnet 910 may be located near a distal end of the endoscope 920. The magnet 910 may be offset a distance from a distal end of the scope which allows the endoscope 920 to coil over for visualizing the magnet 910 in relation to the treatment tissue.

To perform a procedure, the GI device 900 may be inserted into the GI tract either orally or anally, depending on the location of the treatment tissue. Once inserted, the magnet 910 may be approximated to the treatment tissue. The location of the magnet 910 in relating to the treatment tissue may be determined using a camera on the endoscope, medical imaging, or a magnetic sensor such as a MEMS magnetic sensor. Once the magnet 910 is in place, external magnets 912, 914 may be positioned to provide one or more magnetic fields for interaction with the magnetic field of the internal magnet 910. As seen in FIG. 32, a magnet 912 may be placed on a chest of the patient at a position proximate the internal magnet 910, and as seen in FIG. 33, a magnet 914 may be placed on a back of the patient in a position proximate the internal magnet 910. As a result, multiple magnetic fields will be compressed in the healthy tissue surrounding the treatment tissue, thus stimulating the immune system to act on the treatment tissue.

Figure 35:
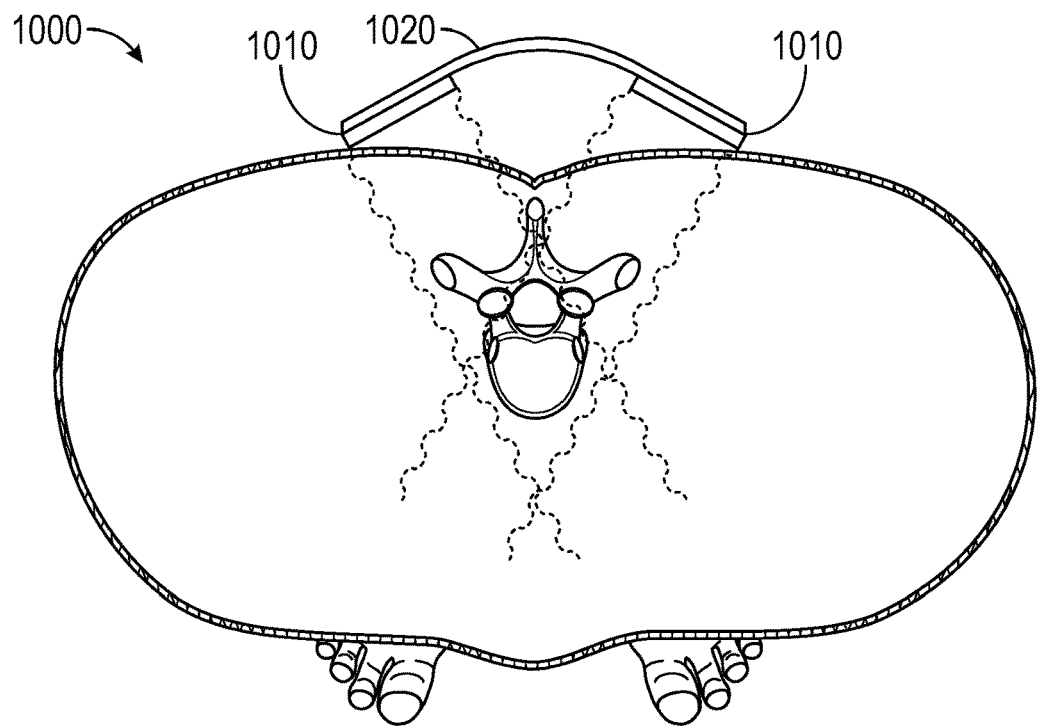
FIG. 35 is an overhead view of a dual magnetic therapy support positioned adjacent a sectioned view of a human body.

FIG. 35 shows an embodiment of a dual magnetic therapy support 1000 which may be used for treating severed nerves. The compressed magnet fields may cause an increase in stem cells in the damaged tissue which may repair the severed nerves. The support 1000, as shown in FIG. 35, may be used to treat a severed spinal cord (S). As seen in FIG. 35, the support 1000 may be designed so the static magnets 1010 are connected to a member 1020 that directs their magnetic fields out towards the spine and slightly inwards to increase the interaction between the strongest parts of the magnetic fields. The support 1000 may be positioned so each magnet is on an opposing side of the spine at the location of the severed spinal cord (S). This location will provide a compressed static magnetic field on the severed ends of the spinal cord nerves and in the surrounding healthy tissue. As a result, the healthy tissue surrounding the injury may draw in stem cells that can be used to repair and reconnect the severed spinal cord.

Figure 36:
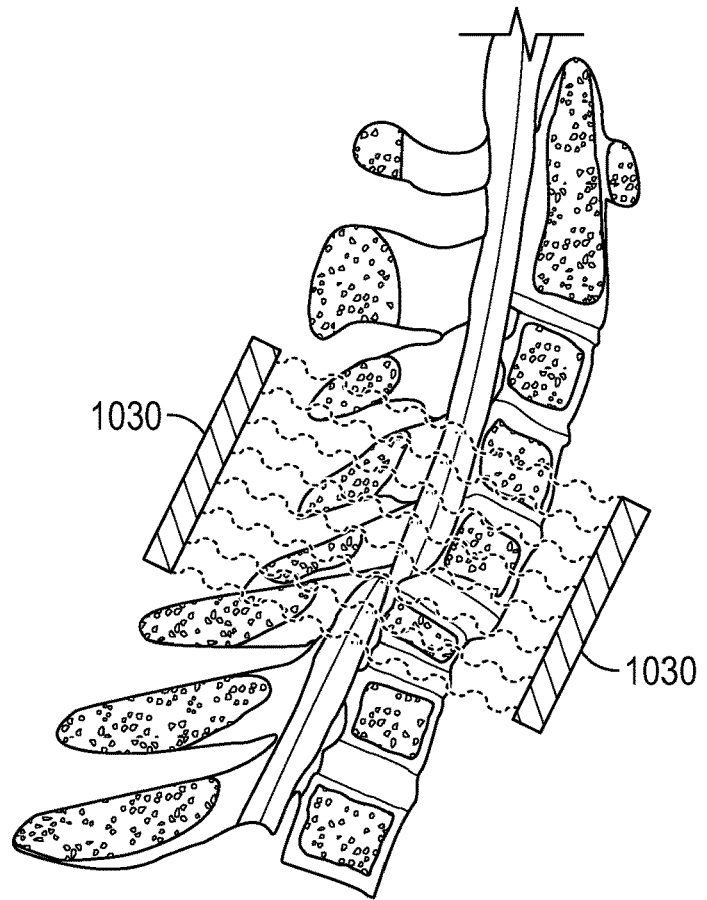
FIG. 36 is an environmental view of a severed spinal cord being exposed to a compressed magnetic field.
Figure 37:
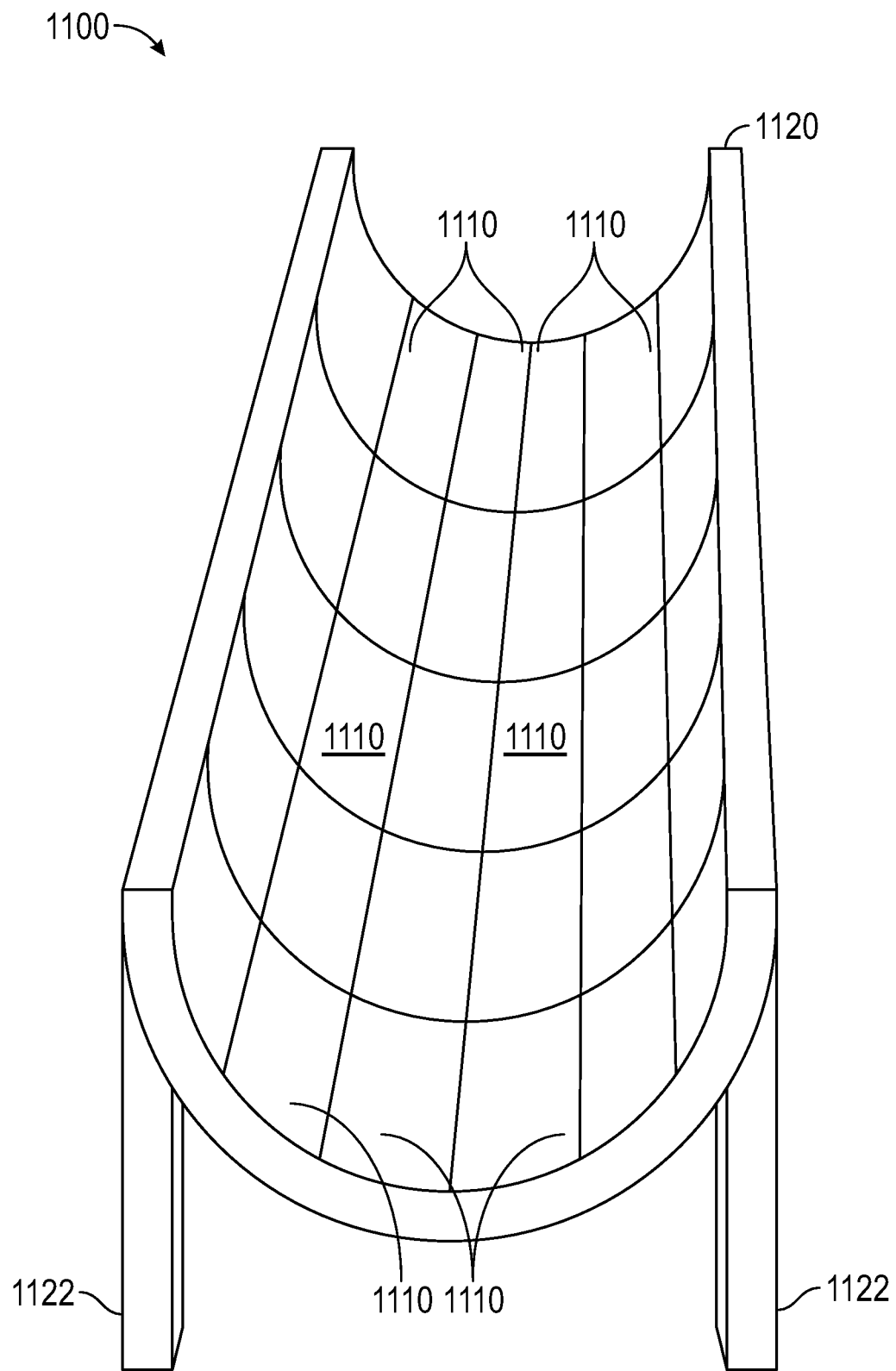
FIG. 37 is a perspective view of a fully body magnetic therapy stand.

FIG. 36 shows an embodiment of spinal column repair method having two or more static magnets 1030 located on the anterior and posterior sides of the spinal column. In some embodiments, one or more of the magnets 1030 may be implanted or inserted into in the patient to decrease the distance between the injured tissue and the magnet 1030, thus increasing the strength of the magnetic field at the location of the damaged tissue.

FIGS. 37-40 show an embodiment of a full body magnetic therapy stand 1100 for exposing a full body to compressed, static magnetic fields. The stand 1100 may include a platform 1120 and multiple legs 1122 raising the platform 1120 from the ground. Multiple magnets 1110 may be dispersed throughout the platform. In some non-limiting embodiments, the magnets 1110 may be attached to the top, bottom, or embedded within the platform 1120. As seen in FIG. 37-40, the platform 1120 is in the shape of a "U" to provide locations for magnets 1110 having fields directed laterally from a raised position. The magnets 1110 may be attached to the platform 1120 with their magnetic fields directed radially inwards to position an interaction of the multiple magnetic fields at the location of the patient within the "U" shaped platform 1120. Strength of the magnetic field may be varied by changing the amount and/or strength of the magnets 1110. In some embodiments, the table may have in the range of 12-100 magnets. The magnets 1110 may be evenly dispersed throughout the table 1100 or may be concentrated at specific areas, such as the torso, for targeted treatments. In some embodiments, the platform 1100 may be made of a soft material or may have a soft covering to aid in user comfort.

Figure 38:
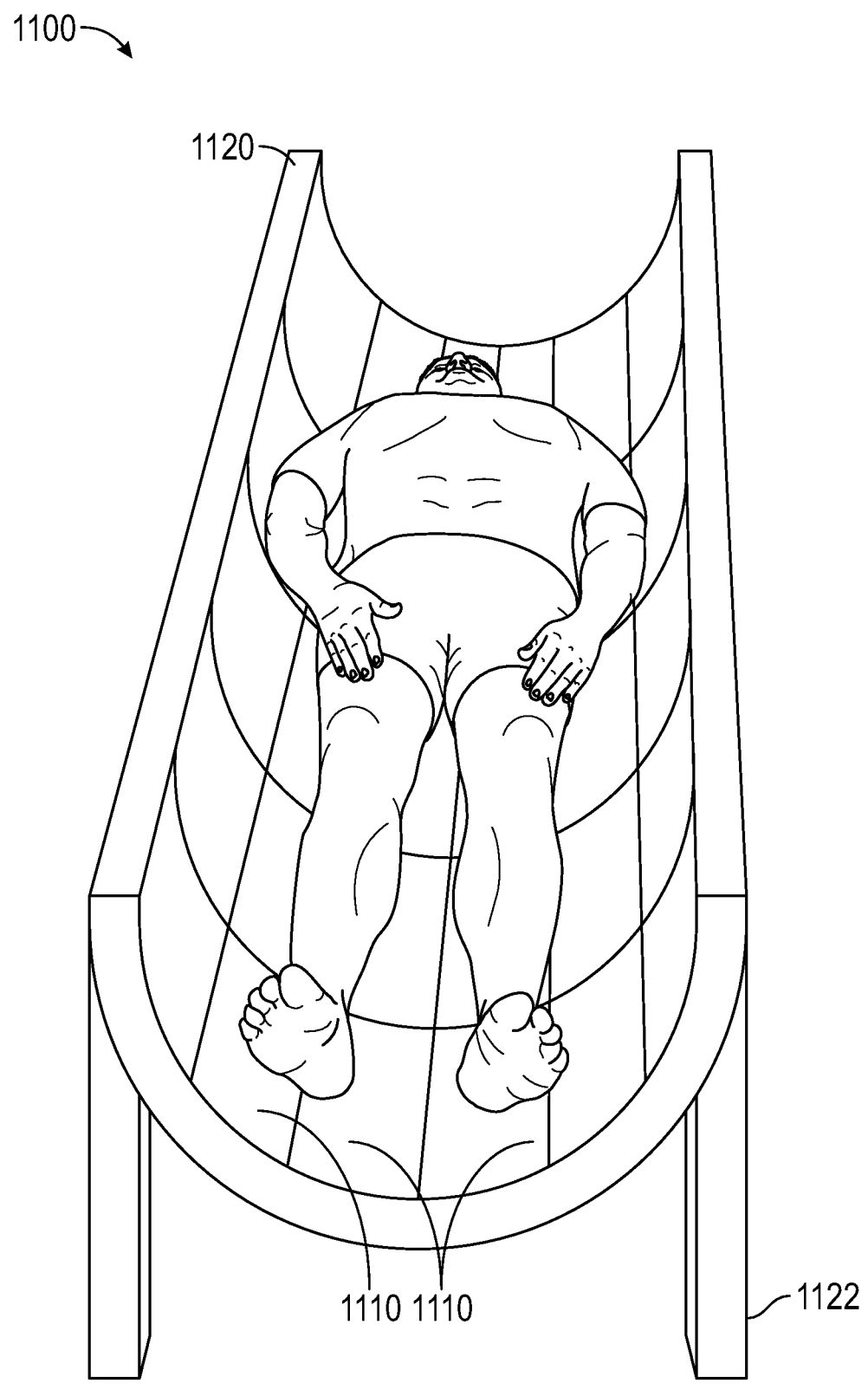
FIGS. 38-40 are environmental views of the fully body magnetic therapy stand of FIG. 37 with a patient in different positions.
Figure 39:
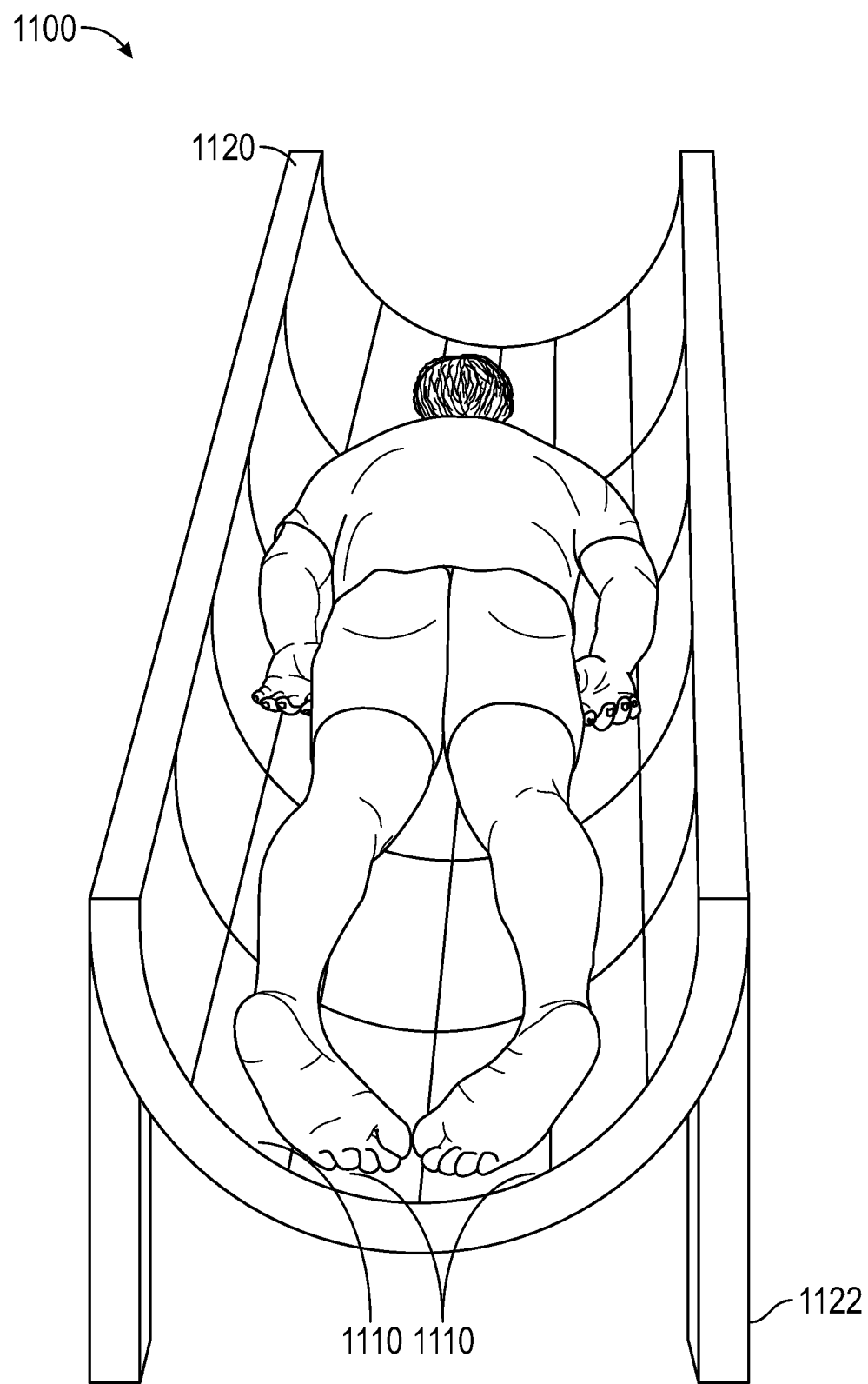
Figure 40:
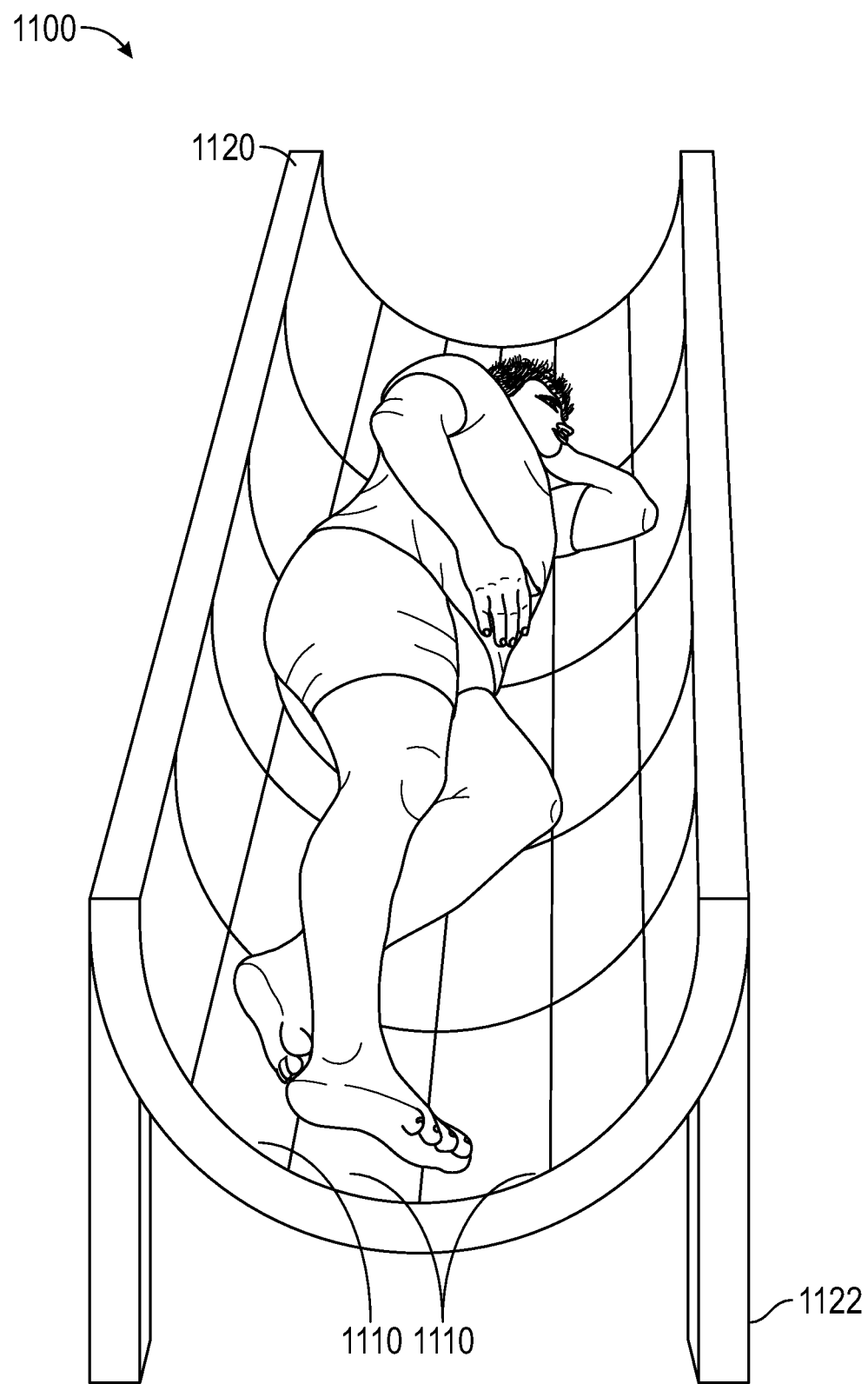

FIGS. 38-40 show a patient being treated by the full body magnetic therapy stand 1100. By laying on the platform 1120, the patient will be exposed to multiple compressed magnetic fields covering their whole body. The magnetic fields will be stronger closer to the platform, so the patient may lie in multiple positions, as seen in FIG. 38-40, to maximize the effect of the compressed magnetic fields to each part of the body. Additionally, changing position of the patient will assure each portion of the body is receiving a similar amount of magnetic therapy. During a magnetic therapy session, a user may lay on each of their back, right side, front, and left side for timed intervals. A non-limiting time interval for each magnetic therapy session may be in the range of 1 hour to 24 hours, and the time interval for each position may be in the range of 15 minutes to 6 hours.

Figure 41A:
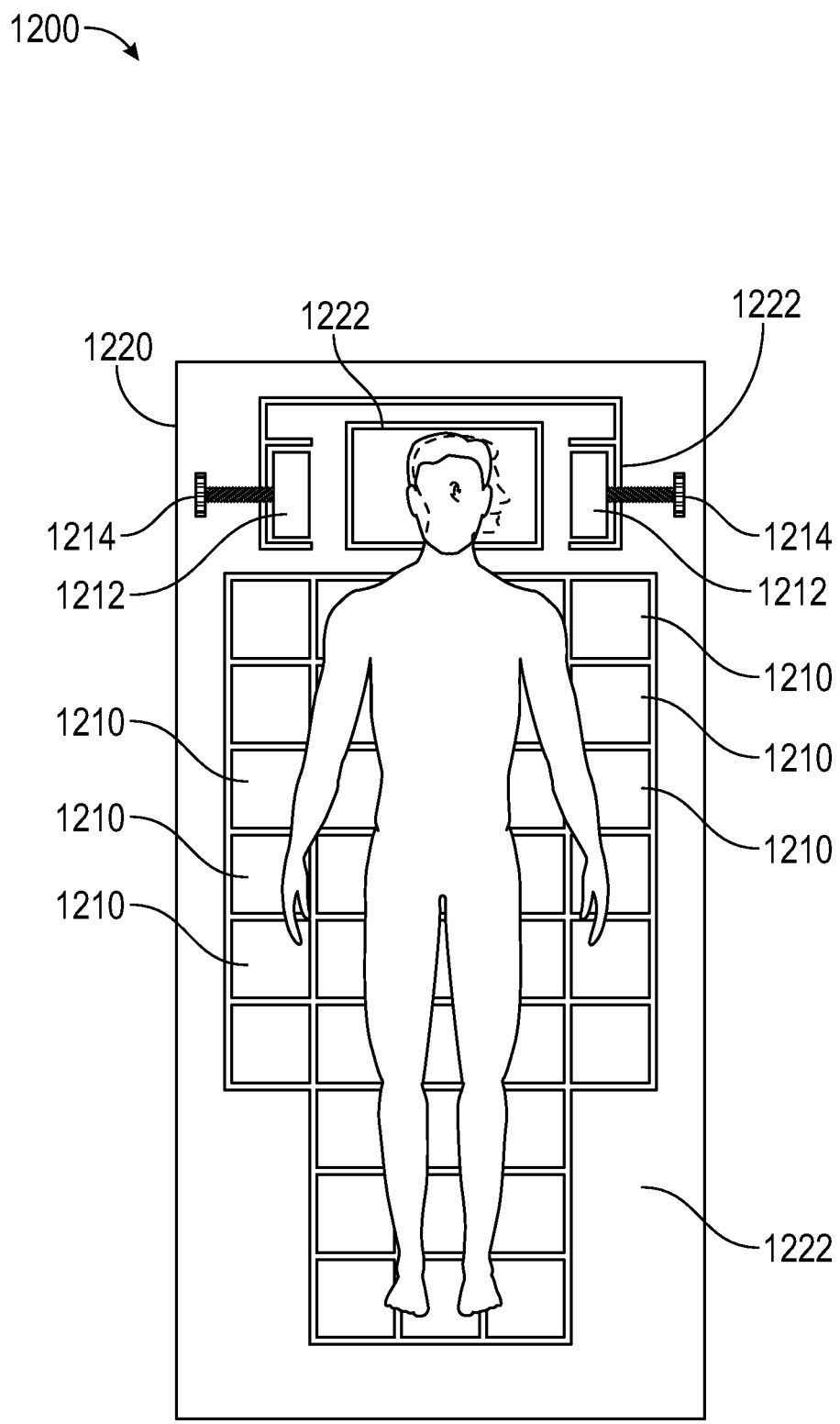
FIG. 41A is an overhead, environmental view of a magnetic bed for use with a fully body magnetic therapy system.
Figure 41B:
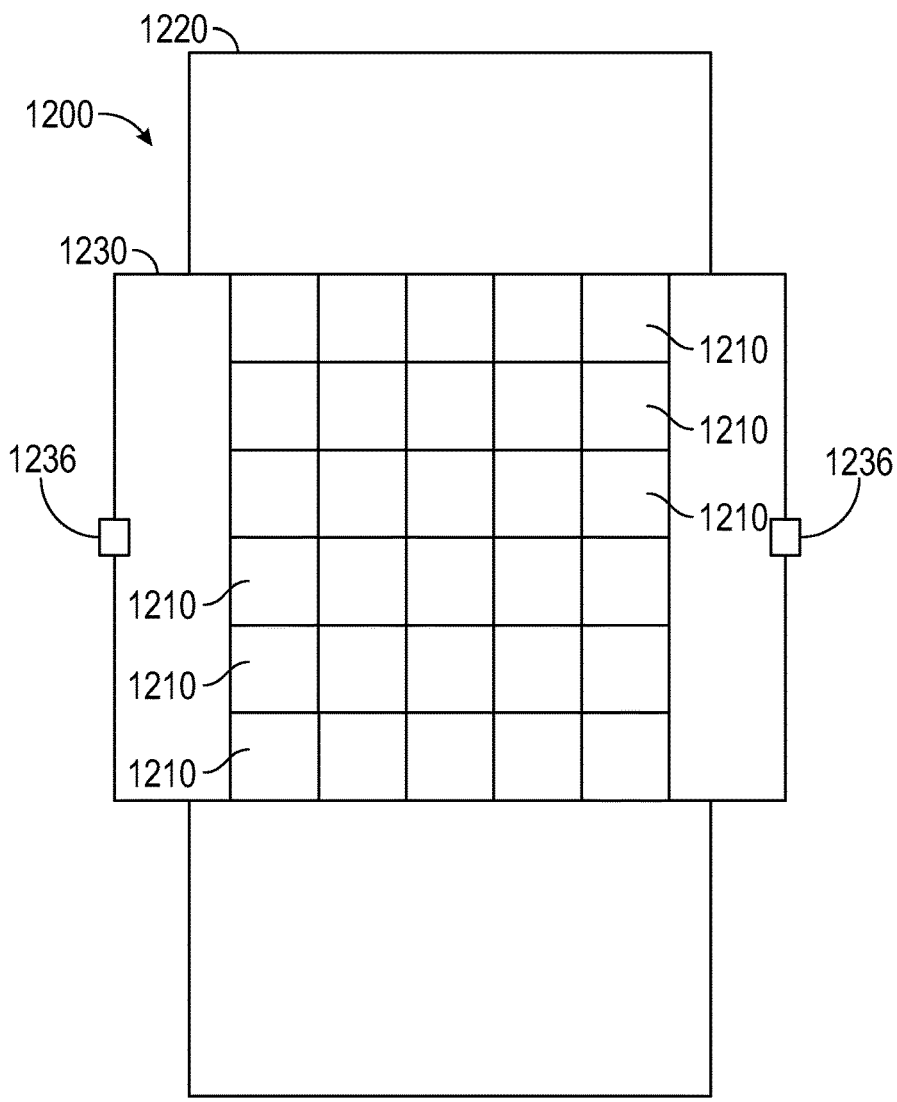
FIG. 41B is a diagram of a full body magnetic therapy system including a magnetic bed and magnetic table.
Figure 41C:
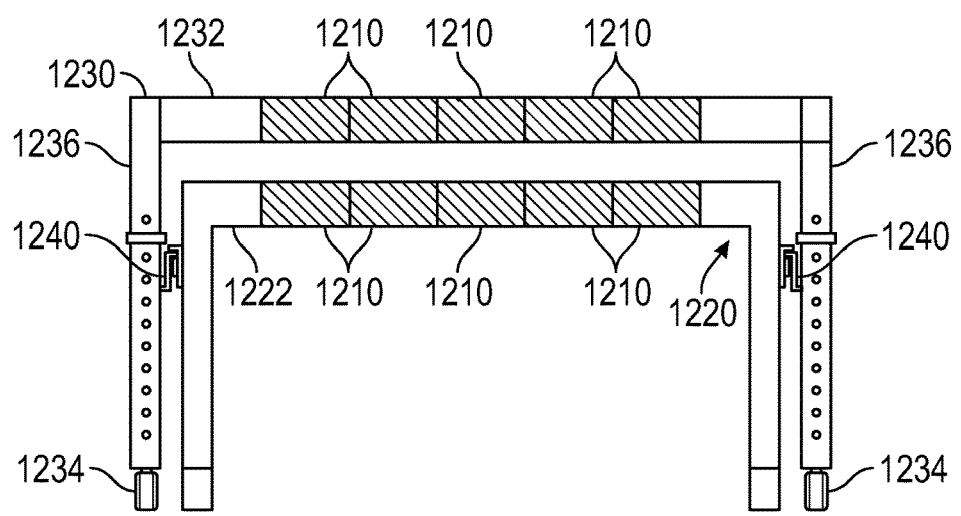
FIG. 41C is a front view of the full body magnetic therapy system of FIG. 41B.

FIGS. 41A-41C show an embodiment of a fully body magnetic therapy system including a magnetic bed 1220 and table 1230. The bed 1220 includes a platform 1222 for supporting a patient. A head portion of the platform may include multiple magnets 1212 for providing compressed magnetic fields in and around the head of the patient. Magnets 1212 positioned to the sides of the patient's head may be raised from the platform 1222 and have their magnetic field directed laterally towards the patient's head. A distance between the magnets 1212 and the patient's head may be adjusted by twisting screws 1214. A magnet 1212 below the patient's head may have its magnetic field directed upwards. As seen in FIG. 41A, a steel encasement may be used to direct the magnetic field of the magnets 1212. Alternatively, in some non-limiting embodiments, the magnets 1212 may be mounting magnets with the strong poles oriented to direct the magnetic field as discussed above. A patient may change the angle of their head to provide different concentrations of magnetic field to different portions of the head and brain.

A middle portion of the platform 1222 may contain an array of magnets 1210 for providing magnetic fields to the body of the patient. Each magnet 1210 may be directed upwards towards a patient lying on the bed. In some non-limiting embodiments, the magnets 1210 may be pivotable so the magnetic fields can be directed as desired by a practitioner. For example, magnets directed at areas not requiring treatment may be directed downwards. A density and amount of the magnets 1210 may be determined based on the strength of the individual magnets 1210, the desired amount of individual magnetic fields, and the desired spacing between magnetic fields. In some non-limiting embodiments, the entire platform 1222 may be covered by the array of magnets 1210. In some non-limiting embodiments, the platform 1222 may support in the range of 20 to 100 magnets 1210 of the same or different sizes and strengths. In some non-limiting embodiments, densities of the magnets 1210 may be varied through the platform 1222 to treat conditions at specific parts of the body.

FIGS. 41B and 41C show a magnetic table 1230 for use with the magnetic bed 1220. The table 1230 may be designed to contain magnets 1210 having their magnetic fields direct downwards to interact with the magnetic fields directed upwards from the bed. As a result, the portions of a patient sandwiched between the bed 1220 and table 1230 will be exposed to multiple compressed magnetic fields originating from above and below the patient. The table 1230 may include an upper platform 1232 containing an array of magnets 1210 and at least one adjustable support 1236. In some non-limiting embodiments, the supports 1236 may be height adjustable to allow for the height of the upper platform 1222 to be adjusted based on a thickness of the patient. Height adjustability allows a practitioner to maximize the strength of the magnetic fields in which the patient is exposed since the strength of the magnetic fields increases with proximity to the magnets 1210. Any adjustment mechanism known in the art for moving a platform up and down may be used, for example a locking telescopic pole. The bottom of each support 1236 may contain wheels 1234 to allow the practitioner to move the array of magnets 1210 over different portions of the patient's body and/or align the magnets 1210 of the table 1230 with the magnets 1210 of the bed 1220. Tracks 1240 may run along the length of each side of the bed 1220. The table 1230 may be connected to the tracks 1240 to prevent any instability that may be caused by the repulsive or attractive magnetic forces between the magnets 1210 on the table 1230 and bed 1220. The portion of the patient's body directly in between the bed 1220 and table 1230 will be exposed to the maximum strength compressed magnetic fields. The magnets 1210 of the table may be arrange in an array matching the magnets of the bed 1220, but with the magnetic fields being directed downwards. In some embodiments, the array of magnets 1210 on the bed 1220 may share width and/or length dimension with the array of magnets 1210 on the table 1230. In some non-limiting embodiments, the table 1230 may support an array of magnets 1210 having between 20 and 100 magnets. The amount of magnets 1210 may be varied based on the size and strength of magnets used.

Figure 42A:
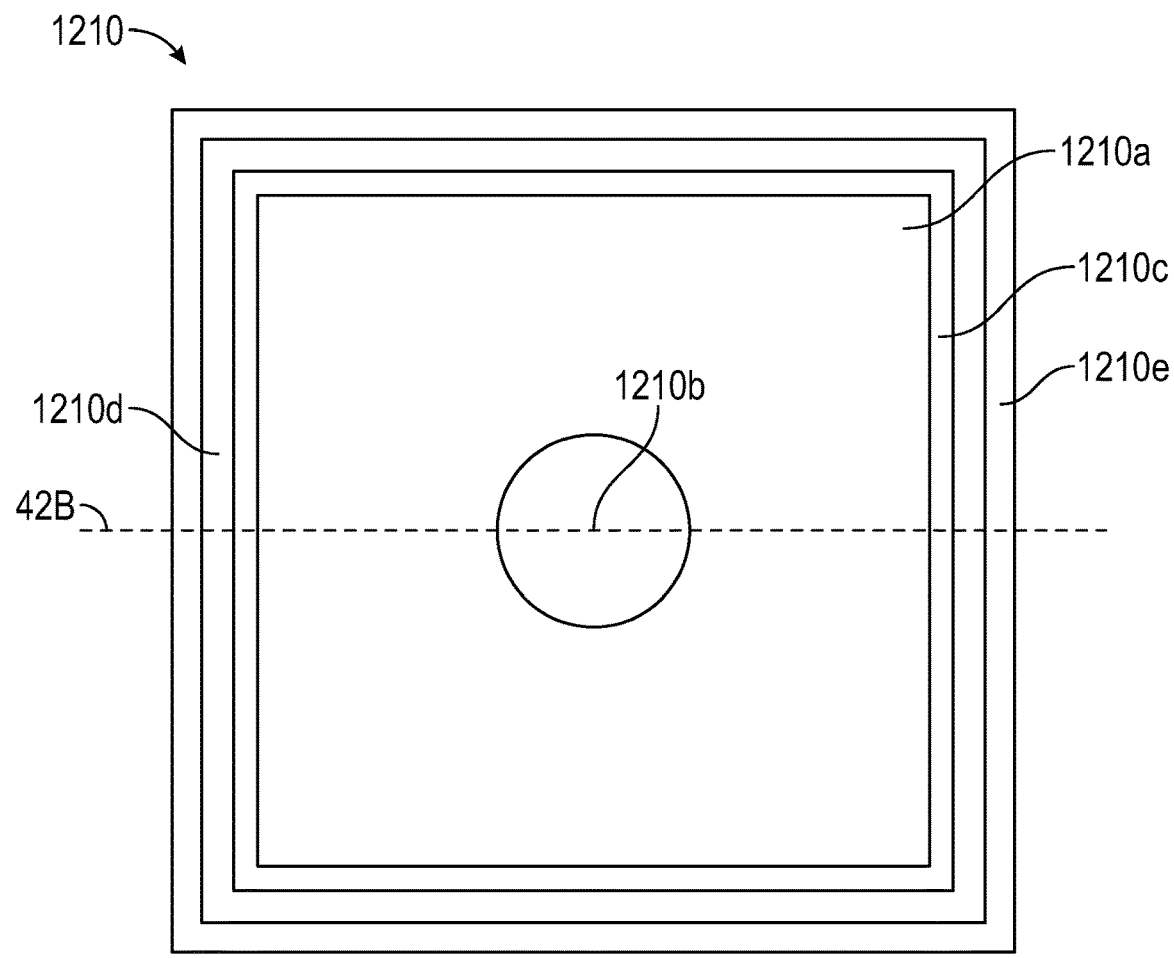
FIG. 42A is an overhead view of a mounting magnet.
Figure 42B:
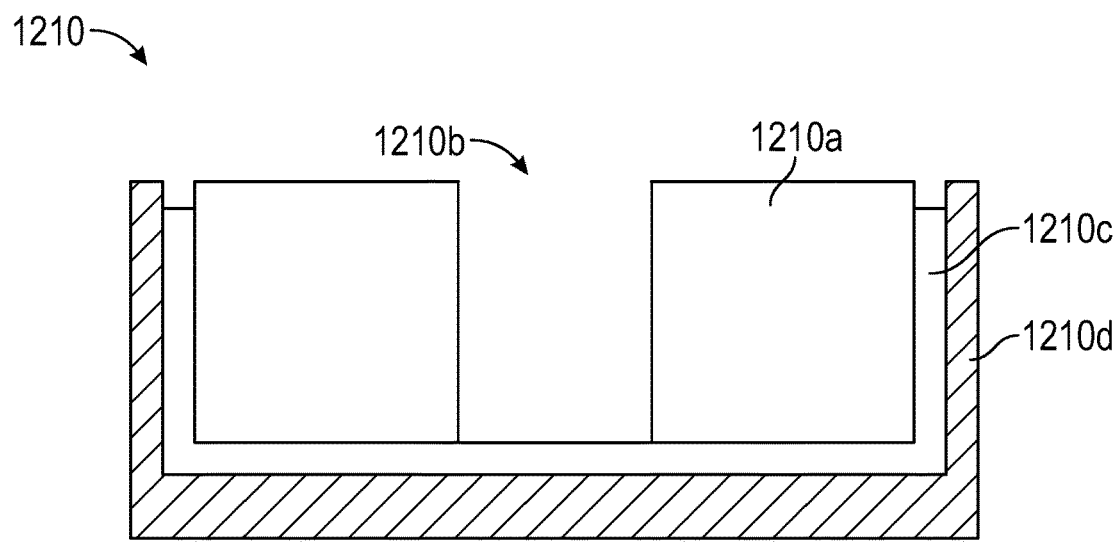
FIG. 42B is a sectioned view of the mounting magnet of FIG. 42A along line 42B.

FIGS. 42A and 42B show a non-limiting example of a magnet 1210 that may be used on the magnetic bed 1220, the magnetic table 1230, or any magnetic device described herein. In some embodiments, the magnetic material 1210a may be a grade N42-N55 neodymium ring magnet. The outer shape of the magnetic material 1210a may be square to allow for a higher density of magnetic material 1210a in the arrays. Each magnetic material 1220a component in the arrays may be encased in steel 1210d with a spacer 1210c between the magnet and the steel to produce a mounting magnet. A metallic shield 1210e may be provided on the outside of the metal encasement to provide further deflection of the magnetic field towards the strong side of the magnet 1210. In some non-limiting embodiments, the magnets 1210 may have a width and length in the range of 2 to 10 inches, a thickness in the range of 0.25 to 2 inches, and/or a central opening 1210b in the range of 0.25 to 2 inches. An upper portion of the central opening 1210b may be fileted for accepting a countersunk bolt.

Figure 43A:
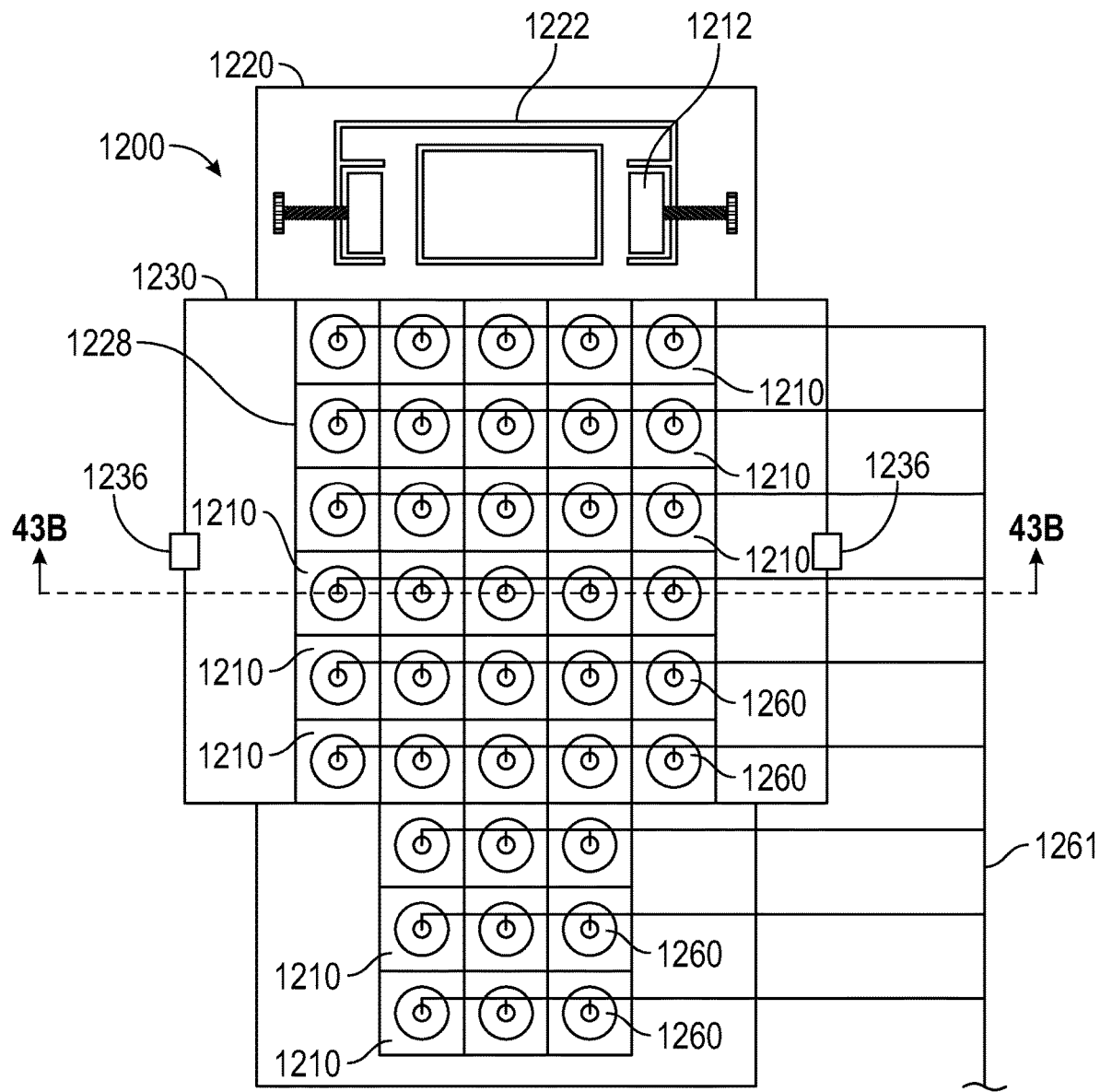
FIG. 43A is an overhead view of an embodiment of a full body magnetic therapy system including a magnetic bed and magnetic table.
Figure 43B:
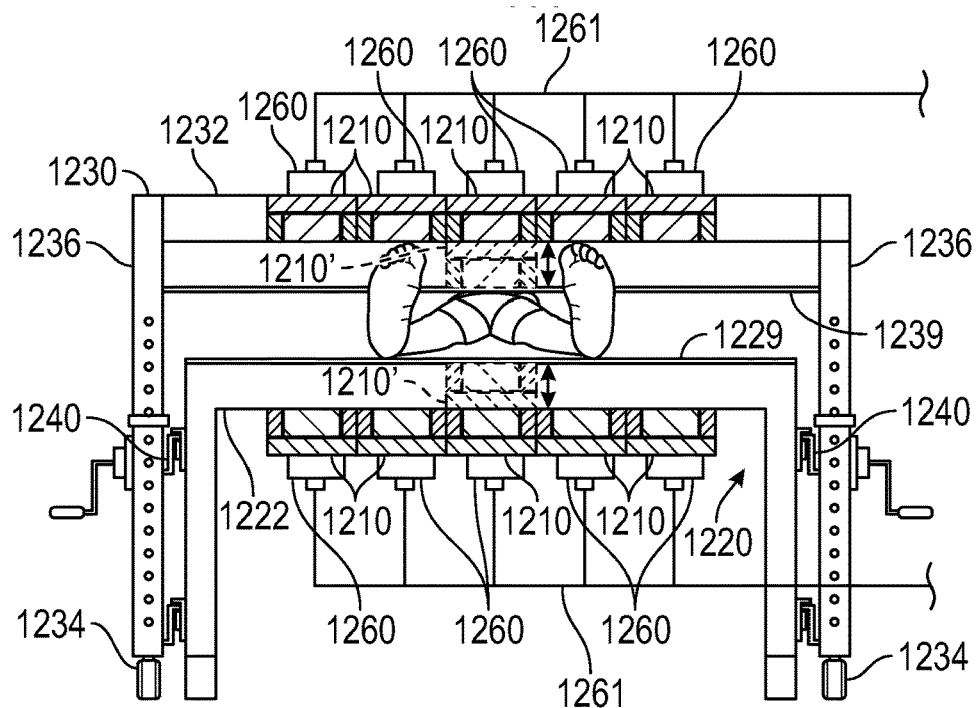
FIG. 43B is a section view of the full body magnetic therapy system of FIG. 43A taken along line 43B.
Figure 43C:
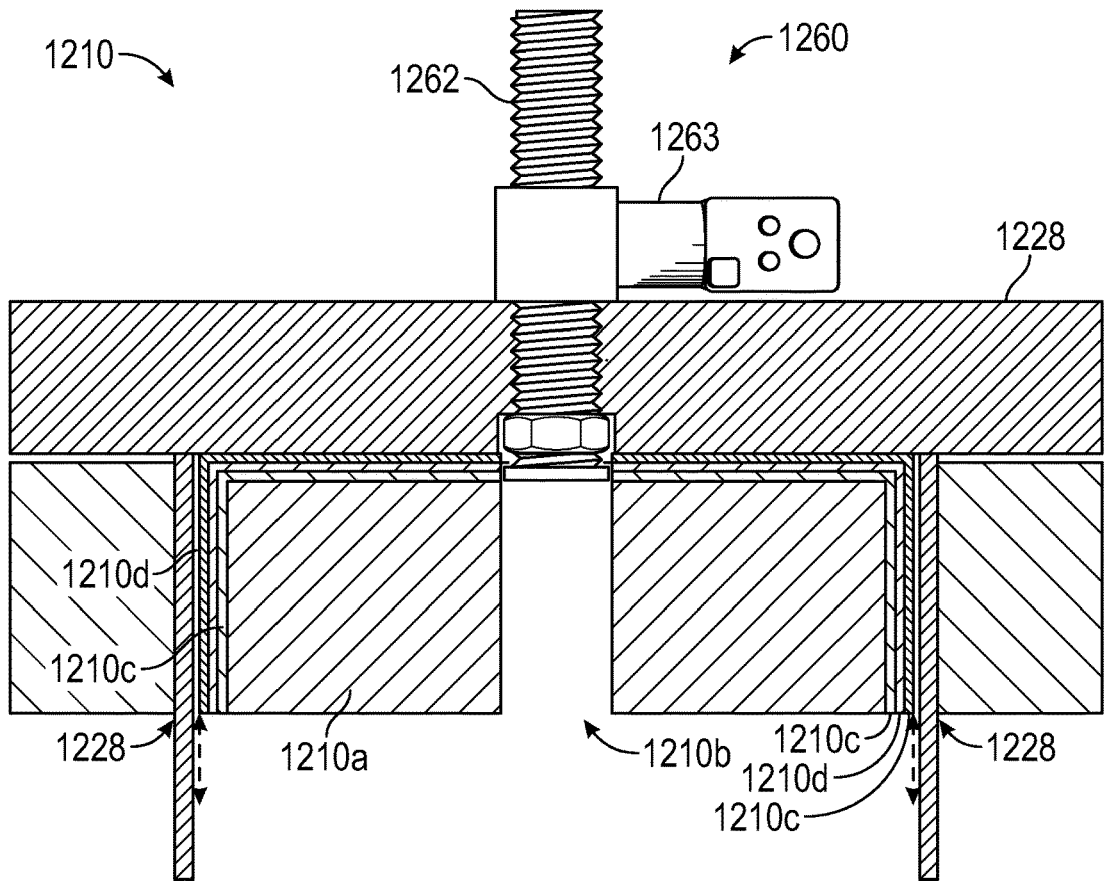
FIG. 43C is a zoomed-in, sectioned view of the full body magnetic therapy system of FIG. 43A taken along line 43B, detailing a magnet and its respective actuator.

FIGS. 43A-43C show an embodiment of a fully body magnetic therapy system including a magnetic bed 1220 and table 1230 which have extendable magnets 1210. Each magnet 1210 may be individually attached to an actuator 1260 that may move the magnet 1210 towards the patient to provide treatment, or further away from the patient for areas that do not need treatment. As shown in FIG. 43B, when each magnet 1210 is retracted, a patient facing surface of the magnet 1210 may rest 3 to 12 inches from the patient. Using the actuator 1260, selected magnets 1210' may be moved closer to the patient for providing a stronger magnetic field within the patient. Any magnetic therapy device within the scope of this disclosure may be used with the magnetic therapy bed to expose a user to additional static magnetic fields at specific locations.

In some embodiments, a non-magnetic frame 1228 may provide channels to guide each magnet 1210 through its range of motion. For example, the frame 1228 may be six inches thick for a system that can actuate the magnets 1210 six inches. Each of the actuators 1260 may be secured to the side of the frame 1228 opposite the patient. A non-magnetic sheet 1229 may be positioned on the upper side of the platform 1220 to provide a flat surface for supporting the patient.

FIG. 43C shows a cross-section of a single magnet 1210 and its attached actuator 1260. A body of the actuator 1263 may be threadedly engaged with a threaded rod 1262 that is attached to the magnet's steel encasement 1210d. By spinning the threaded rod 1262, the actuator 1260 is able to move the magnet 1210 up and down in the channel formed by the frame 1228. In some embodiments, the magnets 1210 may be actuated by other linear actuators known in the art.

In use, a practitioner may determine a location on a patient that requires magnetic treatment and which corresponding magnets 1210 magnets to approximate to the patient. Additionally, the practitioner may also determine an ideal distance between the patient and each magnet 1210, which will dictate the strength of the magnetic fields to which the patient is exposed. In some embodiment, a computer program may be used to determine which magnets 1210 to actuate and how far to actuate the magnets 1210 based on an algorithm inputting imaging data. For example, imaging data providing the size and location of the target tissue may be inputted into the program, and the program may select magnets 1210 and the magnitude of their movement based on the data. In some embodiments, the algorithm may use feedback from a polarized neutron imaging device. The polarized neutron imaging device is capable of detecting magnetic fields within an object. Accordingly, the algorithm may be used the known position of the target tissue, determined by medical imagining such as CT, MRI, EEG, and QEEG, and may adjust the magnets until the magnetic fields are optimally positioned based on the feedback provided by the polarized neutron imaging device. In some scenarios, optimal position may be a maximum magnitude of compressed magnetic fields in the target tissue or a maximum magnitude of compressed magnetic fields in the healthy tissue immediately surrounding the target tissue.

As seen in FIGS. 43A and 43B each actuator 1260 may be connected to an array of power and data lines 1261, with an individual line for each actuator 1260. Accordingly, the actuation of each magnet 1210 may be individually controlled by a computer in communication with the data lines 1261.

Figure 43D:
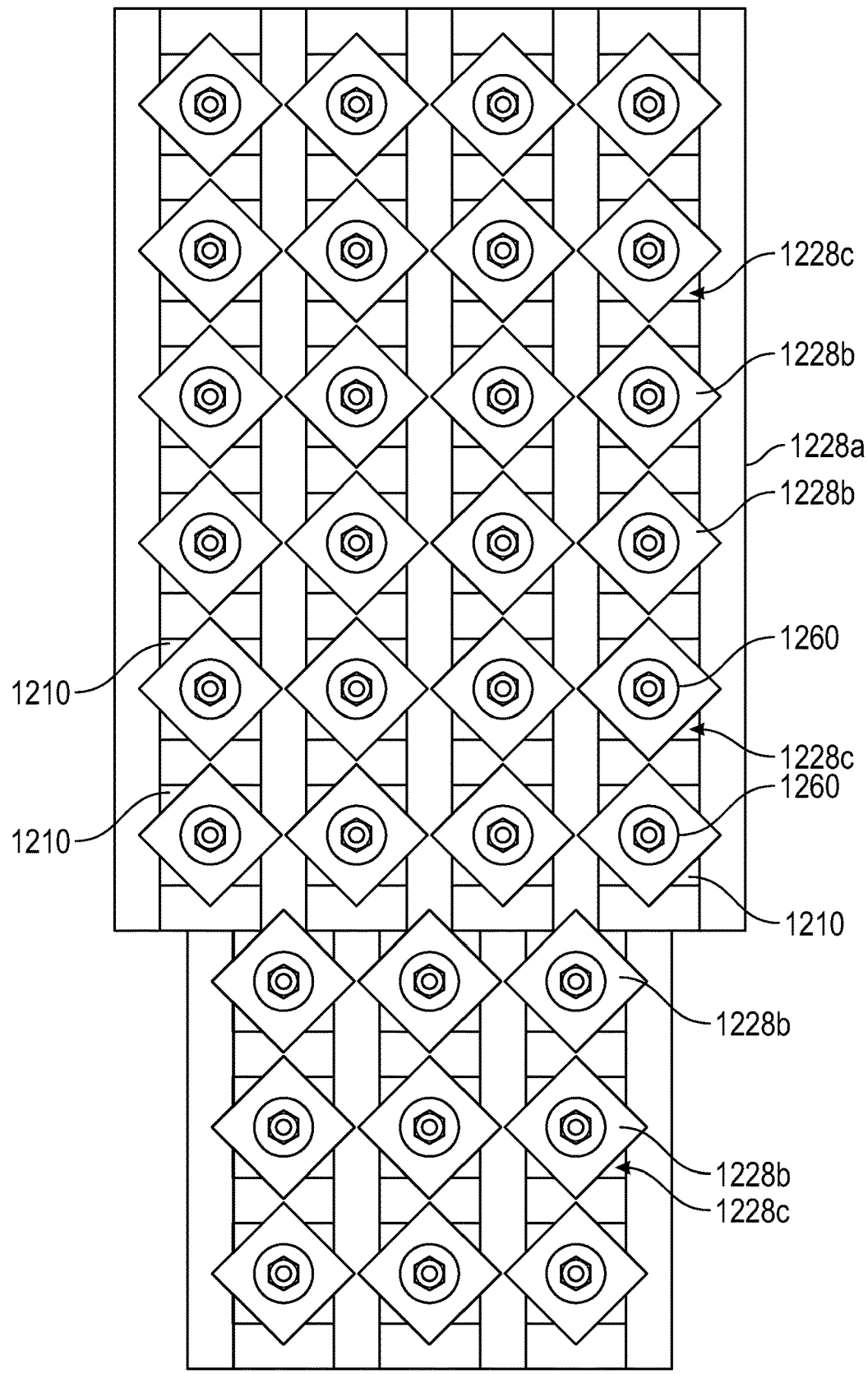
FIG. 43D is a complete frame assembly where all of the magnets components are attached.

FIG. 43D shows and embodiment of a frame 1228, including actuators 1260 and magnets 1210, that may be used in the magnetic platform 1220. When creating the frame 1228, channels 1228c, for guiding the magnets 1210, may be cut out using a water jet or similar cutting mechanism to form the base 1228a. The cutouts 1228b may then be rotated 45 degrees and welded to the side of the base 1228a opposite the patient supporting side for supporting the actuators 1260. Similar construction may be used to create the magnetic array of the table 1230.

Figure 44A:
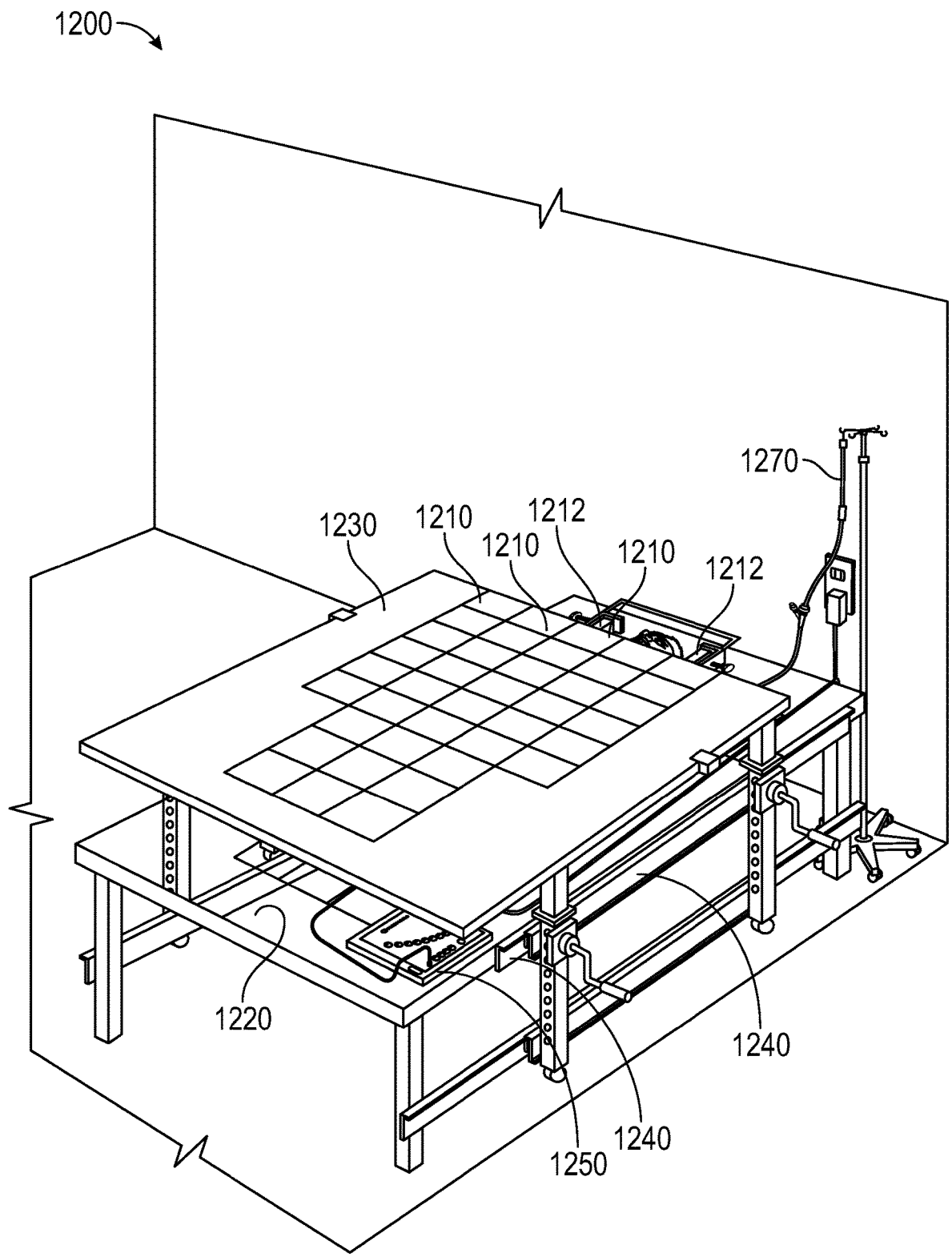
FIG. 44A is an environmental perspective view of an embodiment of a full body magnetic therapy system.
Figure 44B:
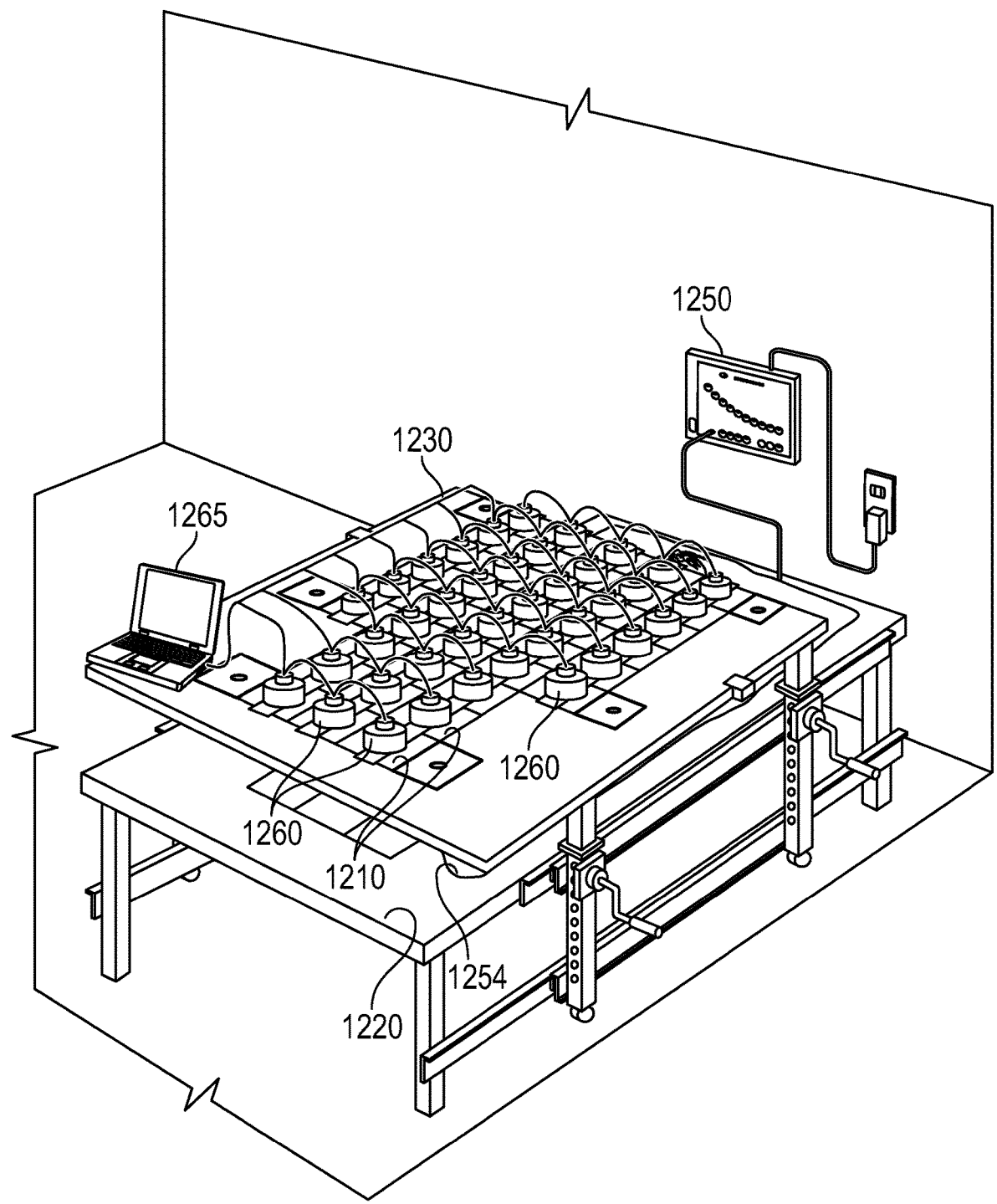
FIG. 44B is an environmental perspective view of an embodiment of a full body magnetic therapy system.

FIGS. 44A and 44B show the magnetic bed 1220 and table 1230 in use. In FIG. 44A, the magnetic bed 1220 and table 1230 combination are primarily providing magnetic therapy to the patient's torso since that is the portion of the body between the two arrays of magnets 1210. This configuration may be used when the treatment tissue is in the patient's torso or to treat cancer cells flowing through the patient's circulatory or lymphatic systems. In some embodiments, a pulsed electromagnetic field generator 1250, such as a Bemer 3000™, may be attached to the patient during the magnetic therapy. A pulse frequency of the pulsed electromagnetic field generator 1250 may be in the range of 0.05 Hz to 963 Hz. In some embodiments, the frequency may be 10 Hz or 33 Hz as these frequencies have been found to produce a greater therapeutic effect than many other frequencies. The static magnetic fields caused by the arrays of magnets 1210 may cause the red blood cells of the patient to form rouleaues which are stacks of red blood cells. The stacked red blood cells do not circulate as well as individual cells and therefore may affect blood flow. Applying a pulsed electric field to the patient's circulatory system may prevent or at least mitigate the rouleau formation, thus increasing circulation. The electrode 1252 of the pulsed electromagnetic field generator may be placed at any location on the skin of the patients. In some embodiments, the electrode may be a mat that the patient lays upon. A pulsed electric field generator, such as the Bemer 3000 can be used with any embodiment of a magnetic therapy device discussed herein. A pulsed electric field generator may be used with any Alzheimer's treatment discussed herein.

FIG. 44B shows the magnetic bed 1220 and table 1230 with actuated magnets 1210. A computing device 1265 may be used to control the actuators 1260, as discussed above. When providing treatment, the patient may be placed on the platform 1220 and the table 1230 may be lowered to a position adjacent the patient. The practitioner may them lower selected magnets 1210, using the computing device 1265, to provide targeted magnetic treatment to the patient. The computing device 1265 may be any computing device having a user interface such as a laptop, tablet, or cell phone. In some embodiments, the computing device 1265 may communicate with the actuators 1260 via a wireless connection, such as Wifi, Bluetooth, or cellular communications.

In addition to the magnetic therapy, stem cells may be injected into the patient's to enhance the full tissue regrowth. The compressed magnetic fields provide increased stem cell activity indicated by the full tissue regrowth discussed below in Examples 2 and 3. The process of regrowth may be enhanced by using an injection port 1270 to provide additional stem cells.

Figure 45:
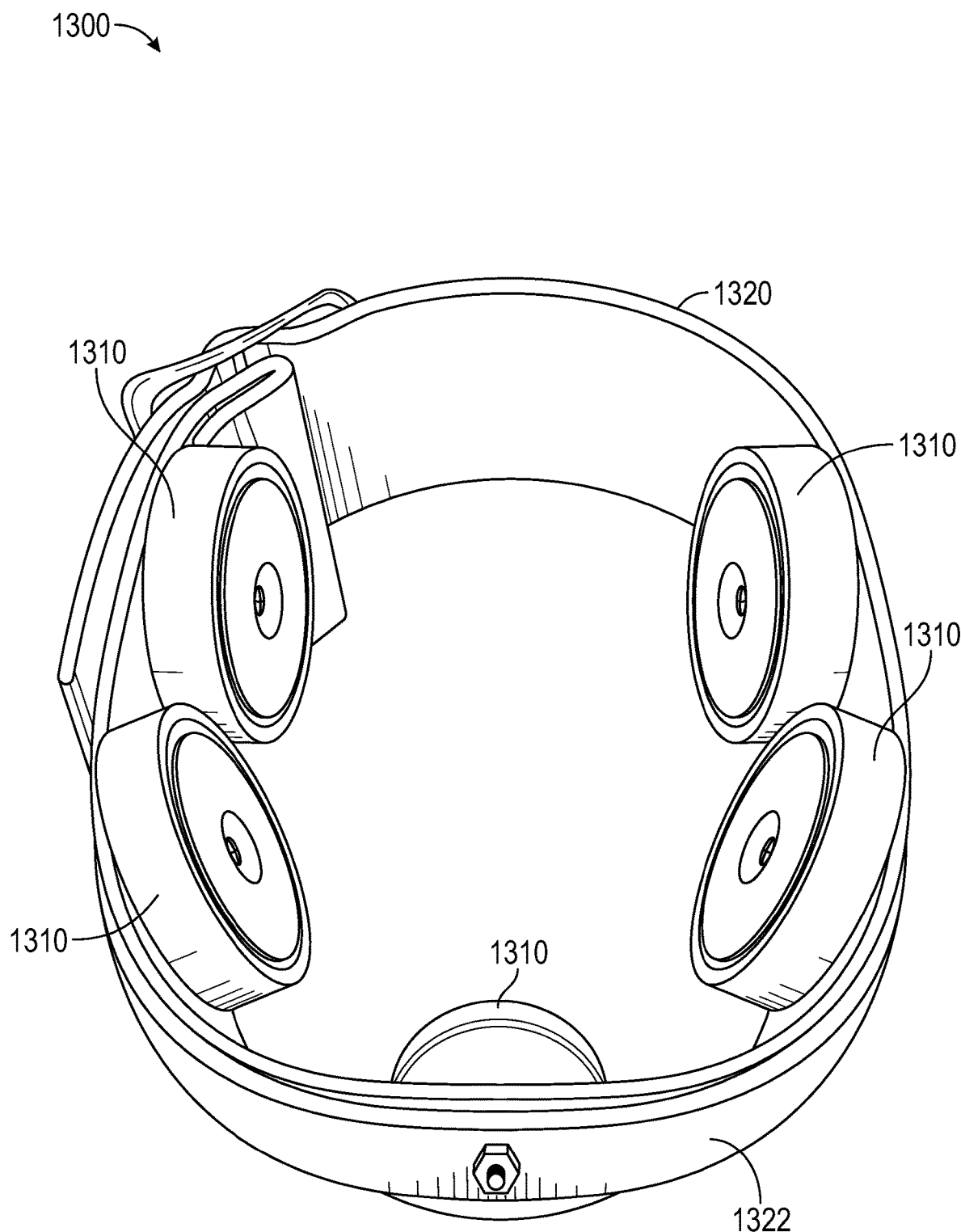
FIG. 45 is a perspective view of a magnetic therapy collar.
Figure 46:
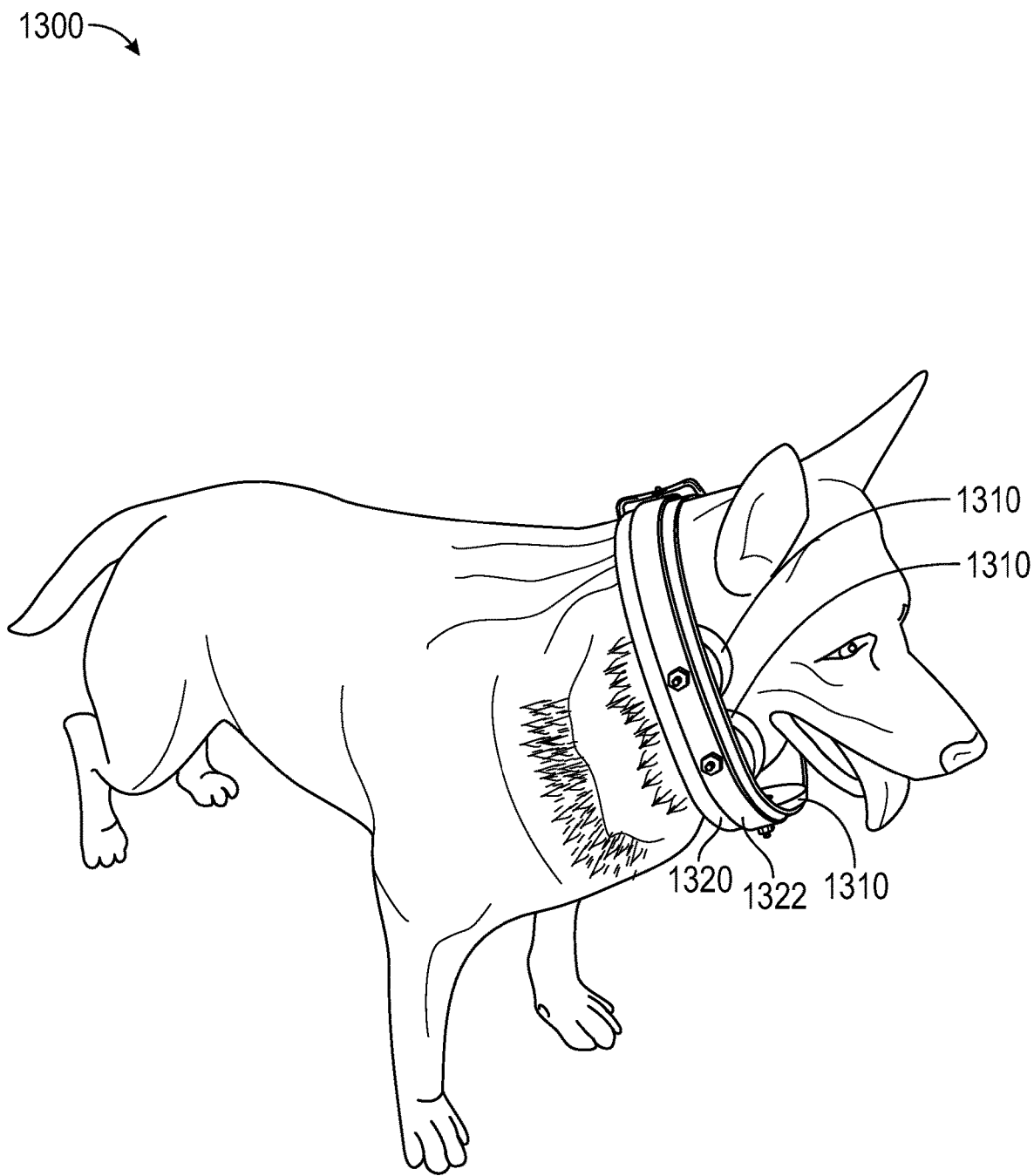
FIG. 46 is an environmental, perspective view of the magnetic therapy collar of FIG. 45.

FIGS. 45 and 46 show an embodiment of a magnetic therapy collar 1300. The magnetic therapy collar 1300 may include five static magnets 1310, two on each of the left and right sides of the collar and one on the bottom. Each of the magnets 1310 may be a mounting magnet with the strong side directed inwards. The collar 1300 may include an adjustable strap 1320 and a mounting member 1322 which extends around a circumference of the adjustable strap 1320 to hold the magnets 1310 at a generally rigid configuration. For example, in some non-limiting embodiments, the mounting member 1322 may be a ¾ inch by ⅛ inch piece of flat aluminum bar. Holes may be formed through the strap 1320 and mounting member 1322 for accepting bolts that secure the magnets 1310. The mounting member 1322, strap 1320, and magnets 1310 may be secured together by the bolts of the magnets 1210. In some embodiments, securement may be provided by attachment mechanisms known in the art such as adhesives or rivets. A circumference of the strap 1320 may be adjustable and may be also disconnectable using mechanisms known in the art such as a belt buckle or hook and loop fasteners.

As seen in FIG. 46, the magnetic therapy collar 1300 may be sized and shaped to loosely hang on the dog's neck. The loose attachment may allow the magnets 1310 to shift positions on the neck when the dog moves or changes position resulting in a larger exposure of the condensed magnetic field. The magnets 1310 may be positioned based on the location of the treatment tissue. For example, a tumor on the bottom of the dog's neck may be treated by three magnets 1310 positioned at the bottom of the collar 1300. In some non-limiting embodiments, the number of magnets 1310 on the collar 1300 may be in the range of 2 to 20.

Figure 47:
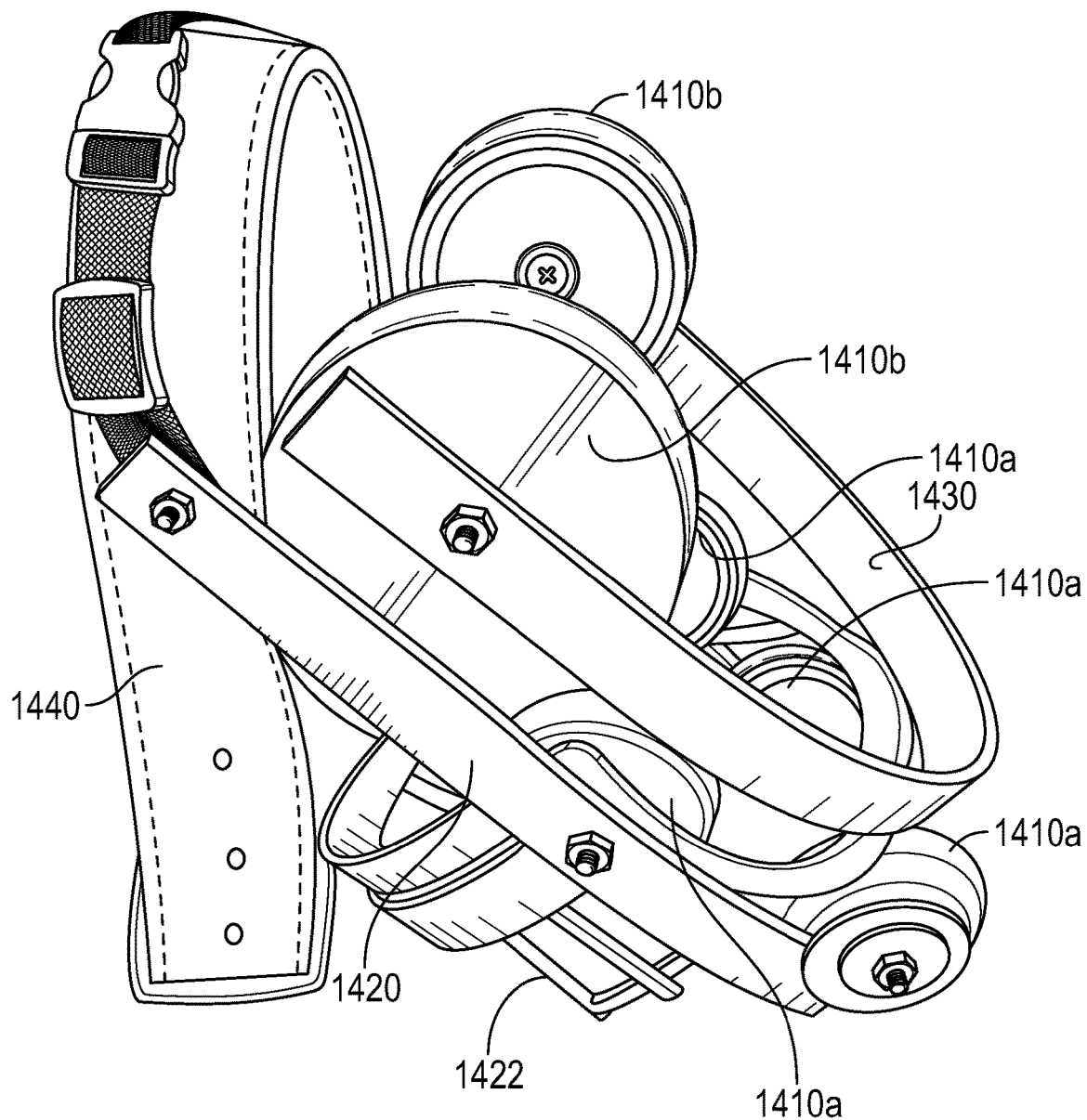
FIG. 47 is a perspective view of second embodiments of a magnetic therapy muzzle.
Figure 48:
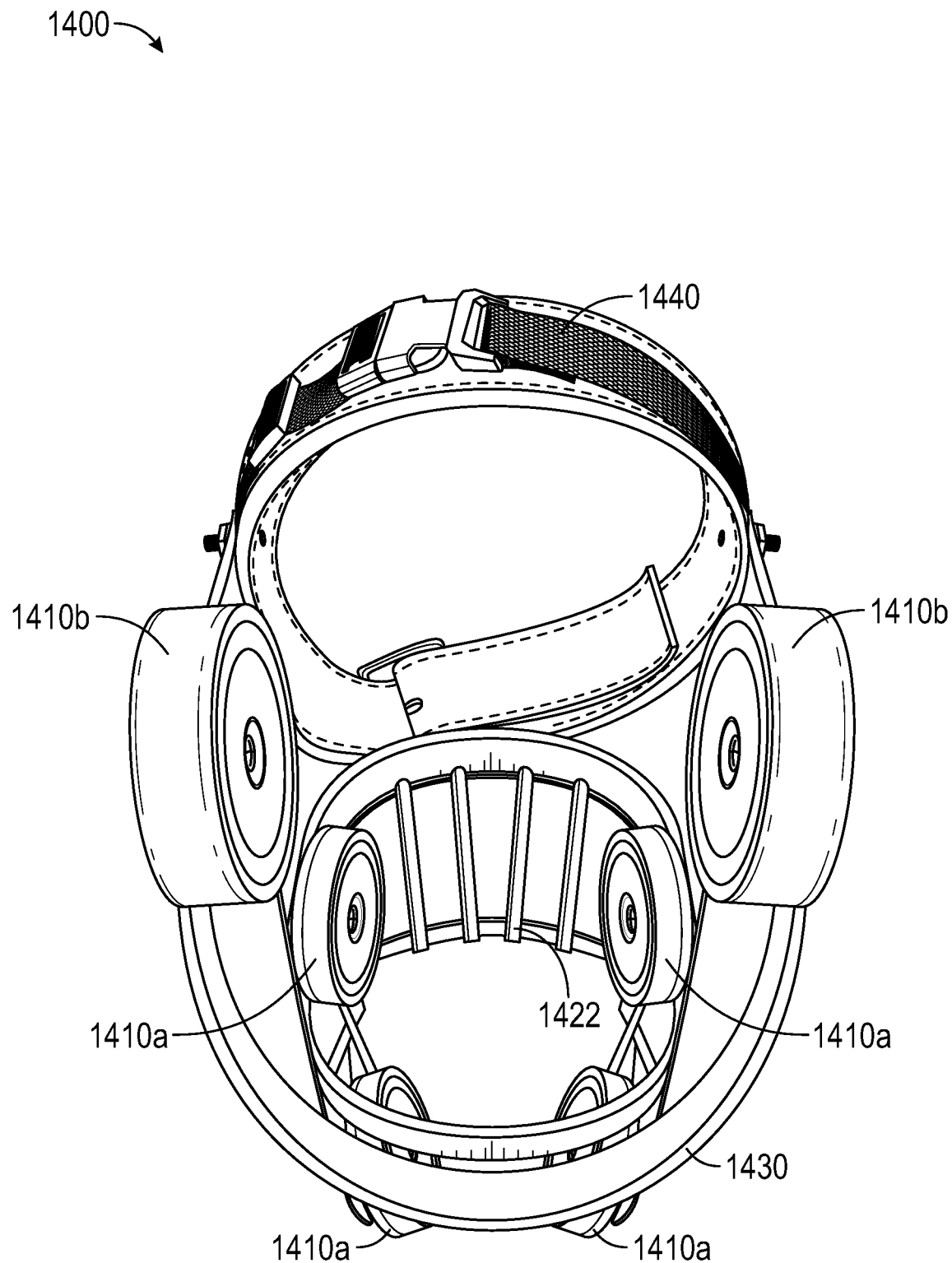
FIG. 48 is an overhead view of the magnetic therapy muzzle of FIG. 47.
Figure 49:
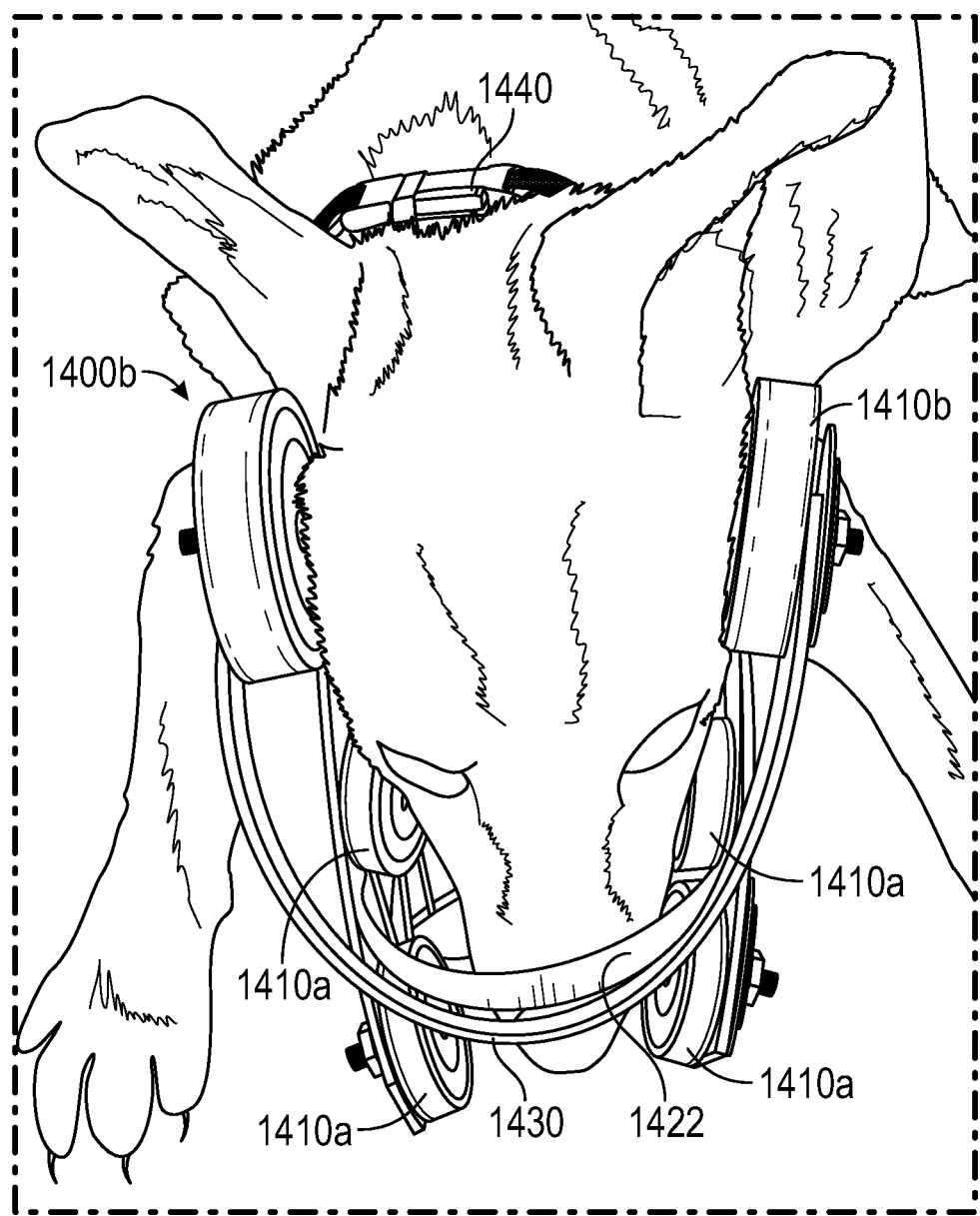
FIG. 49 is an environmental view of the magnetic therapy muzzle of FIG. 47.

FIGS. 47-49 show an embodiment of a magnetic muzzle 1400. The magnetic muzzle 1400 may include an adjustable collar 1400 pivotally connected to two jaw rods 1420 which are designed extend down opposing side of a snouted animal's jaw. A muzzle cage 1422 may extend between the two jaw bars 1402. Multiple static jaw magnets 1410a may be connected along the length of each jaw member 1420. Two ear magnets 1410b may be positioned at opposing ends of a generally "U" shaped connecting member 1430 and may be mounted to the jaw members 1420. The ear magnets 1410b and connecting member 1430 may be directly mounted to the jaw members 1420 using any fastener known in the art such as an adhesive or bolts. The ear magnets 1410b may be poisoned above the jaw magnets and towards the rear of the muzzle 1400. As seen in FIG. 49, the magnetic dog muzzle 1400 may encompass the dog's entire jaw up to the ears in condensed magnetic fields. In some embodiments, the jaw magnets 1410a may be a different size than the ear magnets 1410b. For example, in a non-limiting embodiment, the jaw magnets 1410a may be 2 inch mounting magnets and the ear magnets 1410b may be 4 inch mounting magnets.

Figure 50A:
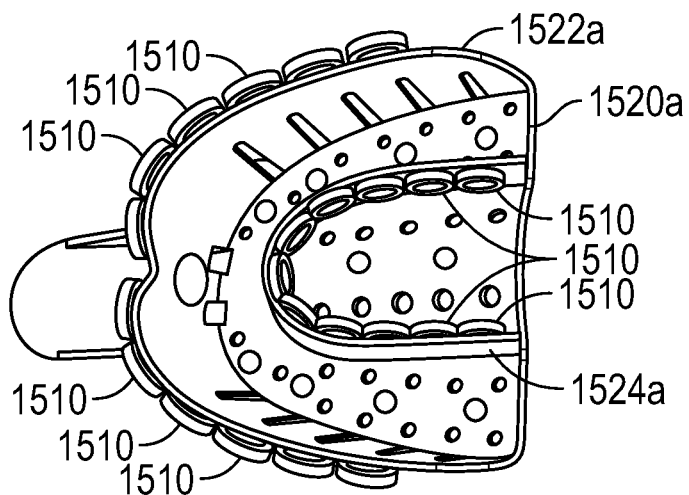
FIG. 50A is a perspective view of an embodiment of a magnetic therapy mouth guard.
Figure 50B:
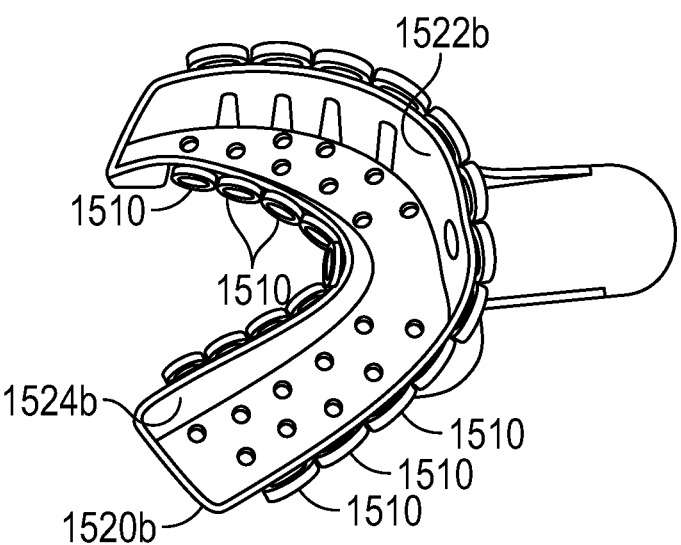
FIG. 50B is a perspective view of a second embodiment of a magnetic therapy mouth guard.

FIGS. 50A-B show embodiments of magnetic therapy mouth guards 1500a and 1500b. The magnetic mouth guards 1500a, 1500b may define an interior wall 1524a, 1524b, an exterior wall 1522a, 1522b, and a base 1520a, 1520b connecting the bottom end of the walls 1522a,b, 1524a,b. Multiple static magnets 1510 may be connected along each of the front 1522a,b and back 1524a,b walls. When the mouth guard is worn by a user, the user's teeth, jaw, and gums will be exposed to compressed magnetic fields produced by magnets 1510 on the outer walls 1522a,b interacting with magnets on the inner walls 1524a,b. FIG. 50A shows a first embodiment of a mouth guard 1500a that may be used for exposing the upper teeth, jaw, and gums to compressed magnetic fields. FIG. 50B shows a second embodiment of a mouth guard 1500b that may be used for exposing the lower teeth, jaw, and gums to compressed magnetic fields. In some embodiments, the magnets 1510 may be connected to the inner or outer side of the inner 1524a,b and outer 1522a,b walls. In other embodiments, the magnets 1510 may be embedded in the inner 1524a,b and outer 1522a,b walls. In some non-limiting embodiments, a pair of magnets 1510, one on the inner wall 1524a,b and one on the outer wall 1522a,b, may be provided and positioned for each individual tooth in a patients mouth. In other non-limiting embodiments, the mouth guards 1500a,b may only include magnets 1510 for select teeth and leave the remaining portions of the walls 1524a,b, 1522a,b free of magnets 1510. The mouth guards 1500a,b may be used to treat conditions such as oral cancer, tooth decay, and gum disease.

Figure 51:
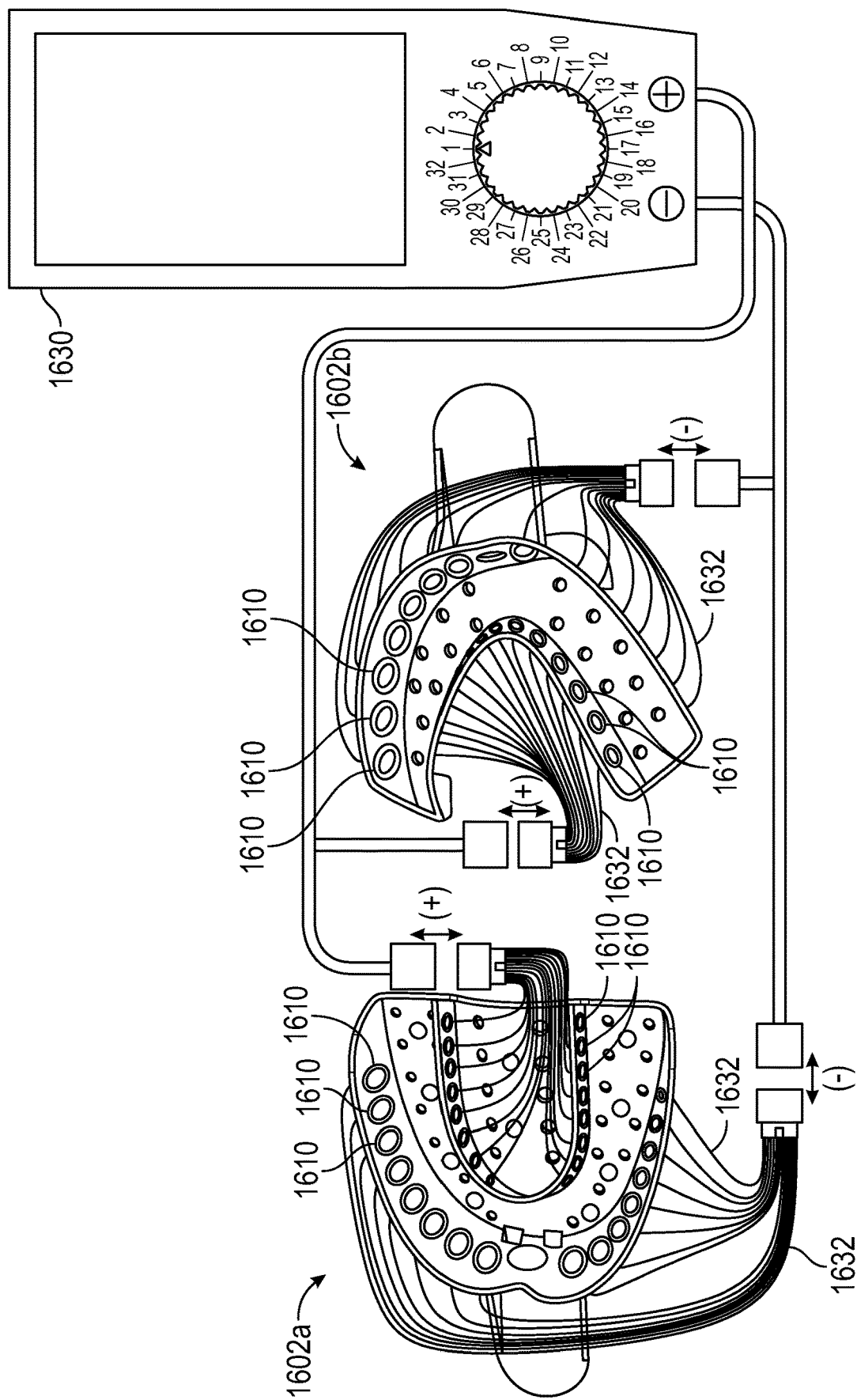
FIG. 51 is perspective view of an electronic, magnetic mouth treatment system.

FIG. 51 shows an embodiment of electronic, magnetic therapy mouth treatment system 1600 including upper 1602a and lower 1602b mouth guards. The mouth guards 1602a, 1602b may be similar to the mouth guards 1500a, 1500b of FIGS. 50A and 50B, with each mouth guard 1602a, 1602b having inner and outer walls connected at their bottom ends by a base. Each wall may be embedded with static magnets 1610 that are exposed to the tooth side of each wall. Each magnet 1610 may be electronically connected to a power source 1630 to act as an electrode. Each pair of magnets 1610 may correspond to a single tooth (i.e. a magnet on the inner wall and a magnet on the outer wall on opposing side of a tooth) and may be provided on a single circuit with one magnet 1610 acting as a positive electrode and the other magnet 1610 acting as a negative electrode. The individual circuits for each pair of magnets associated with a tooth may be provided by multiple sets of wires 1632 connected to a selectable power source 1630 capable of sending current trough individual circuits, and thus exposing individual teeth to electric current. The electric current may be used to remove select teeth without causing bleeding of the gums.

Figure 52:
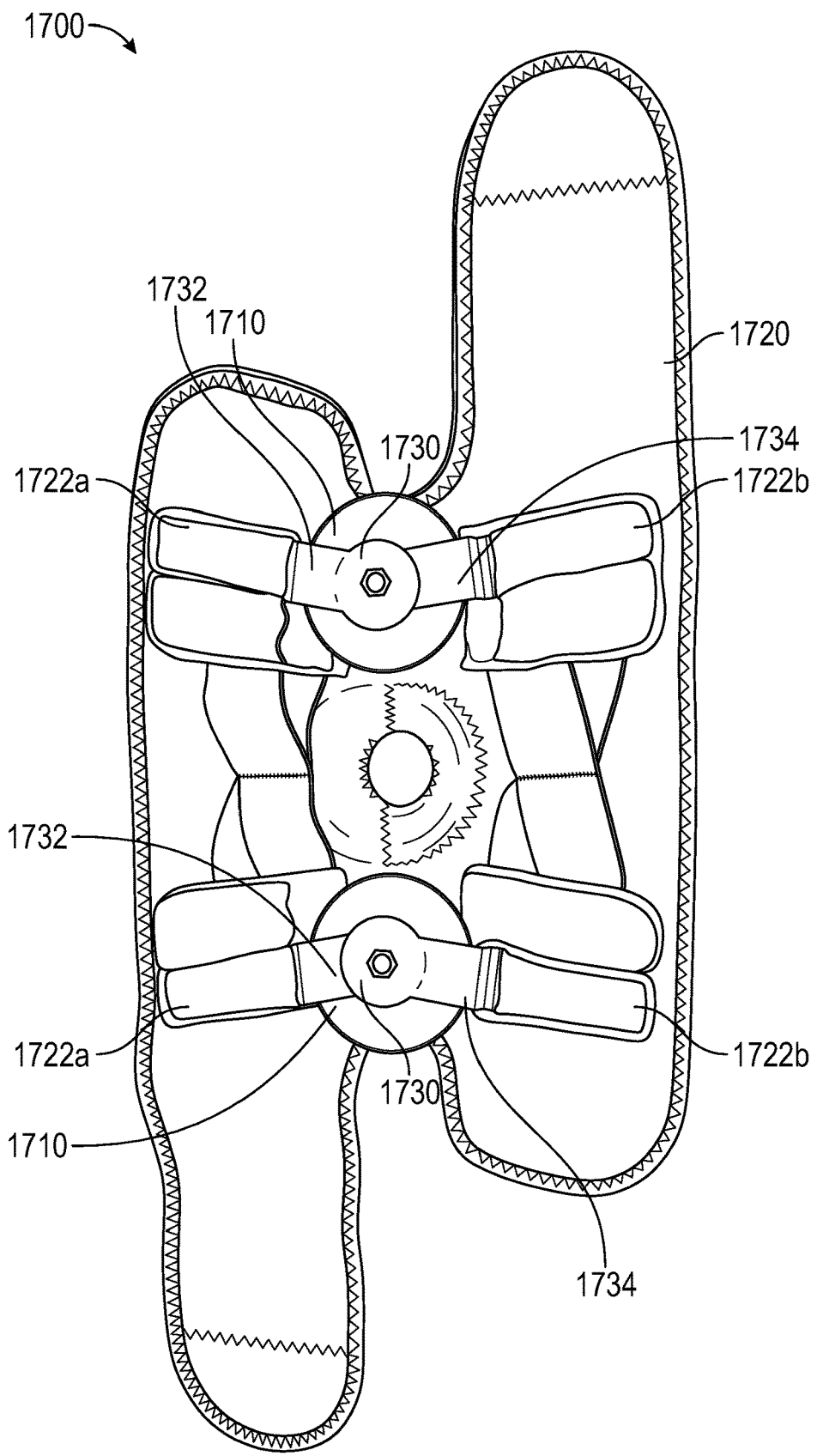
FIG. 52 is an overhead view of an embodiment of magnetic therapy knee brace in an unwrapped configuration.
Figure 53:
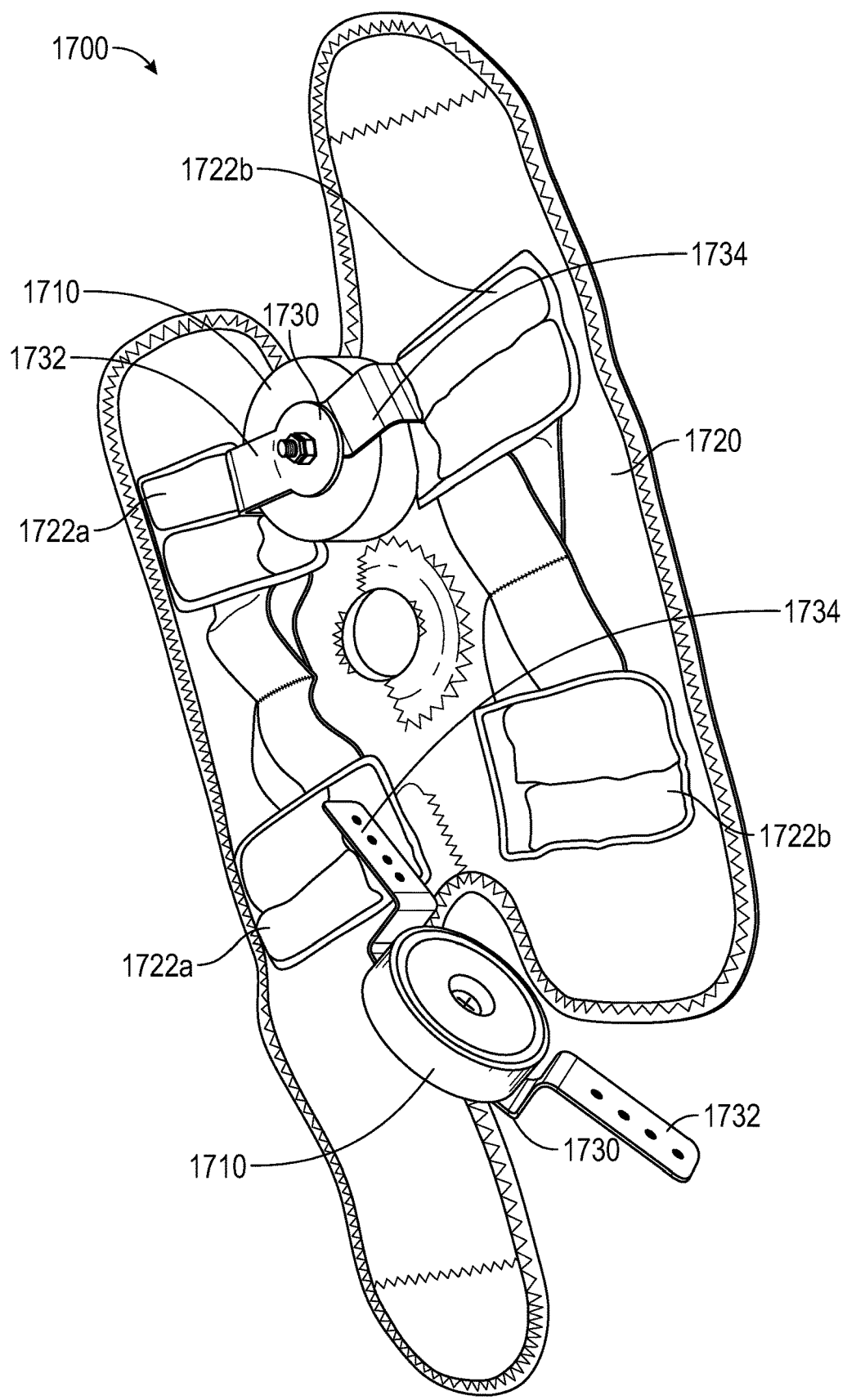
FIG. 53 is a perspective view of the magnetic therapy knee brace of FIG. 52 with one of the magnets and articulating member removed for illustration.
Figure 54:
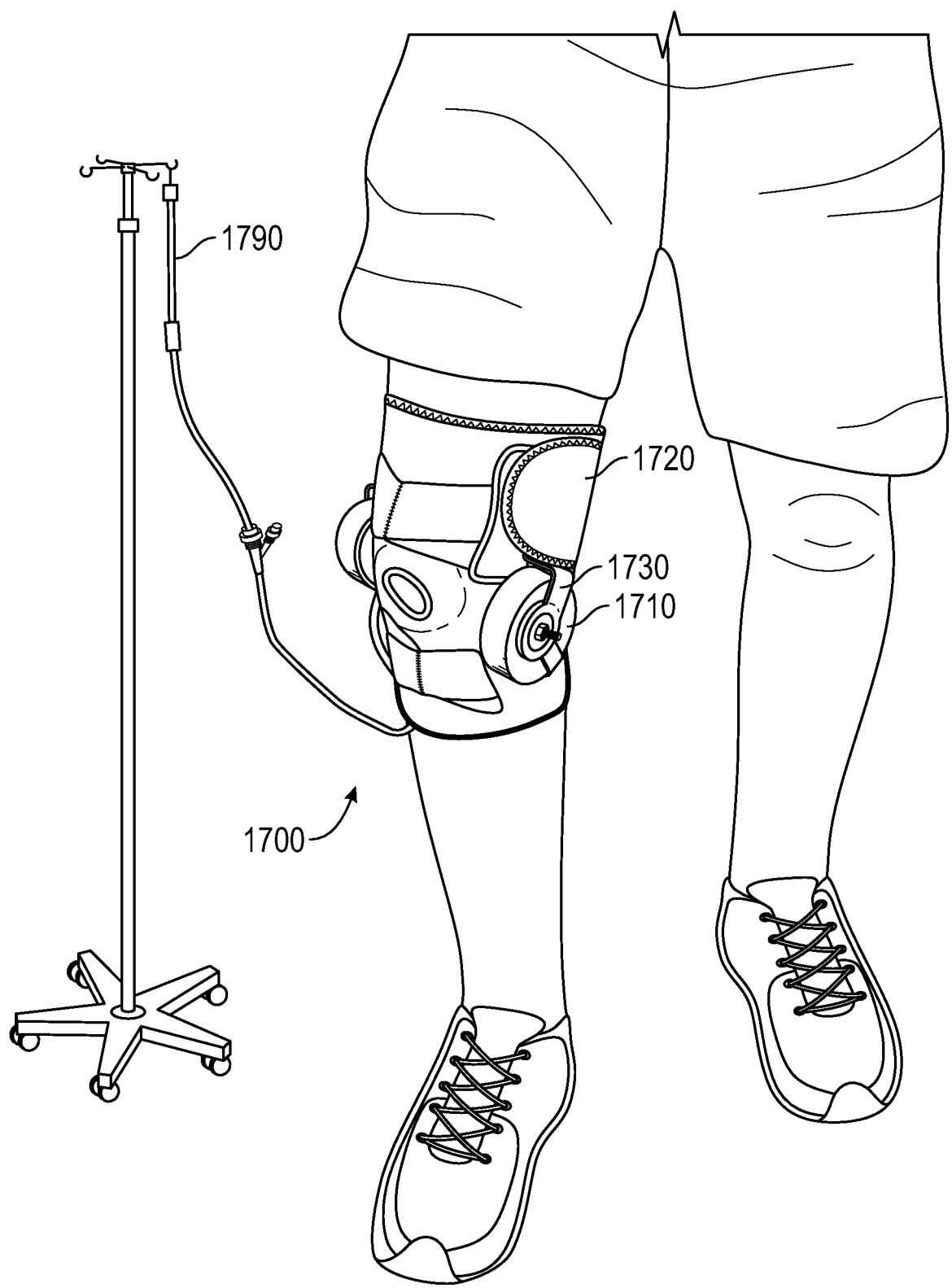
FIG. 54 is an environmental view of the magnetic therapy knee brace of FIG. 52 wrapped around the knee of a user.

FIGS. 52-54 show an embodiment of a magnetic knee brace 1700. The knee brace 1700 includes a support wrap 1720, two static magnets 1710, and articulating magnet supports 1730. Each magnet 1710 is attached to an articulating support 1730 at the articulating joint. The support wrap 1720 includes two sets of pockets 1722a,b for supporting the magnets 1710 and articulating magnet supports 1730 on the medial and lateral sides of the knee. Each set of pockets 1722a,b has an upper pocket 1722a to be positioned above the knee and a lower pocket 1722b to be positioned below the knee. Each set of pockets 1722a,b may accept the arms 1732, 1734 of the articulating support. When attached to a user's knee, as seen in FIG. 54, the magnets 1710 are held in place at the medial and lateral side of the user's knee. The articulating supports 1730 allow the knee joint to be flexed while maintaining the magnet 1710 placement. In some non-limiting embodiments, the magnets 1710 may have a strength that results in the magnet field on the opposing side of the knee to have the strength of 0.01 to 10 Gauss when only one of the two magnets is present. For example, the magnets may be mounting ring magnets having a diameter in the range of 2 to 5 inches, a thickness in the range of 0.5 to 1 inches, and a grade in the range of N45-N52. In addition to the magnetic therapy, stem cells may also be injected into the target tissue or adjacent tissue to provide additional stem cell at the target tissue. The stem cells may be injected through an injection port 1790 having an outlet that dispenses the stem cells in or near the target tissue. Stem cells may be used in addition to any magnetic therapy treatment or device within the scope of this disclosure to provide enhanced tissue regrowth.

Figure 55:
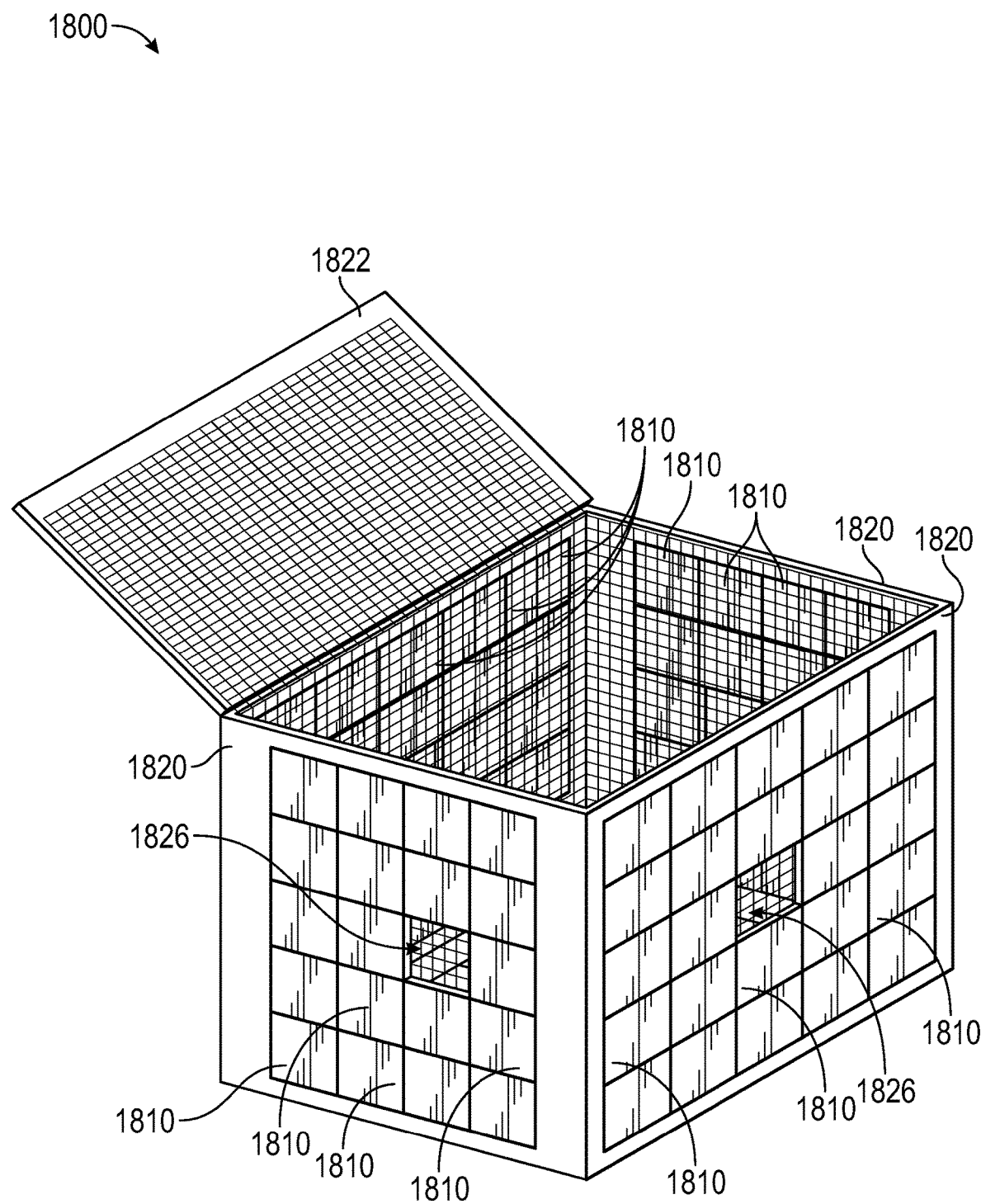
FIG. 55 is a perspective view of a magnetic therapy crate with the lid opened.
Figure 56:
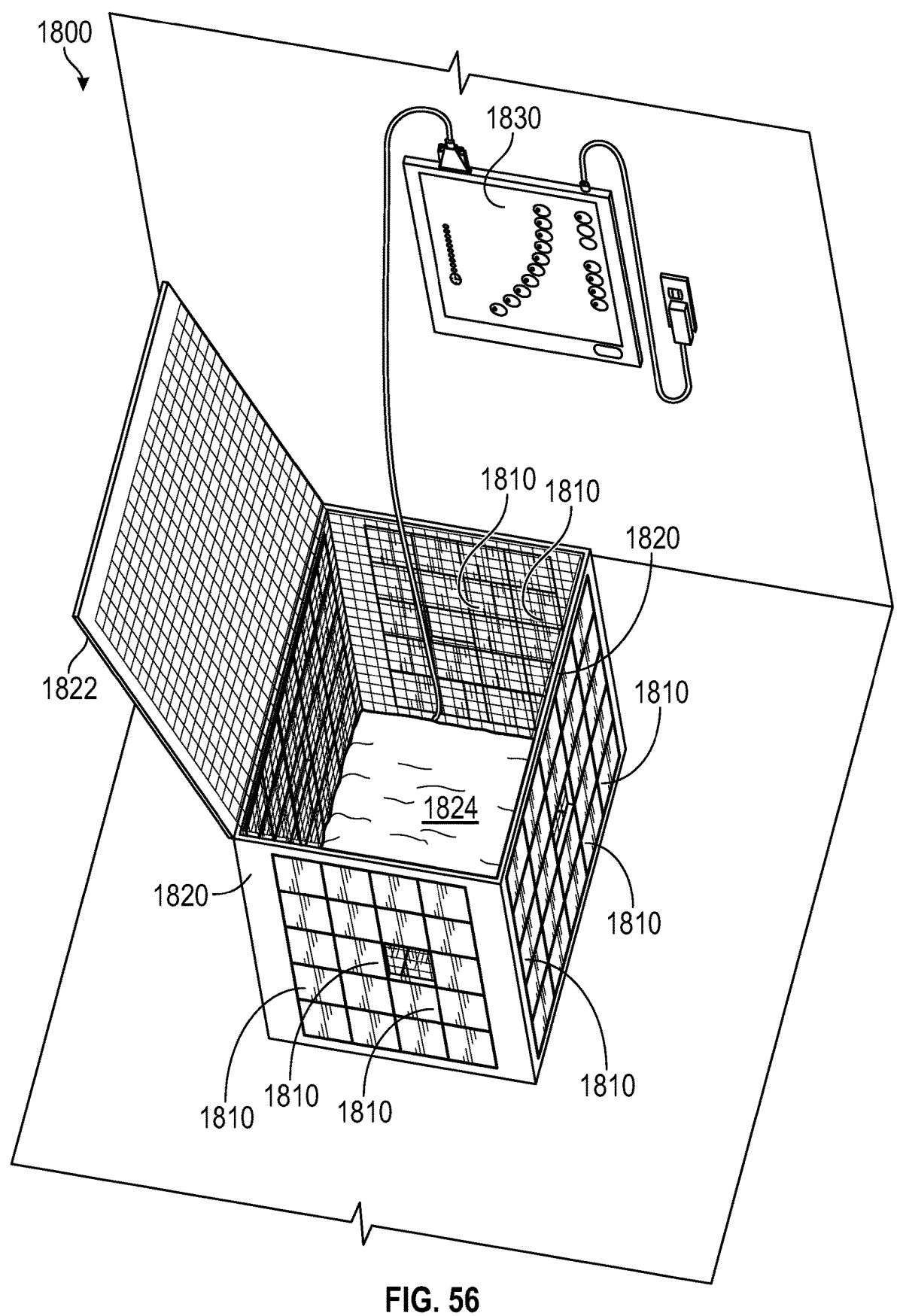
FIG. 56 is an environmental perspective view of the magnetic therapy crate of FIG. 55.
Figure 57:
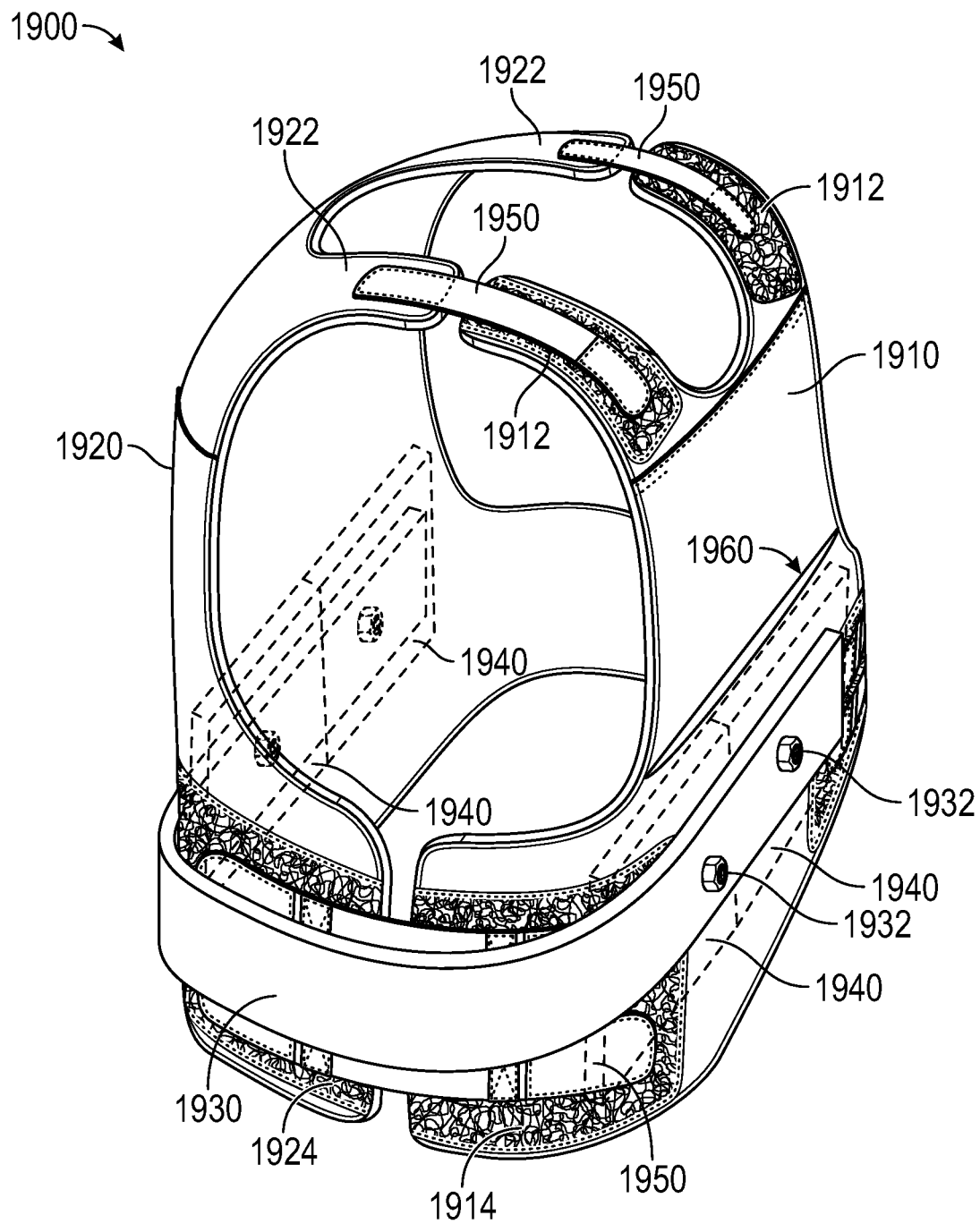
FIG. 57 is a perspective view of a magnetic vest.
Figure 58:
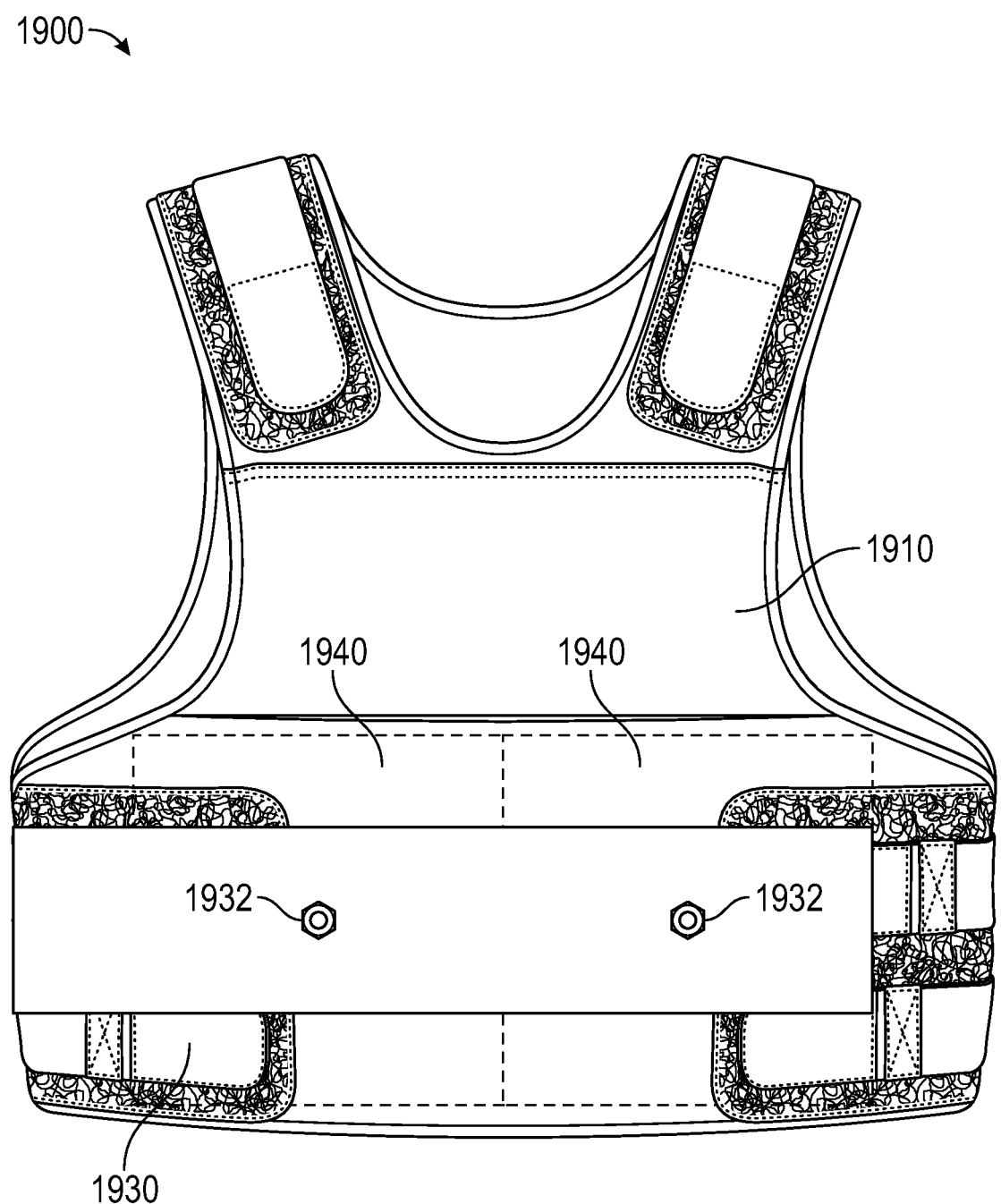
FIG. 58 is a front view of the magnetic vest of FIG. 57.
Figure 59:
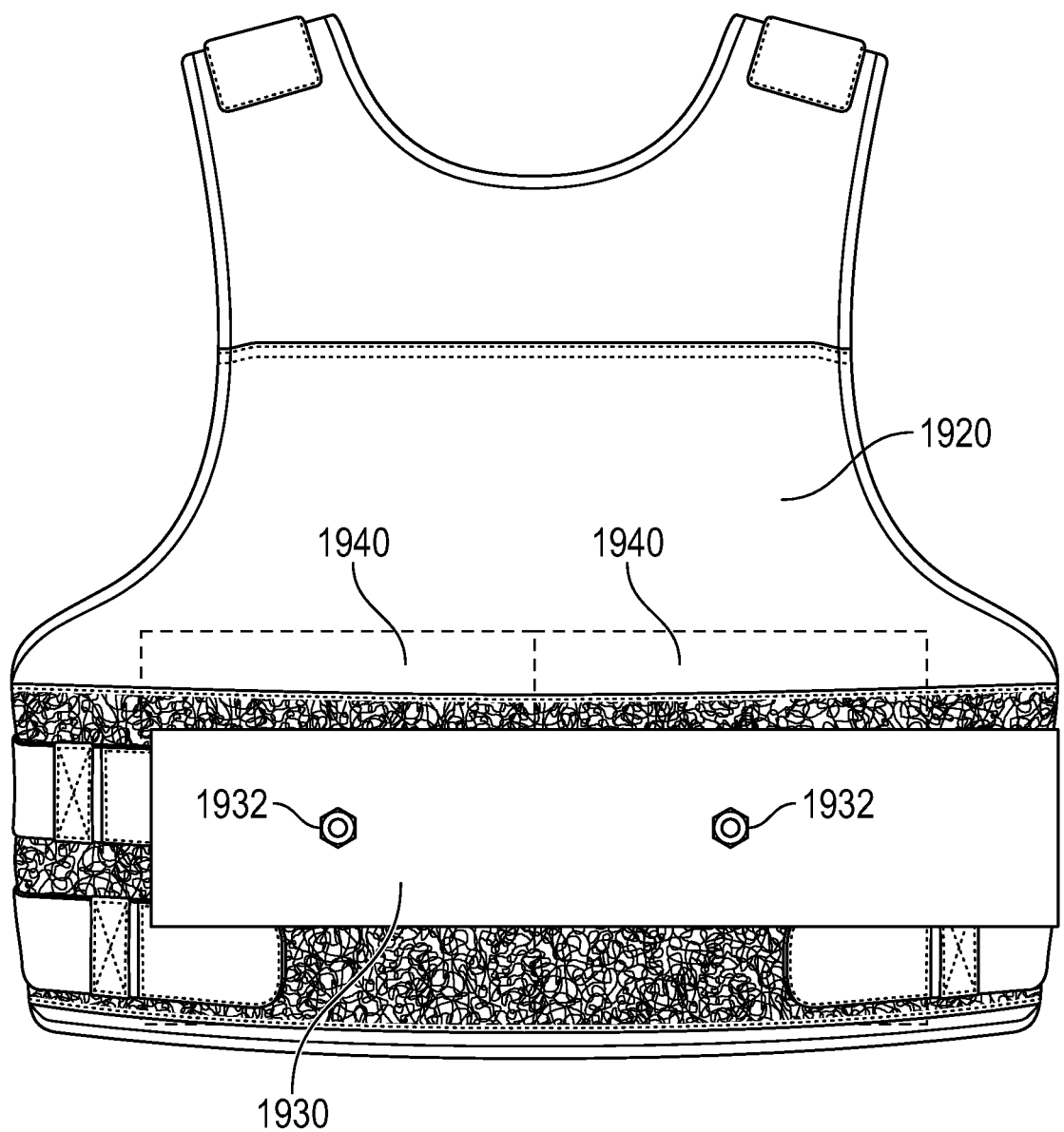
FIG. 59 is a back view of the magnetic vest of FIG. 57.

FIGS. 55 and 56 show a magnetic therapy animal crate 1800. The crate 1800 may define six sides, including four side walls 1820, a base 1824, and lid 1822, that form an enclosure for the animal. Each of the side walls 1820, the base 1824, and the lid 1822 may include an array of static magnets 1810. For example, in some non-limiting embodiments, each of the four side walls 1820 and the base 1824 may include magnetic arrays while the lid 1822 does not. The arrays of magnets 1810 may be designed to take up the entirety of the side or just a portion. In some embodiments, all of the magnets 1810 may be directed into the enclosure. Openings 1826 may be defined in the side walls to provide airflow through the crate. During use, a pulsed electric field generator may be used on the animal residing within the magnetic therapy animal crate to prevent, or at least mitigate, rouleau formation in the blood.

FIGS. 57-60 show an embodiment of a magnetic vest 1900 for treating tissue within the abdomen of a user. The vest 1900 may have a front portion 1910 and a back portion 1920. Each portion 1910, 1920 may have two shoulder flaps 1912, 1922 and two flank flaps 1914, 1924. The front and back portions 1910, 1920 may be connected by adjustable straps 1950 spanning from each shoulder 1912 or flank flap 1914 on the front portion 1910 to the corresponding shoulder 1922 or flank flaps 1924 on the back portion 1920.

The front 1910 and back 1920 portions may each define a magnet pocket 1960. The magnet pockets 1960 may be located at any position on the front 1910 and back 1920 portions, and may be adjusted based on the location of the tissue requiring magnetic treatment. In the embodiments shown in FIGS. 57-60, which may be for treating tissue in the kidneys, liver, intestines, stomach, and/or pancreas, the magnet pockets 1960 extend between the flank flaps 1914, 1924. Two static magnets 1940 are provided in each pocket 1960 and may have their strong magnetic field facing towards and inside of the vest 1900 to increase tissue penetration. In alternate embodiments, the vest 1900 may include two or more magnets 1940, and the magnets 1940 may have various shapes and sizes to accommodate the needs of the patient and/or practitioner. In some non-limiting embodiments, the magnets 1940 may be secured to the vest 1900 using straps, brackets, or other means known in the art for attaching rigid elements to a semi-rigid device.

Figure 60:
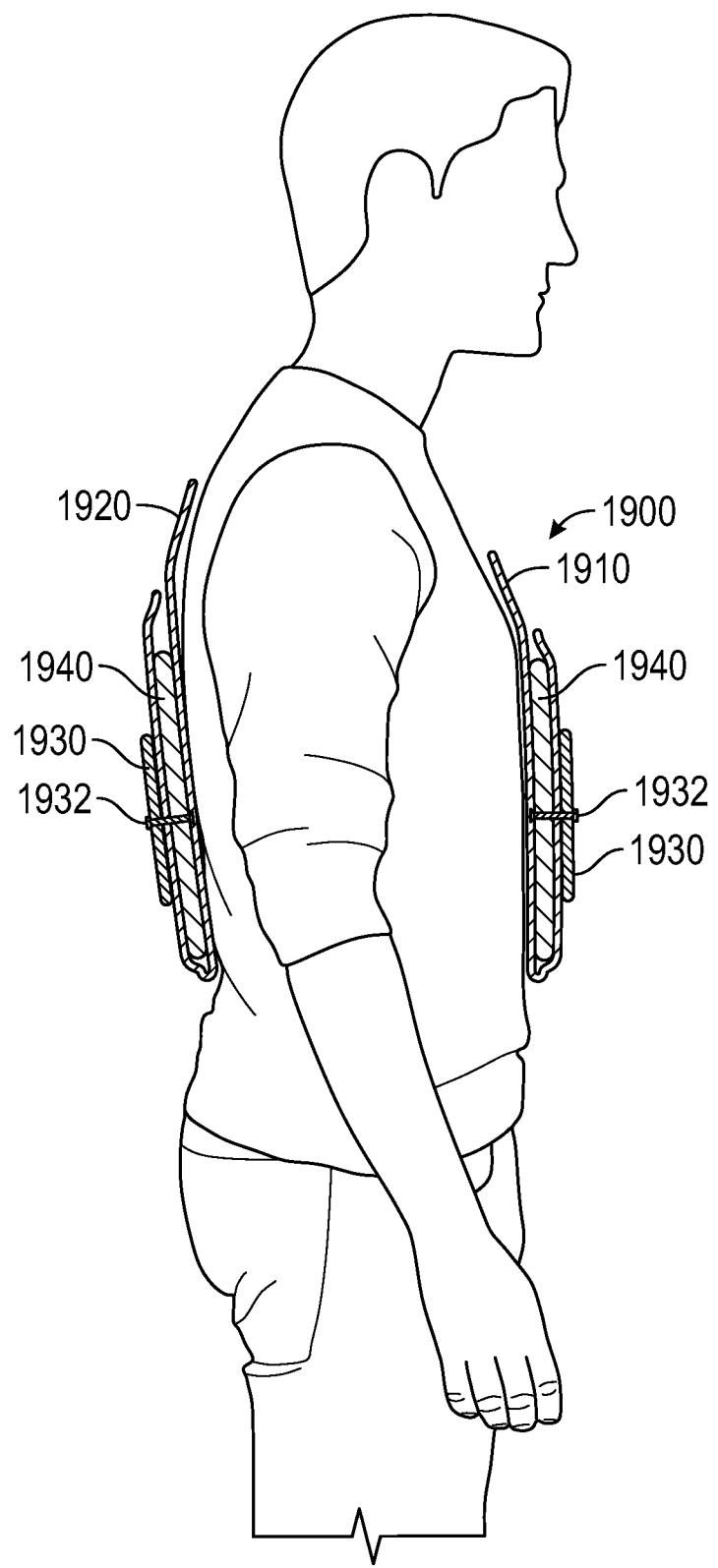
FIG. 60 is a sectional side view of the magnetic vest of FIG. 57.
Figure 61:
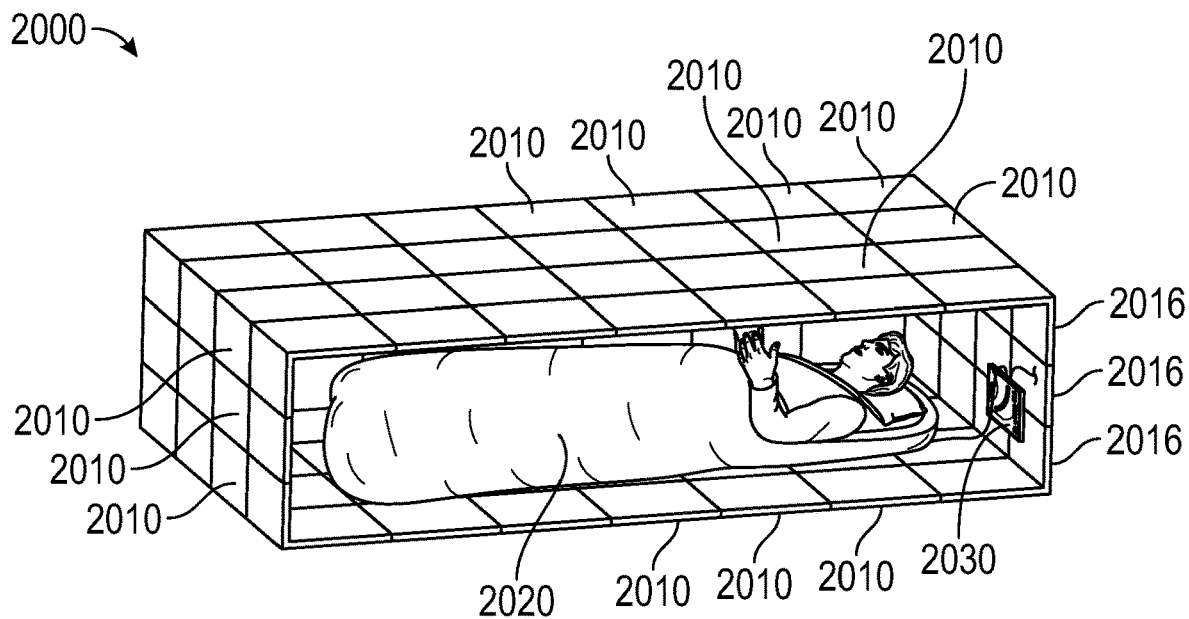
FIG. 61 is a perspective view of a magnetic sleeping pod from the front.

A rigid member 1930 may be secured to an outer side of each magnet 1940 to prevent the magnets 1940 from becoming magnetically attached when the vest 1900 is not being worn by the user, or when the vest 1900 in the process of being donned and doffed by the user. In some embodiments, the rigid member 1930 may be generally "U" shaped and may extend across the flank flaps 1914, 1924 of the user. Each magnet 1940 may be connected to the rigid member 1930 by a bolt 1932 which extends through an opening in the magnet 1940, as shown by FIG. 60.

Figure 62:
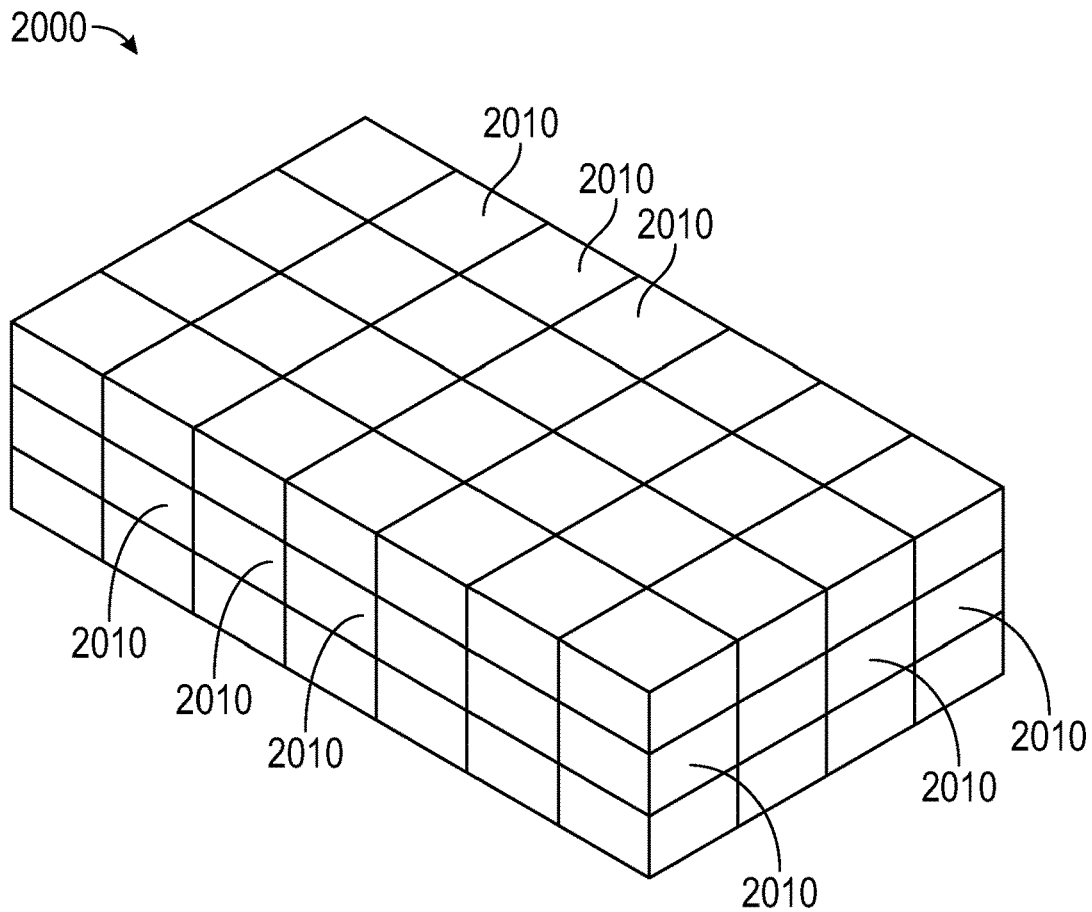
FIG. 62 is a perspective view of the magnetic sleeping pod of FIG. 61 from the rear.
Figure 63:
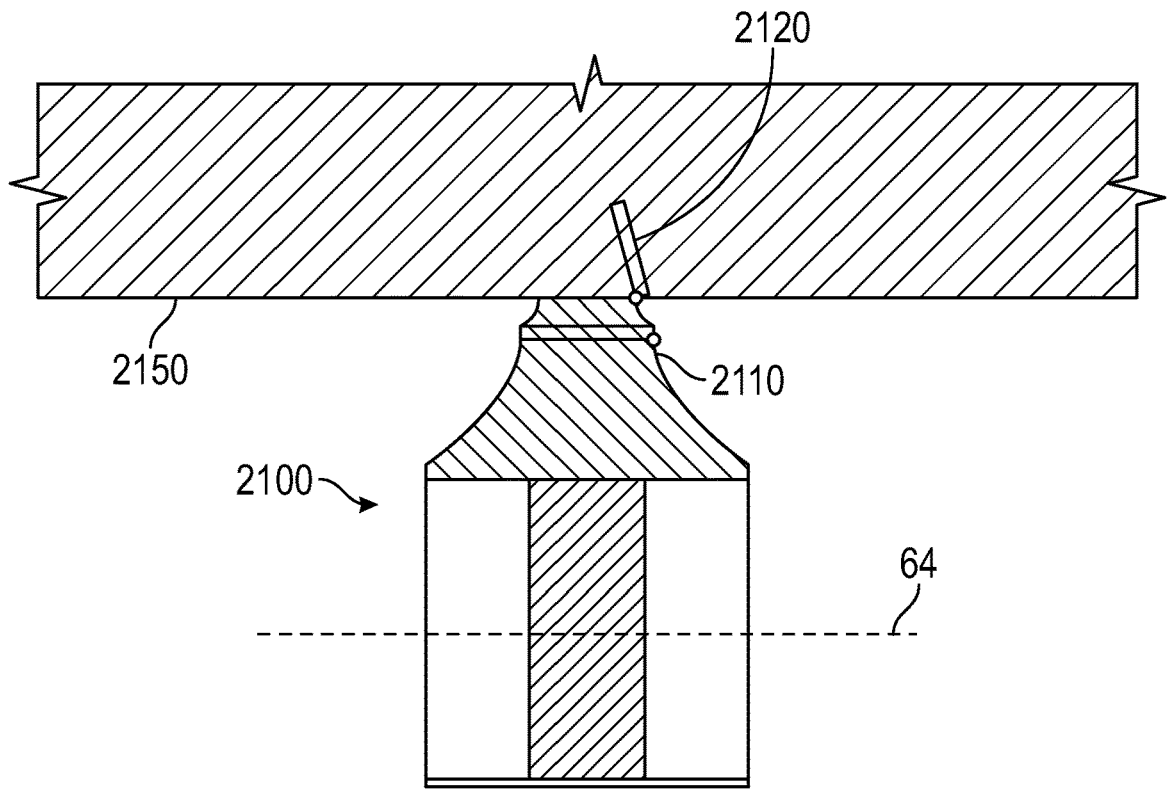
FIG. 63 in an overhead view of a sleeping unit, containing magnetic sleeping pods of FIG. 61, docked with a spacecraft.
Figure 64:
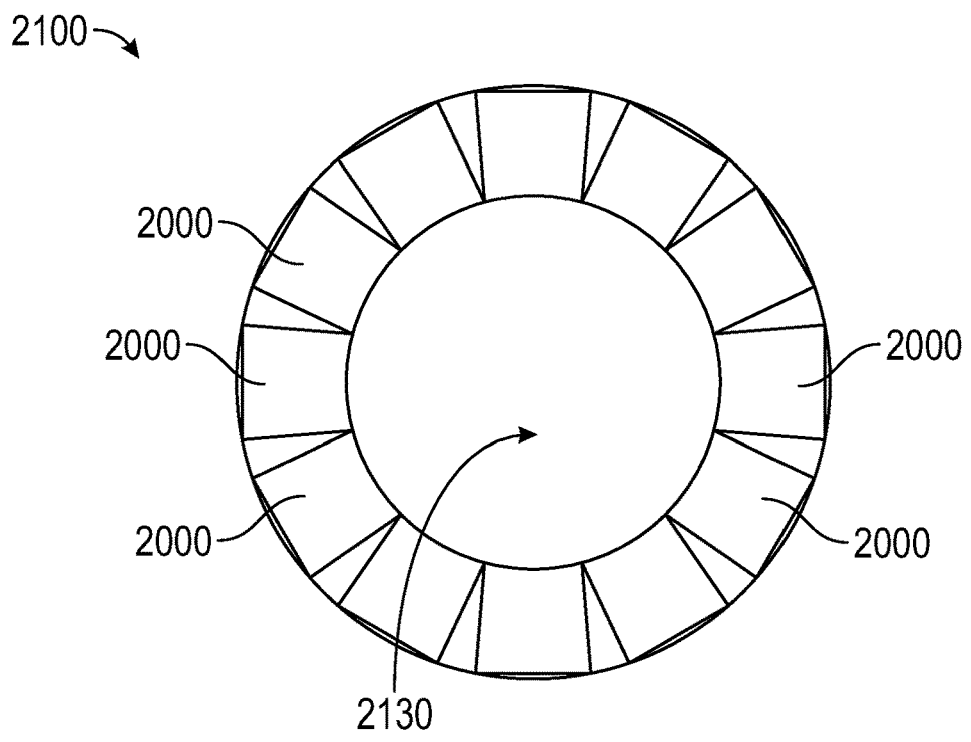
FIG. 64 is a cross sectional view of the sleeping unit of FIG. 63.

FIGS. 61-64 shown a magnetic sleeping pod 2000 for stimulating the body's immune system to treat abnormal or damaged tissue, as well as protect the body from electromagnetic radiation. The pod 2000 may define an enclosure with one open side. In the embodiment shown in FIGS. 62-64, the enclosure is made of 5 planar walls connected at right angles. In other embodiments, the walls of the pod 2000 may be arcuate or have rounded edges. The walls of the pod may comprise an array of static magnets 2010 dispersed throughout the walls. In some embodiments, as shown in FIGS. 62-64, the magnets 2010 may be evenly dispersed throughout the walls and may cover an entire surface area of the walls. Accordingly, a user positioned within the pod 2000 will be exposed to multiple compressed magnetic fields which stimulate the immune system and block hazardous electromagnetic radiation from entering the user.

When inside the sleeping pod 2000, a user may be connected to a pulsed electromagnetic field generator 2030, such as a Bemer 3000™. In some cases, the magnetic field provided by the sleeping pod 2000 may cause the user's red blood cells to form rouleaues which can decrease circulation. When connected to the user, the electromagnetic pulses from the pulsed electromagnetic field generator 2030 may prevent the user's red blood cells from forming rouleaues, thus increasing blood flow. The pulsed electromagnetic field generator 2030 may be electrically connected to the user by one or more patches connected to the user's skin. Alternately, or in addition to the patches, the user may lay in a sheath or sleeping bag 2020 wherein the internal surface is an electrode of the pulsed electromagnetic field generator, thus providing electrical contact over a large portion of the body. In some embodiments, the user may lay on a pad having an electrode of the pulsed electromagnetic field generator covering its upper surface to provide electrical contact over a large part of the body.

FIGS. 63-64 show a sleeping pod unit 2100 which may be used attached to a spacecraft 2150. The sleeping pod unit 2100 may include a docking portion 2110 which may dock with a port on the spacecraft 2150. The unit 2100 defines a circular cross-section having multiple sleeping pods 2000 dispersed around its circumference. Each pod 2000 opens into a central chamber 2130 which may be used for entering and exiting the pods 2000. The sleeping pod unit 2100 may be entered and exited through a door 2120 in the docking portion 2110. The standalone sleeping pod unit 2100 may maintain the static magnets 2010 at an adequate distance away from the spacecraft 2150 to prevent the magnetic fields from disrupting electrical instrumentation on the spacecraft.

Figure 65A:
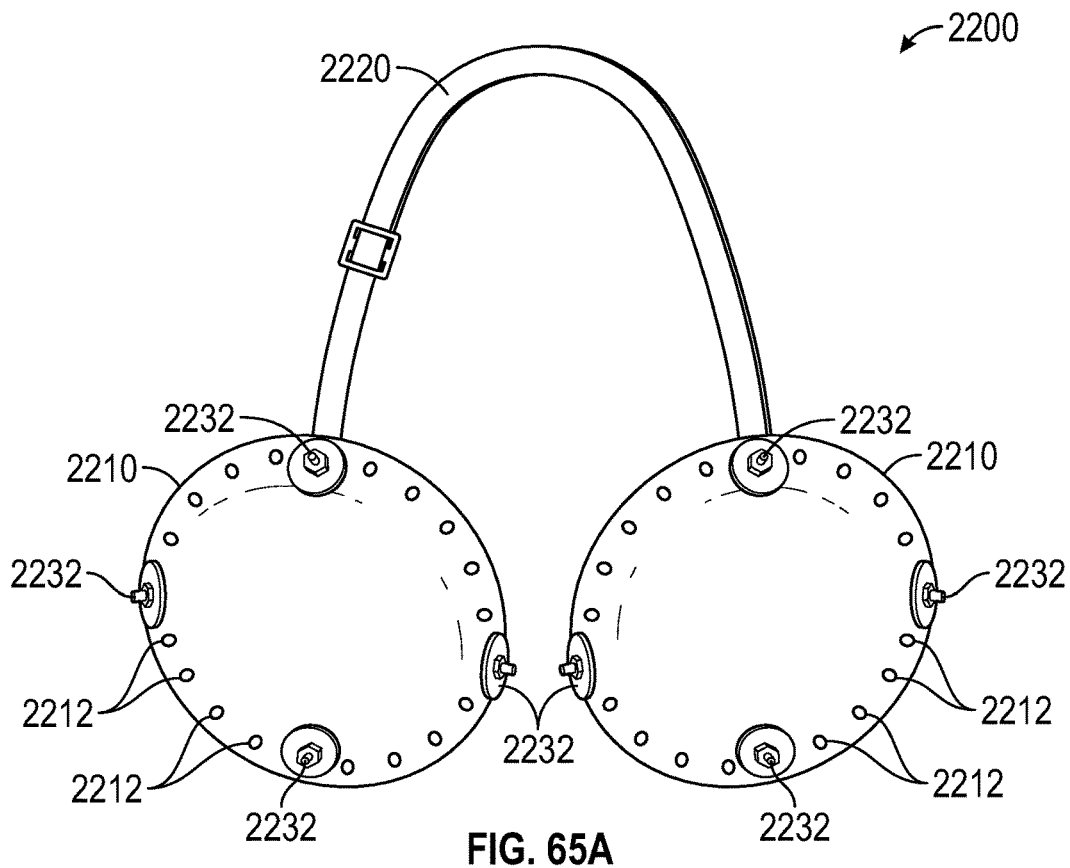
FIG. 65A shows a front view of a magnetic therapy bra.
Figure 65B:
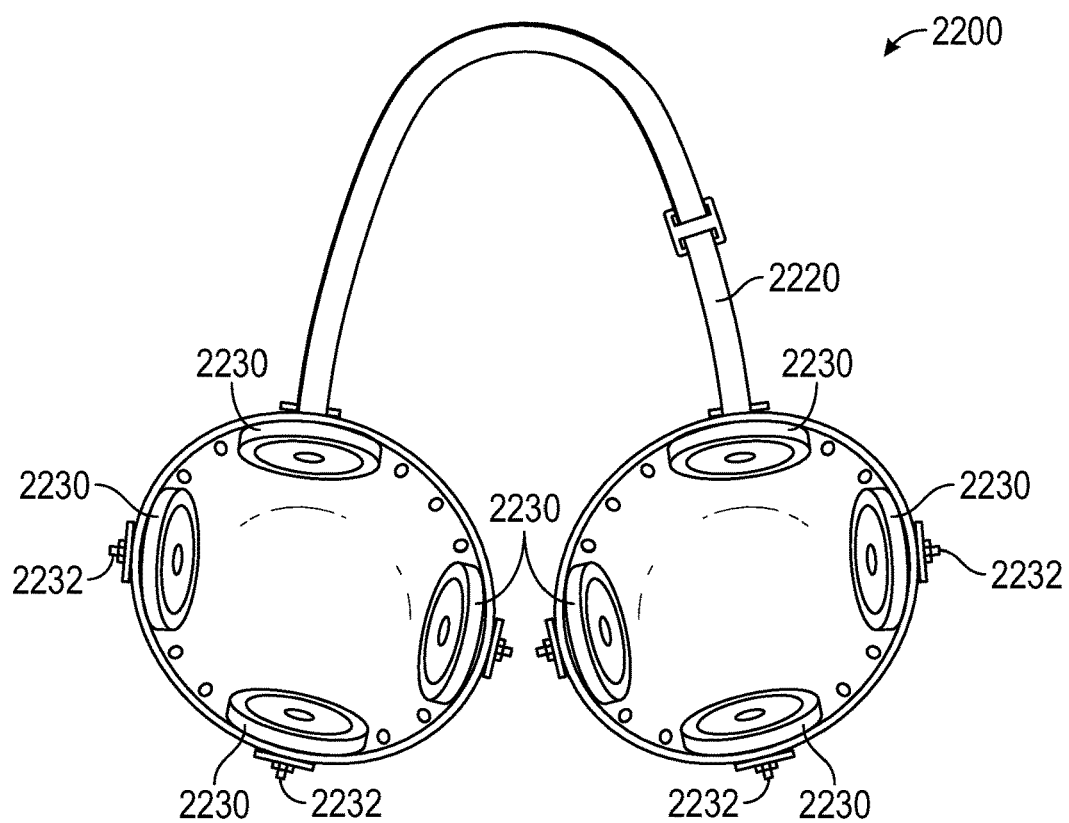
FIG. 65B shows a rear view of the magnetic therapy bra of FIG. 65A.

FIGS. 65A and 65B show an embodiment of a magnetic therapy bra 2200 for treating tissue in the breast and/or chest area of a patient. The bra 2200 includes two rigid cups 2210 having a series of holes 2212 spaced apart around their perimeter for attaching static magnets 2230. The magnets 2230 may be mounted on the inside surface of the cups 2210 with their fields directed inwards. The holes 2212 allow a position of the magnets 2230 to be adjusted based on location of the treatment tissue with respect to the cups 2210. The magnets 2230 may be attached to the holes by a screw and bolt connection 2232, as shown in FIGS. 65A and 65B, or other removable connections known in the art. Accordingly, a strongest portion of the compressed magnetic fields may be adjusted to lie in the treatment tissue and adjacent healthy tissue. An adjustable neck strap 2220 may be used to hold the cups in place over a patient's chest/breasts.

Figure 66A:
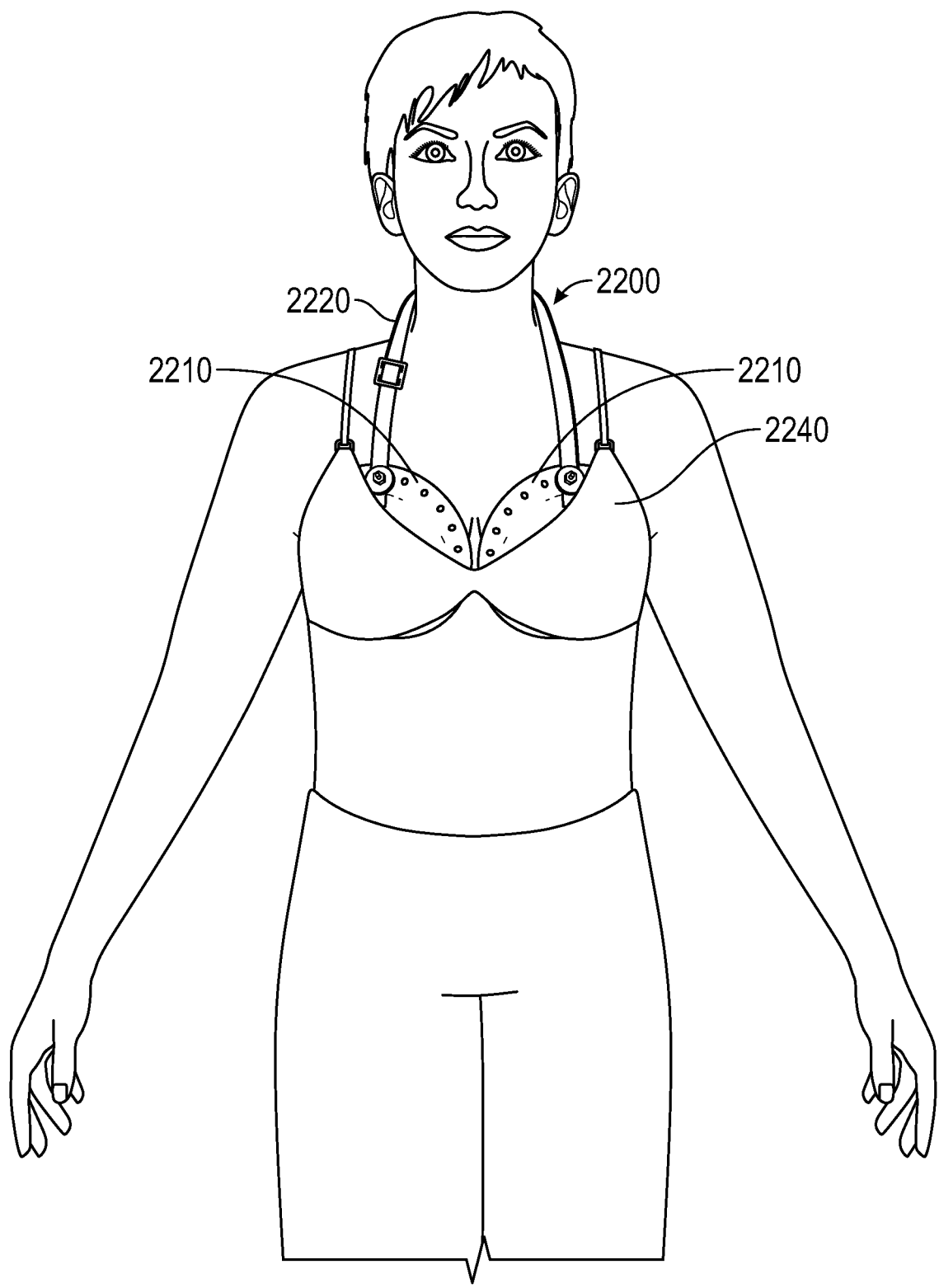
FIG. 66A shows an environmental, front view of the magnetic therapy bra of FIG. 65A being worn on a patient.
Figure 66B:
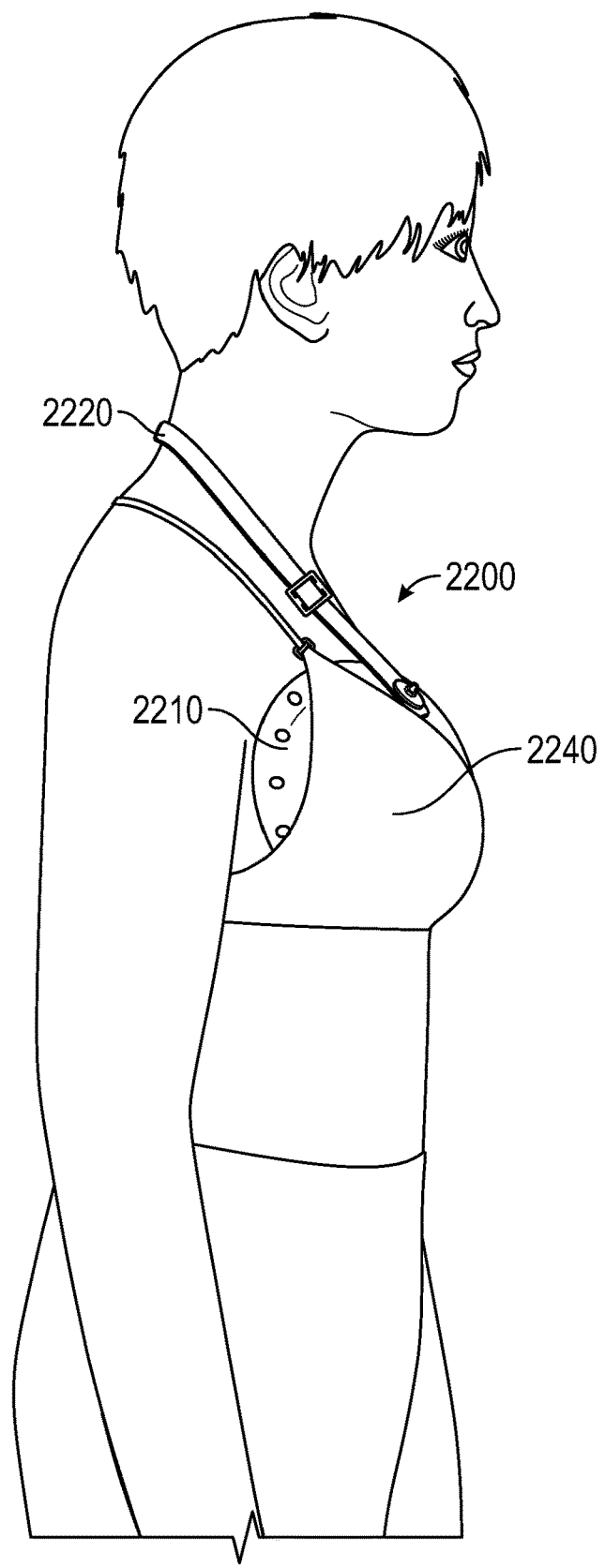
FIG. 66B shows an environmental, side view of the magnetic therapy bra of FIG. 65A being worn on a patient.
Figure 66C:
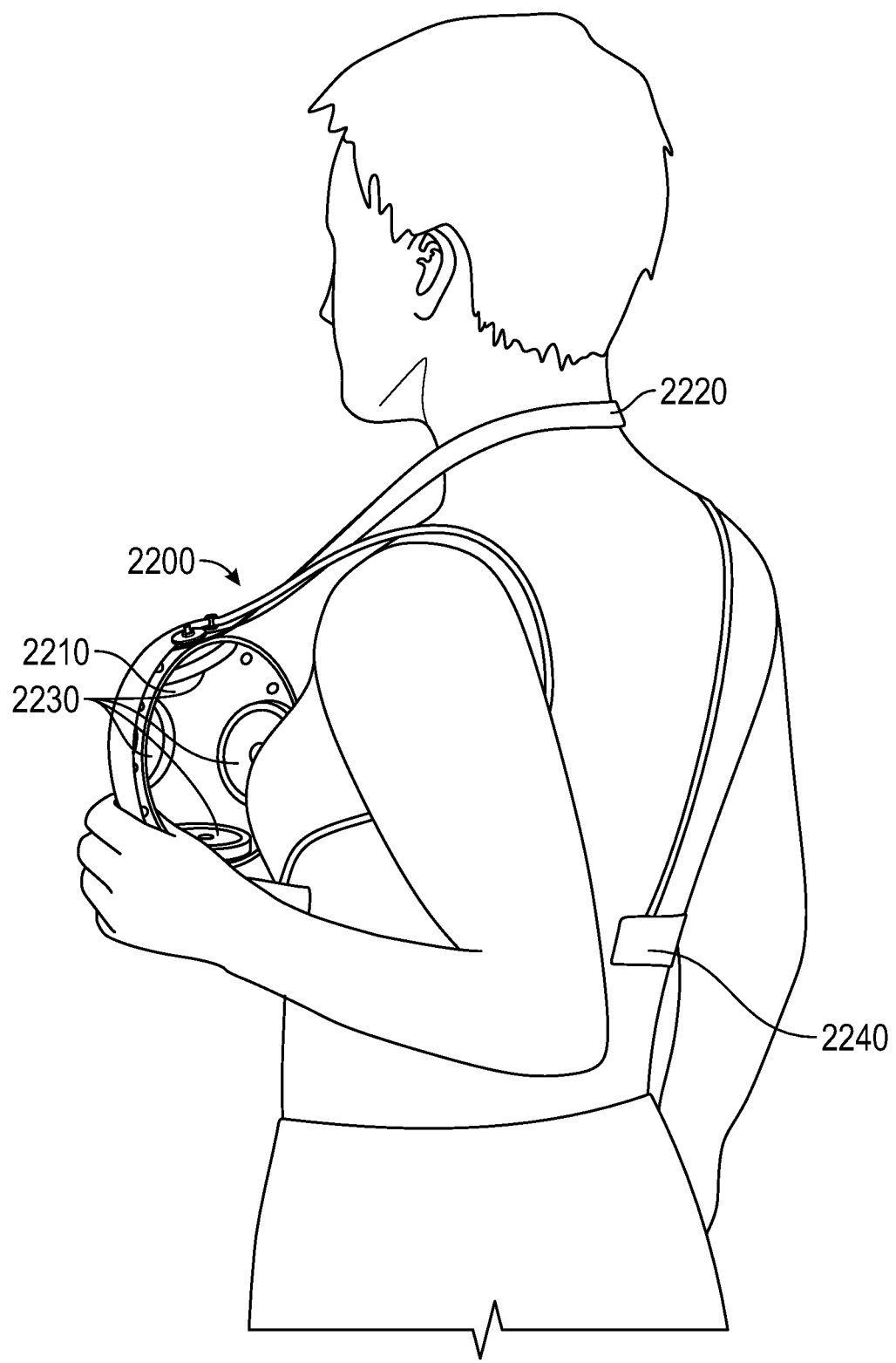
FIG. 66C shows an environmental, rear view of the magnetic therapy bra of FIG. 65A partially removed from a patient.
Figure 66D:
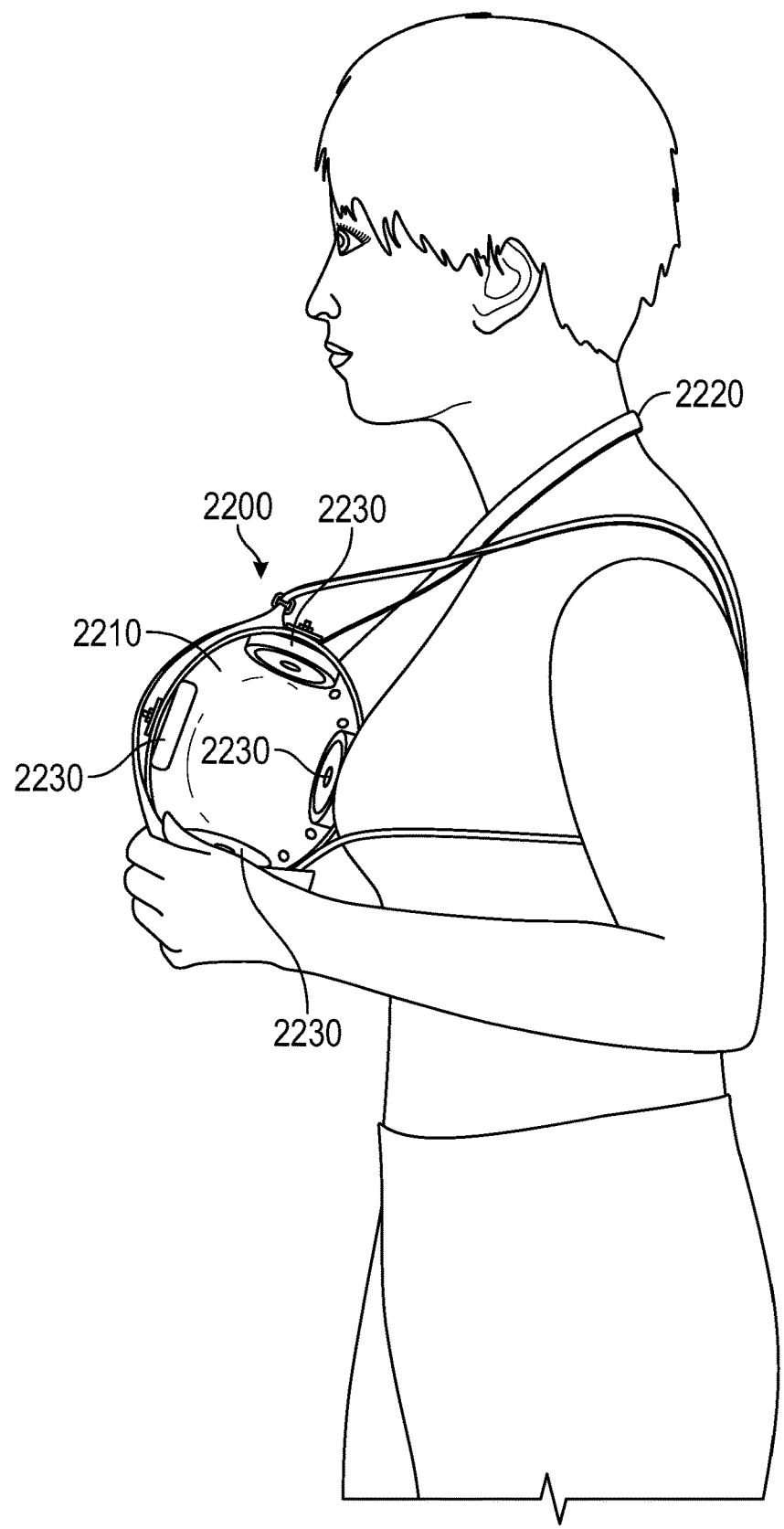
FIG. 66D shows an environmental, side view of the magnetic therapy bra of FIG. 65A partially removed from a patient.

FIGS. 66A-66D show the magnetic therapy bra 2200 being worn by a patient. Each cup 2210 is placed over a respective breast, thus providing compressed magnetic fields throughout the breast tissue. The strap 2220 may be adjusted to hold each cup 2210 over a respect breast when the strap 2220 is worn around a patient's neck. A traditional bra 2240 may be worn over the magnetic therapy bra 2200 for securing the cups 2210 in place. FIGS. 66C and 66D show a cup 2210 partially removed from the breast to show one of many possible magnet 2230 configurations that may be used on the cups 2210. As previously discussed, a location of the magnets 2230 on the cups 2210 may be adjusted to target specific areas of the breast tissue.

A method of using any device within the scope of this disclosure may include adjusting the position of the magnet based on feedback from neutron tomography. Neural tomography disperses neutrons through an object and detects changes to the magnetic moments of the neutrons to map magnetic fields within an object. Accordingly, the magnetic device can be optimally positioned on a patient by mapping the magnetic fields within the patient's body using the neutron tomography and adjusting the fields to compress in and around the target tissue.

A method of adjusting a magnetic device on a patient may include: attaching the magnetic device to the patient; mapping the magnetic fields produced in the patient by the magnetic device using neuron tomography; and adjusting the location of the magnets to maximize the amount of compressed magnetic fields in and/or around the target tissue. In some embodiments, multiple iterations of mapping and adjusting may be performed.

A method of using any device within the scope of this disclosure may include attaching the device to a patient so the magnetic fields compress in targeted tissue. The compressed magnetic fields may increase the presence of stem cells in and around the tissue. The stem cells may then differentiate to replace the damages tissue. In some cases, such as in damaged cardiac tissue, stem cells do not differentiate and replace the damaged tissue. However, the presence of stem cells, dead or alive, results in repair of the cardiac tissue. This is due to the stem cell emitting factors that produce an immune response which repairs the tissue. Accordingly, the presently disclosed magnetic device may be used to increase the presence of stem cells in a location of the body for producing an immune response to repair damaged tissue.

A method for stimulating the immune system to treat damaged or abnormal tissue using compressed static magnetic fields may include positioning first and second magnets so each magnet provide a magnetic field of at least 0.01 gauss over the target tissue when the other magnet is not present. As a result, at least two magnetic fields having a strength of at least 0.01 Gauss will be compressing the opposing magnet's field. If the two magnetic fields are from the same pole, such as both fields being north pole magnetic fields, the compressed fields will have a subtractive effect on each other with respect to magnetic flux density. Accordingly, a midpoint of the interaction between the magnetic fields will have a magnetic flux density of 0 Gauss. The present disclosure and experiments do not require a quantity of magnetic flux, but rather an compression of static magnetic fields.

A magnetic therapy exposure schedule may be varied based on the user, the condition being treated, and the device providing the treatment. For example, devices that provide magnets in close proximity to the skin may be used on a three days on, two days off schedule. This schedule may provide the skin time to regenerate between treatments which in some cases cause irritation to the skin. In some cases the schedule may include 1 h to 1 week on, with 45 minutes to 5 days off. Days off may be provided by moving the magnets to different location so magnets therapy may still be applied to the user.

A method of performing clinical trial of the aforementioned magnetic therapy may include using magnets of different strengths. In addition, placebos magnets may also be used to provide a placebo group.

Figure 67:
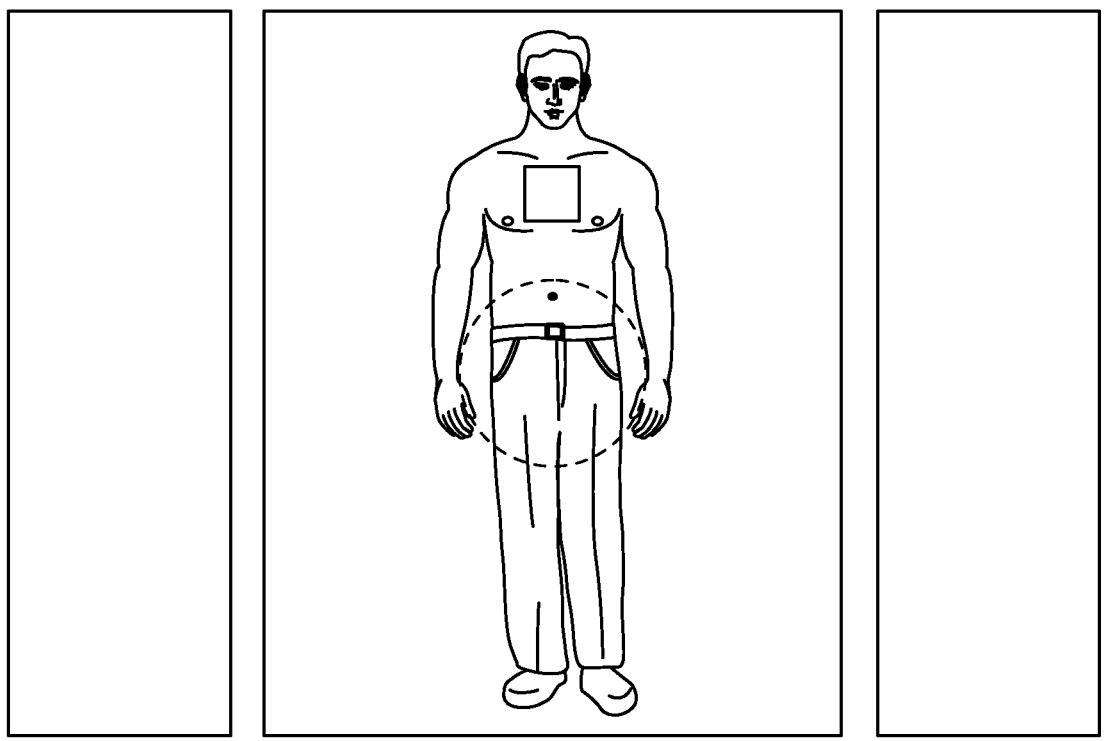
FIG. 67 shows a diagram of polarized neutron imaging device imaging magnetic fields within a human.

A polarized neutron imaging device 995 may be used with any magnetic therapy device within the scope of this disclosure to enhance the magnetic therapy by guiding adjustment of the magnets based on how the magnetic fields pass through the patient's tissue. FIG. 67 shows an example of magnetic fields within a patient being detected by a polarized neutron imaging device 995. Magnets 1210 may be placed on a patient based on the location of target tissue. The polarized neutron imaging device 995 may then be used to determine how the magnetic fields extend through the patient's body. The position, orientation, and/or strength of the magnets 1210 may be adjusted to provide a desired strength magnetic field at and/or around the target tissue. For example, the position and orientation of the magnets 1210 may be adjusted until the polarized neutron imaging device 995 indicates the target tissue is exposed to the highest magnitude of compression between the magnetic fields.

Figure 68:
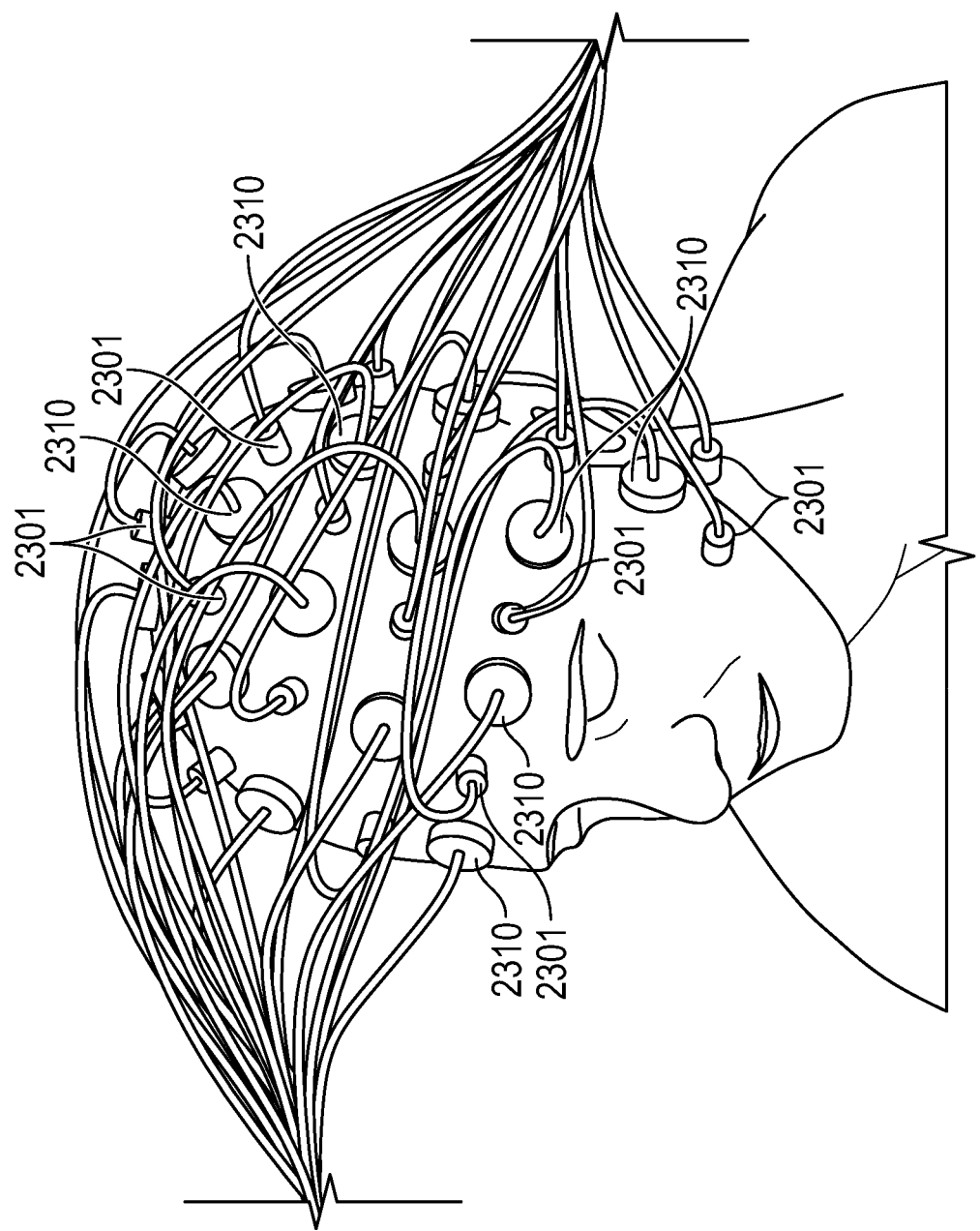
FIG. 68 shows an embodiment of a static magnetic quantitative electroencephalography system.

FIG. 68 shows a static magnetic qEEG system. The system includes typical passive of active electrodes (typical electrodes) 2301 used in qEEG systems known in the art, as well as magnetic electrodes 2310. The system may be used to ascertain how much electricity is being drawn to the magnets on the user's head. For example, the readings of the typical electrodes 2301 may be compared to the magnetic electrodes 2310. Furthermore, the system may be used to map the electricity of the user's brain in the presence of magnets 2310. This information may be used for positioning the magnets of a static magnetic therapy device to provide a maximum amount of body produced electricity in desired areas.

Example 1 (SP-Patient Mar. 1, 2019)

A 29 year old male with a malignant brain tumor was taken off chemotherapy because it was not effective at combating the tumor. The magnetic cap shown in FIGS. 8-13 was worn by the patient for three 24 hour periods over the course of 4 days. Each of the magnets was a 2 inch by ½ inch grade n45 neodymium ring mounting magnet with the north pole being the strong pole. The north poles of the magnets were directed inwards towards the patient's head and tumor therein. Accordingly, when the hat was positioned on the patient's head, the tumor resided within five compressed magnetic fields. FIG. 13 shows the interaction of the magnetic fields of the two magnets on the side and the magnet on the top of the hat. Two additional magnetic fields are provided, in addition to the field shown in FIG. 13, by the magnets on the front and back of the cap. A first series of magnetic resonance imaging (MRI) images of the patient's brain were obtained after chemotherapy was ended, which was 3 weeks prior to the beginning of the static magnetic therapy. A second series of MRI images of the patient's brain was obtained 2 days after the above discussed static magnetic therapy. The tumor had shrunk roughly 30% due to the four 24 hour static magnetic therapy sessions over the course of 4 days and was in the final stage of dying, without any other cancer therapies being administered, when comparing the first series of MRI images with the second series.

Example 2

Figure 69A:
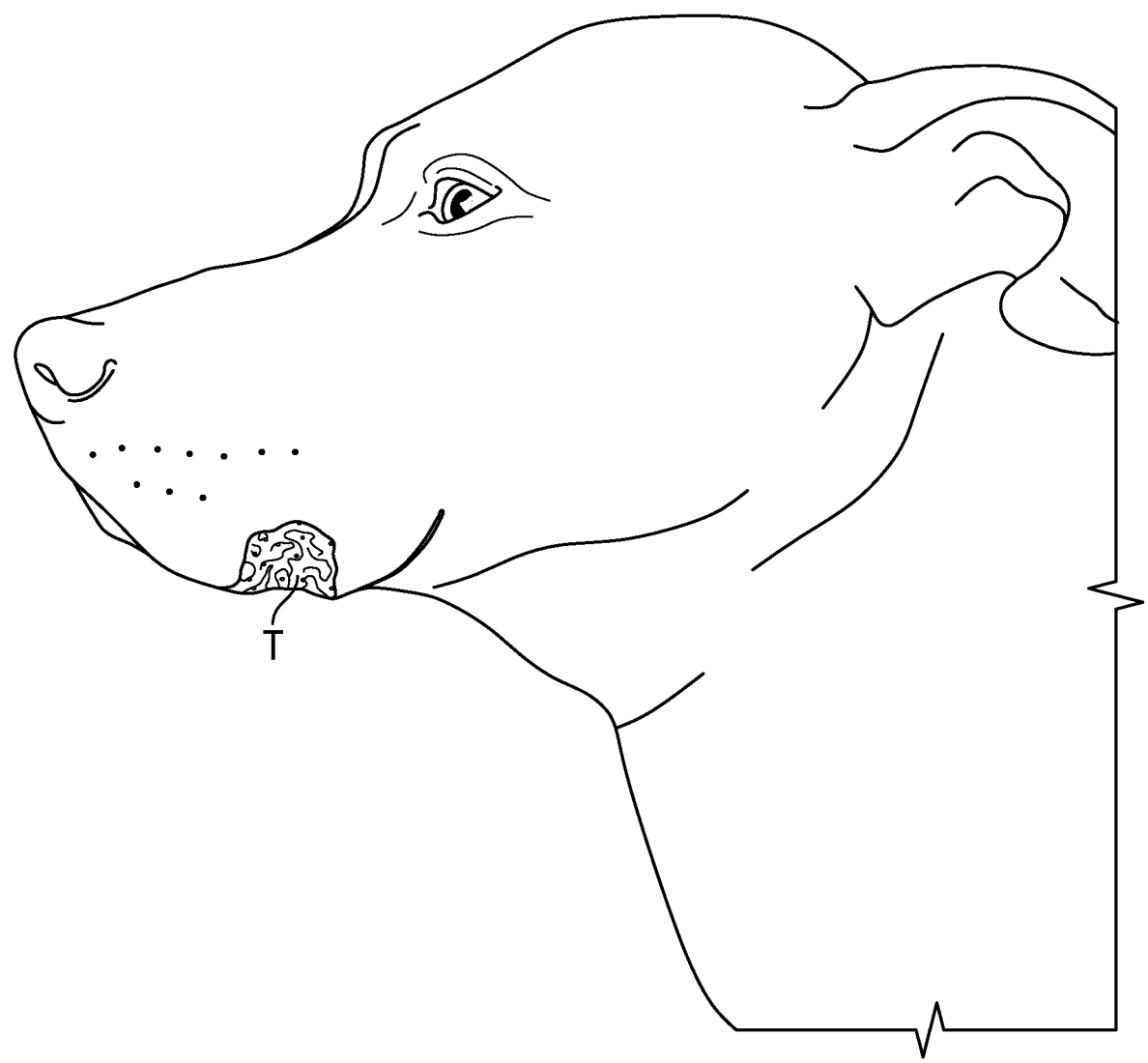
FIG. 69A is a perspective view of a dog having a mast cell tumor on it lip, prior to magnetic treatment.
Figure 69B:
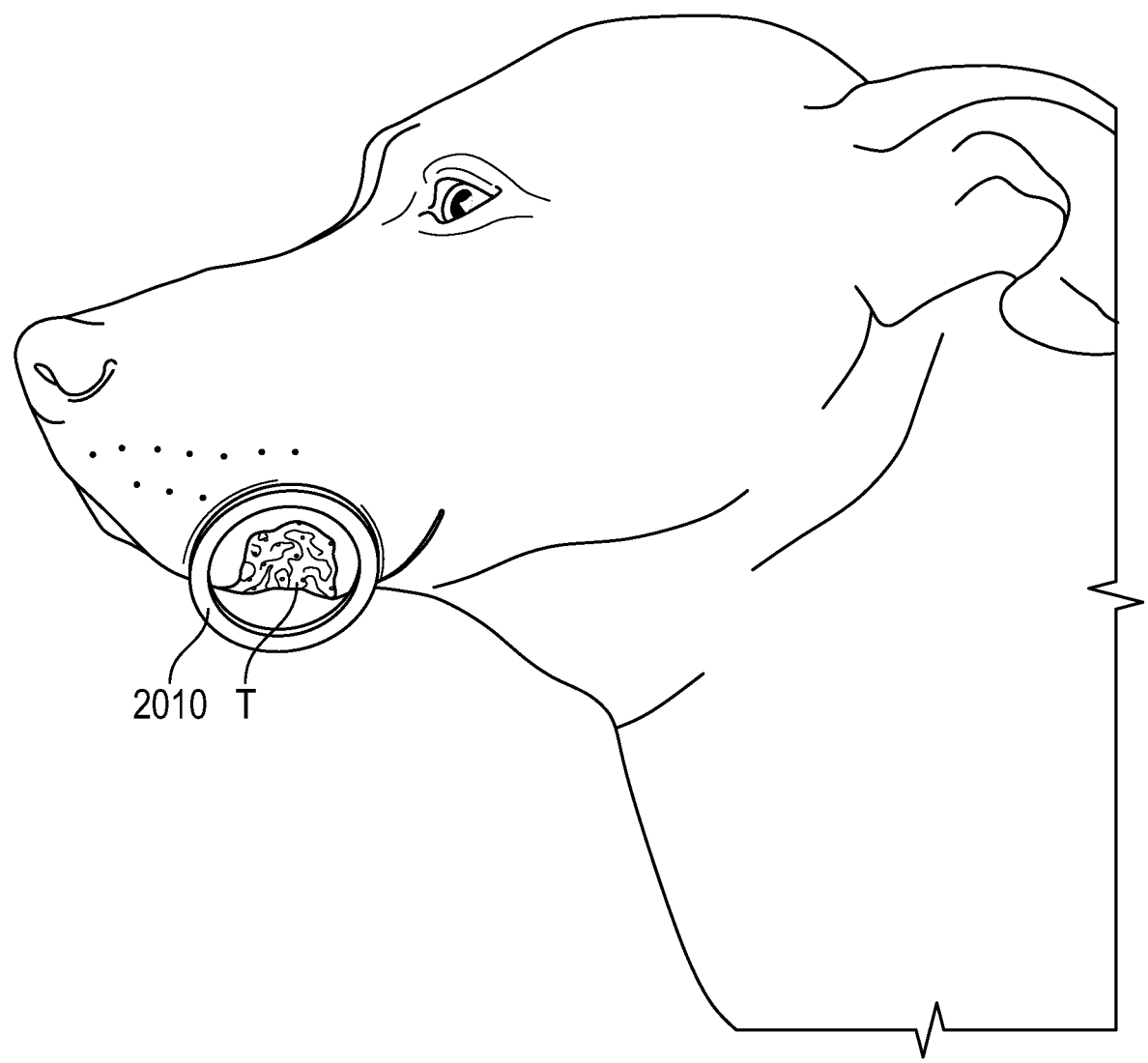
FIG. 69B is a perspective view of the dog of 69A receiving magnetic treatment on the mast cell tumor and immediately surrounding healthy tissue.
Figure 69C:
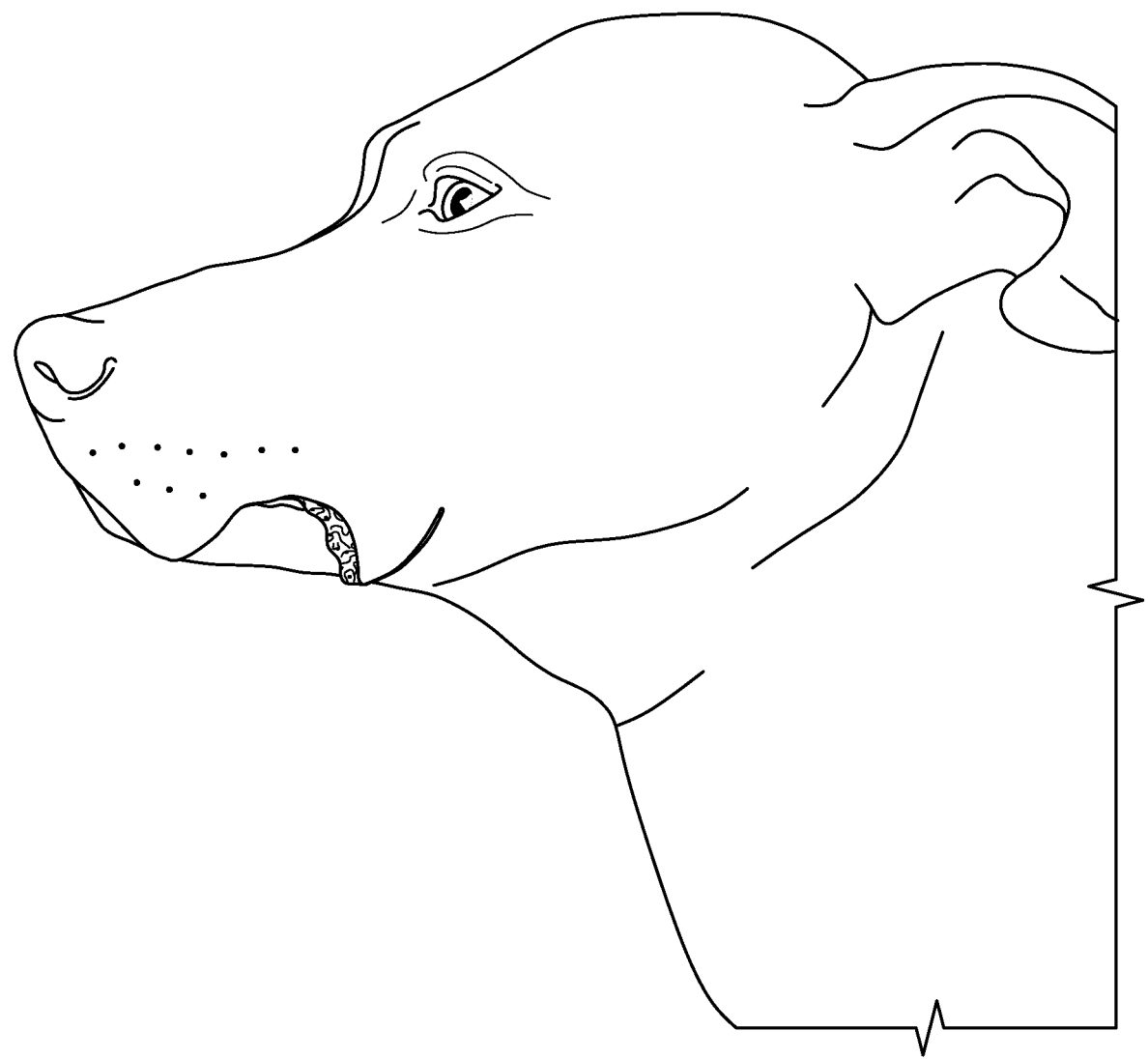
FIG. 69C is a perspective view of the dog of FIG. 69A after magnetic therapy which caused the mast cell tumor to become necrotic and fall off.
Figure 69D:
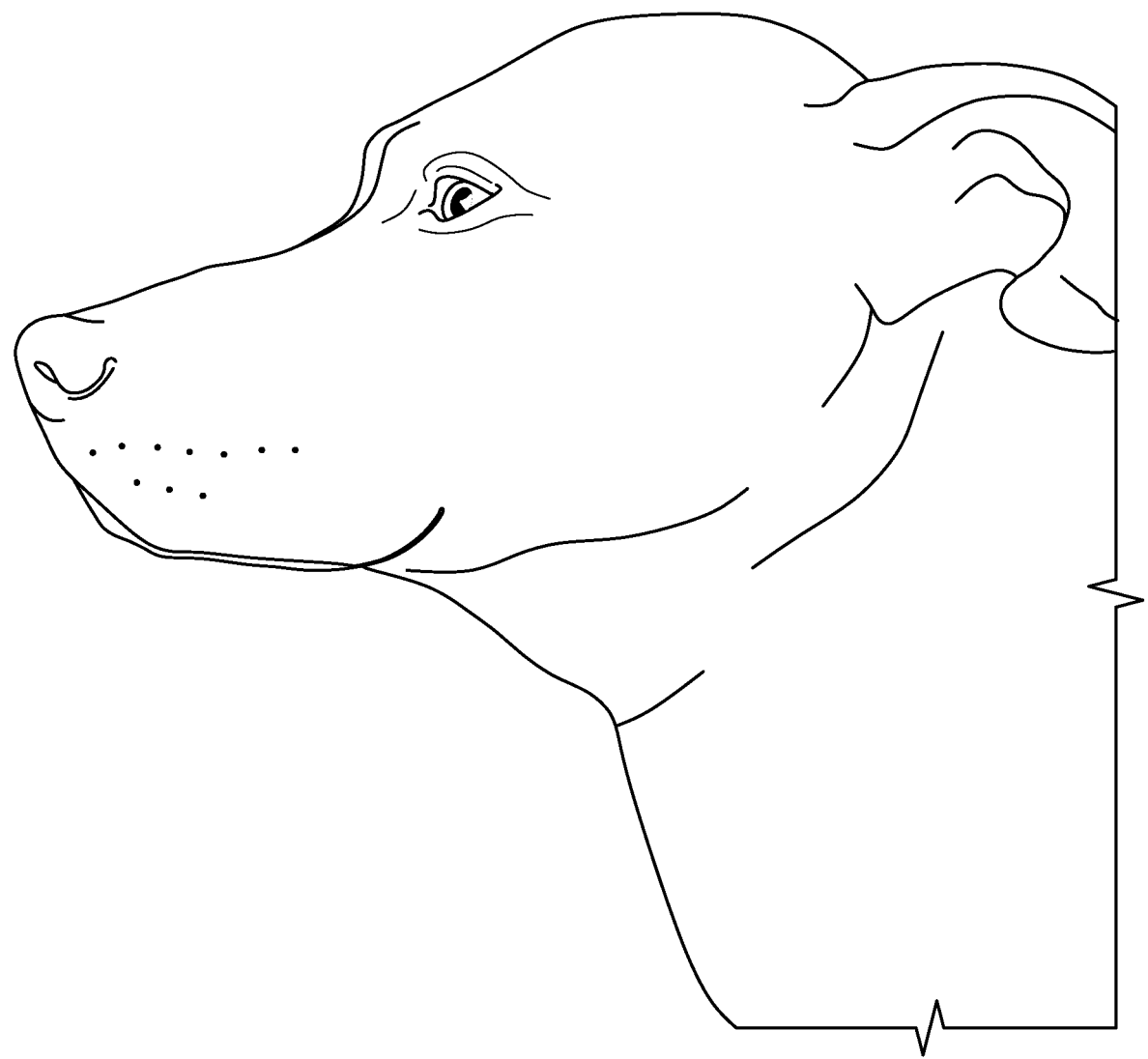
FIG. 69 D is a perspective view of the dog of FIG. 69A one month after completion of magnetic therapy, showing full lip regrowth.

FIGS. 69A-69D show the progression of magnetic therapy and full healthy tissue regrowth of an approximately 1 inch by 1 inch mast cell tumor growing in a dogs lip. A pair of annular magnets 2010 were used to treat a tumor (T) located in the lip of the dog, as shown in FIG. 69B. One magnet 2010 was placed on the outside of the lip and the other was placed on the inside of the lip. The magnets 2010 were held in place through magnetic attraction which clamped the magnets 2010 to the lip. Each annular magnet 2010 was a neodymium magnet, with a thickness of 0.095 inches, an inner diameter of 1.296 inches, and an outer diameter of 1.652 inches. At the surface (i.e., at the point of contact with the magnetometer), each annular magnet 2010 generated a magnetic field of 1.35 kG. The dog was approximately 10 years old, with a tumor which had grown over the course of approximately 10 months. After 19 continuous hours of treatment with the pair of annular magnets 2010, as described above, the tumor became necrotic and treatment with the pair of magnets was ceased. Five days after cessation of the treatment, the necrotic tumor tissue began to separate from the healthy lip tissue and flake off, as shown in FIG. 69C. The tissue at the site of treatment was quick to heal, regenerate and regrow into healthy tumor-free tissue, with regrowth and regeneration of healthy tissue being clearly evident one month after cessation of the treatment with the pair of annular magnets, as shown in FIG. 69D. During treatment, the dog did not appear to show any signs of pain, distress, blood loss, infection, or additional generation of any bodily fluids.

As described above, the method of treating tumors and causing full regrowth and regeneration of tissue may hold certain types of immune-related cells within the treatment area. The method of treating tumors and causing full regrowth and regeneration of tissue may also hold the body's stem cells within the treatment area for an extended period of time, and cause an increased influx of stem cells, effecting the observed enhanced healing, regrowth and regeneration of the tumor-free tissue. The resultant full regrowth is distinguishable from the results of surgical tumor removal. When a tumor is excised by a surgeon, the removed tissue will not grow back resulting in the fully healed lip looking similar to FIG. 69C.

Experiment 3

Figure 23:
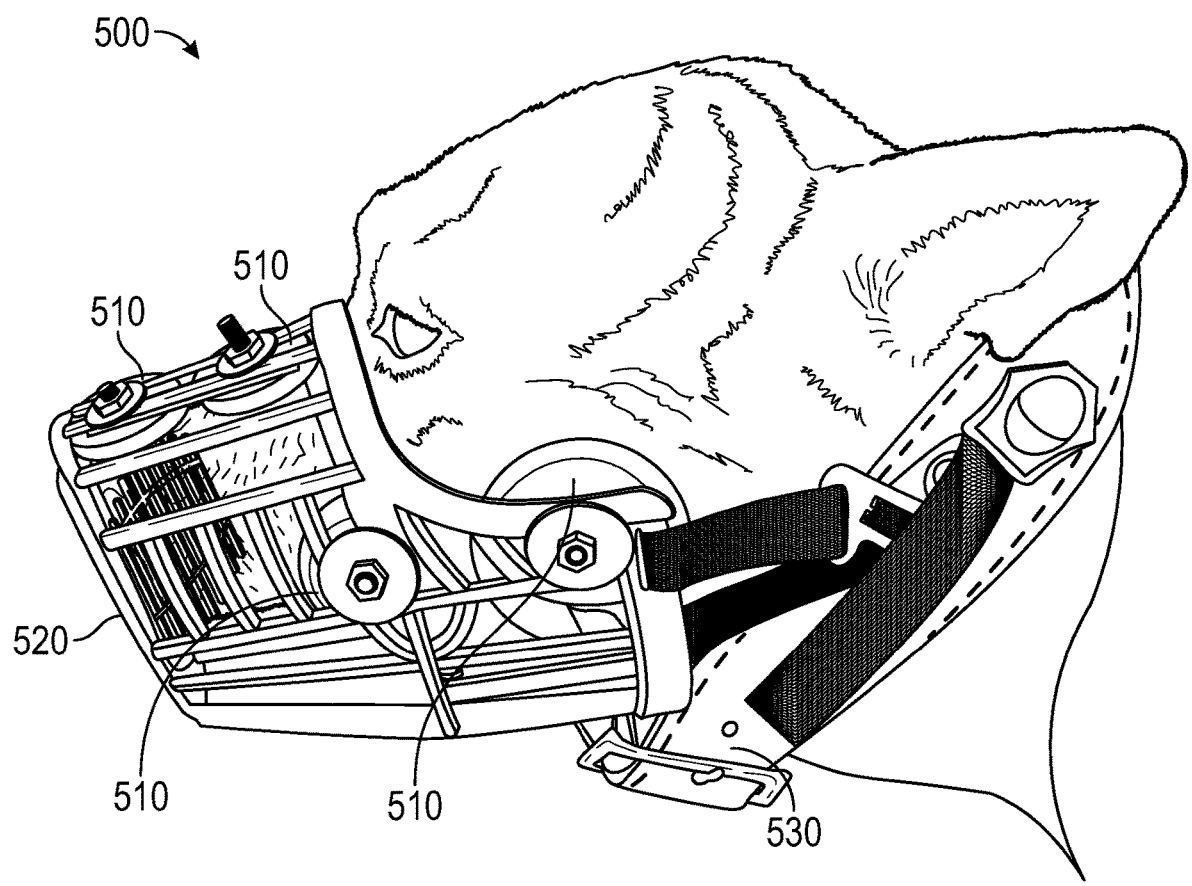
FIG. 23 is an environmental view of the magnetic therapy muzzle of FIG. 19 being worn by a dog.

The magnetic muzzle shown in FIGS. 19-23 was used to treat multiple mast cell tumors on the lips and mouth region of an approximately 10 year old dog. The tumors had grown over the course of approximately a week while the dog was being administered chemotherapy. Approximately 10 mast cell tumors between ⅙ to ⅓ of an inch in diameter were growing on the lips and mouth region of the dog. The mast cell tumors were rapidly growing and new tumors were developing despite the chemotherapy treatment. The magnetic muzzle was attached to the dog for a period of 24 hours, with small breaks to allow for eating and drinking. The muzzle included two front magnets which were 1⅝ inch grade 45 neodymium ring magnets and two rear magnets which were 2 inch grade 45 neodymium ring mounting magnets having the north poles as the strong poles. The north poles of the magnets were facing inwards, towards the magnets on the opposing side of the muzzle, to create compressed magnetic fields around the mouth of the dog, thus exposing the tumors to compressed magnetic fields. The muzzle was positioned as shown in FIG. 23. When the muzzle was removed after 24 hours, the cells of each tumor became neurotic, scabbed over, and flaked off within 2 days. The location of each tumor experienced full regrowth of healthy tissue thus indicating an increased presence of stem cells.

Experiment 4

Magnetic therapy was used to treat three malignant tumors in the neck of an approximately 10 year old dog. The tumors had grown over the course of approximately two weeks while the dog was being administered chemotherapy. The tumors had diameters in the range of ½ of an inch to 1 inch. The magnetic collar shown in FIGS. 45 and 46 was secured around the dog's neck adjacent the tumor locations. The magnetic collar contained four 4 inch by ⅝ inch grade 45 neodymium ring magnets positioned on opposing sides of the dogs neck and a 3 inch by 1.2 inch grade 45 neodymium ring magnet positioned below the neck, as seen in FIG. 46. The north poles of the mounting magnets were each directed towards the neck of the dog resulting in the tumors residing within five compressed north pole magnetic fields. The magnetic collar was loosely secured to the neck of the dog. The loose fit resulted in the location of the magnets constantly being shifted along the length of the neck and rotating around the neck with the movement of the dog. The shifting of the collar, and attached magnets, provided expanded coverage of the strongest portions of the compressed magnetic fields throughout the neck. The magnetic collar was secured to the dog for two periods of four hours each day for 7 days. After 7 days, each of the tumors ruptured and the necrotic cells drained out. Each location experienced natural regrowth without additional medical intervention indicating increased stem cell presence.

Experiment 5

Figure 70:
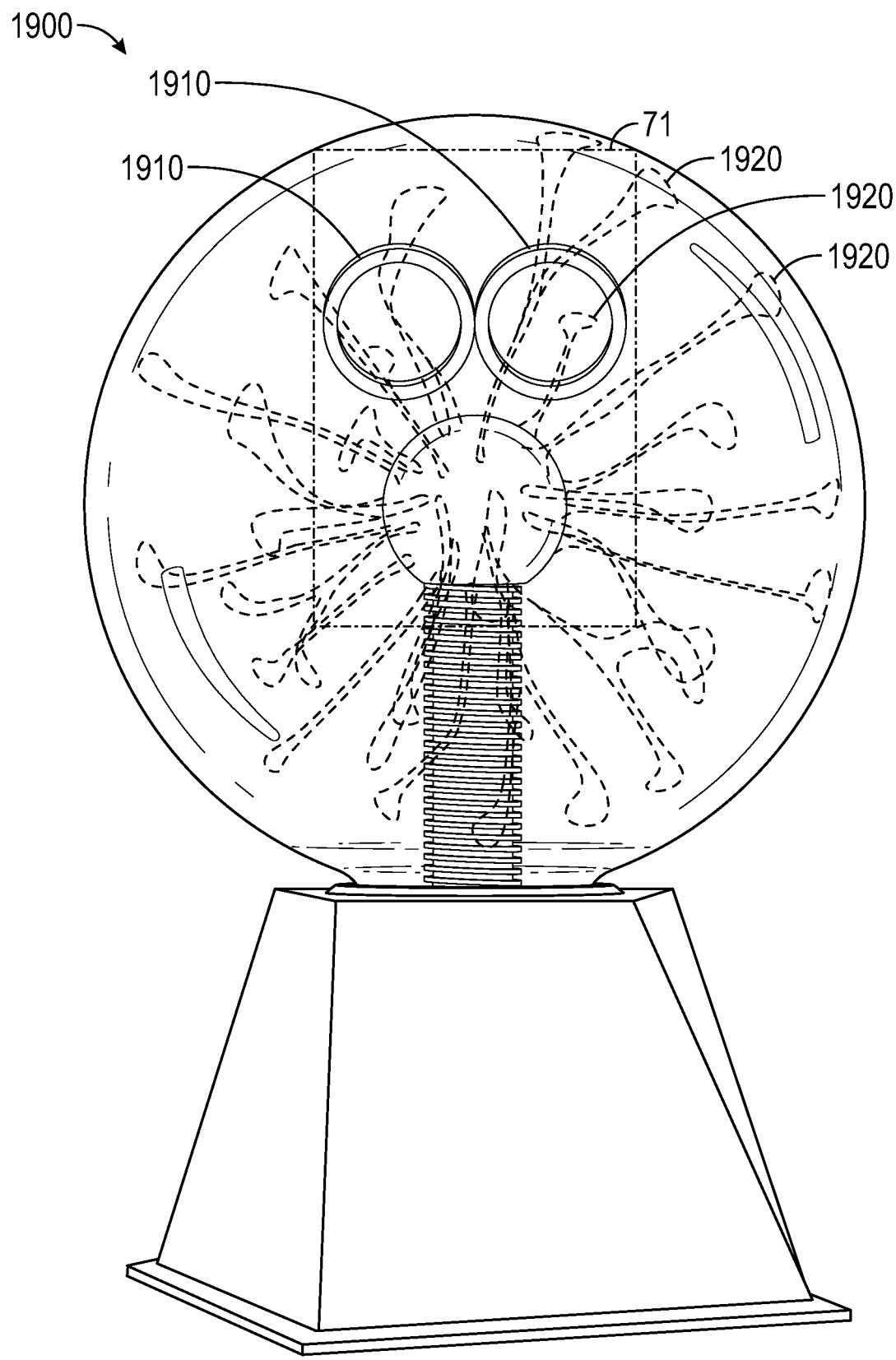
FIG. 70 is a perspective view of a plasma globe with two attached ring magnets.
Figure 71:
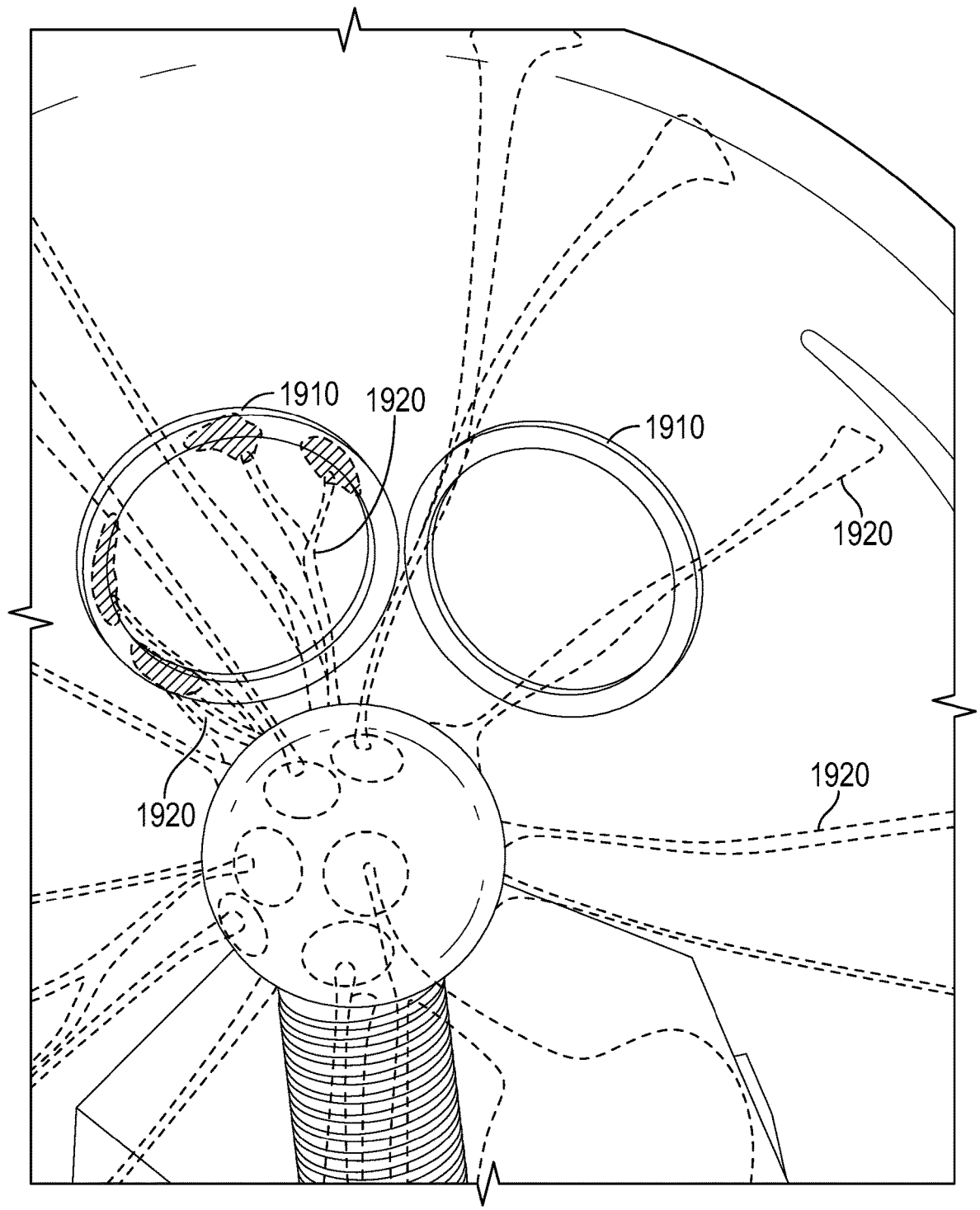
FIG. 71 is a zoomed in view of the plasma globe and attached magnets of FIG. 70 based on box 71.
Figure 72:
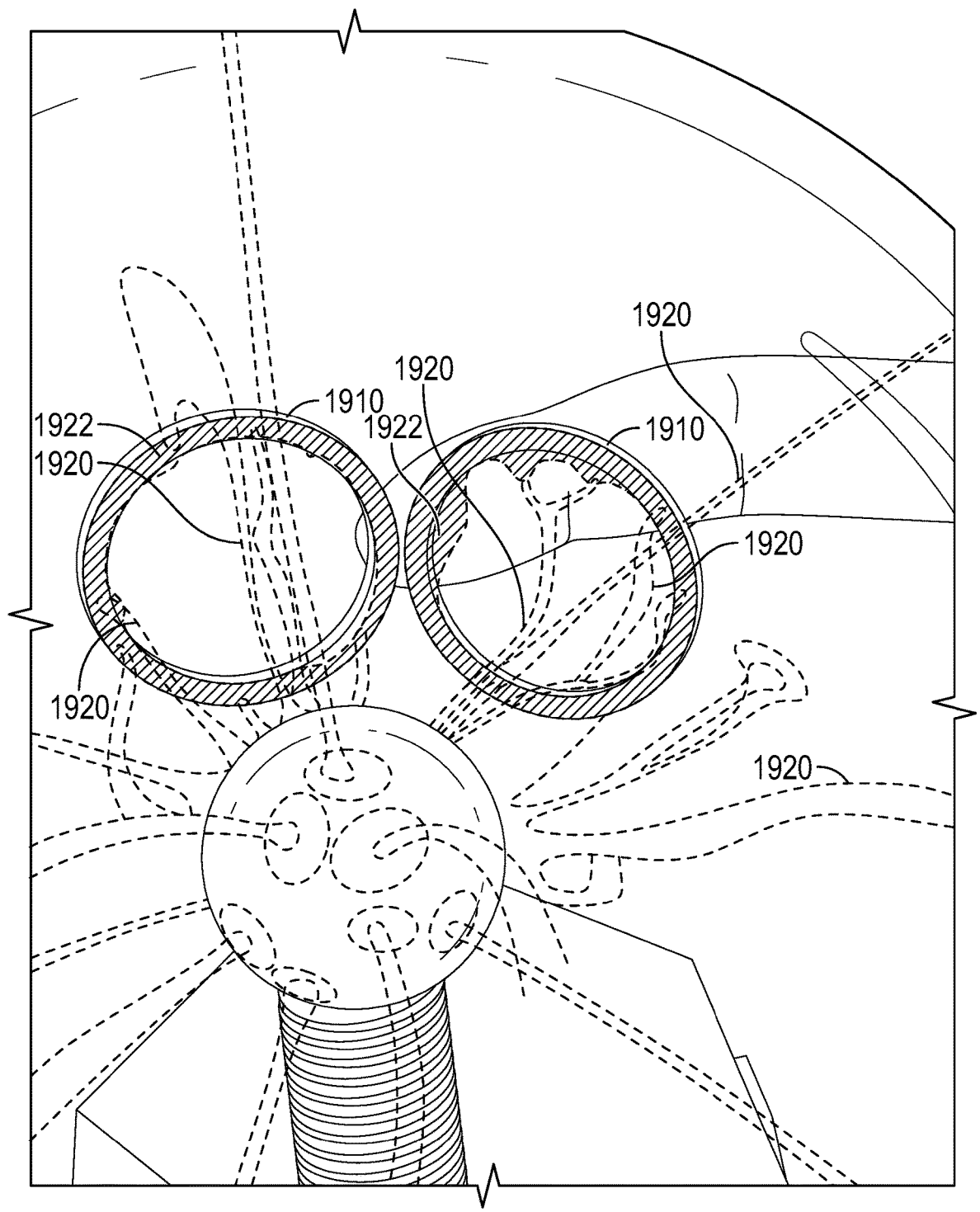
FIG. 72 is a perspective view of the plasma globe and attached magnets of FIG. 70 when a user is touching the magnets.
Figure 73:
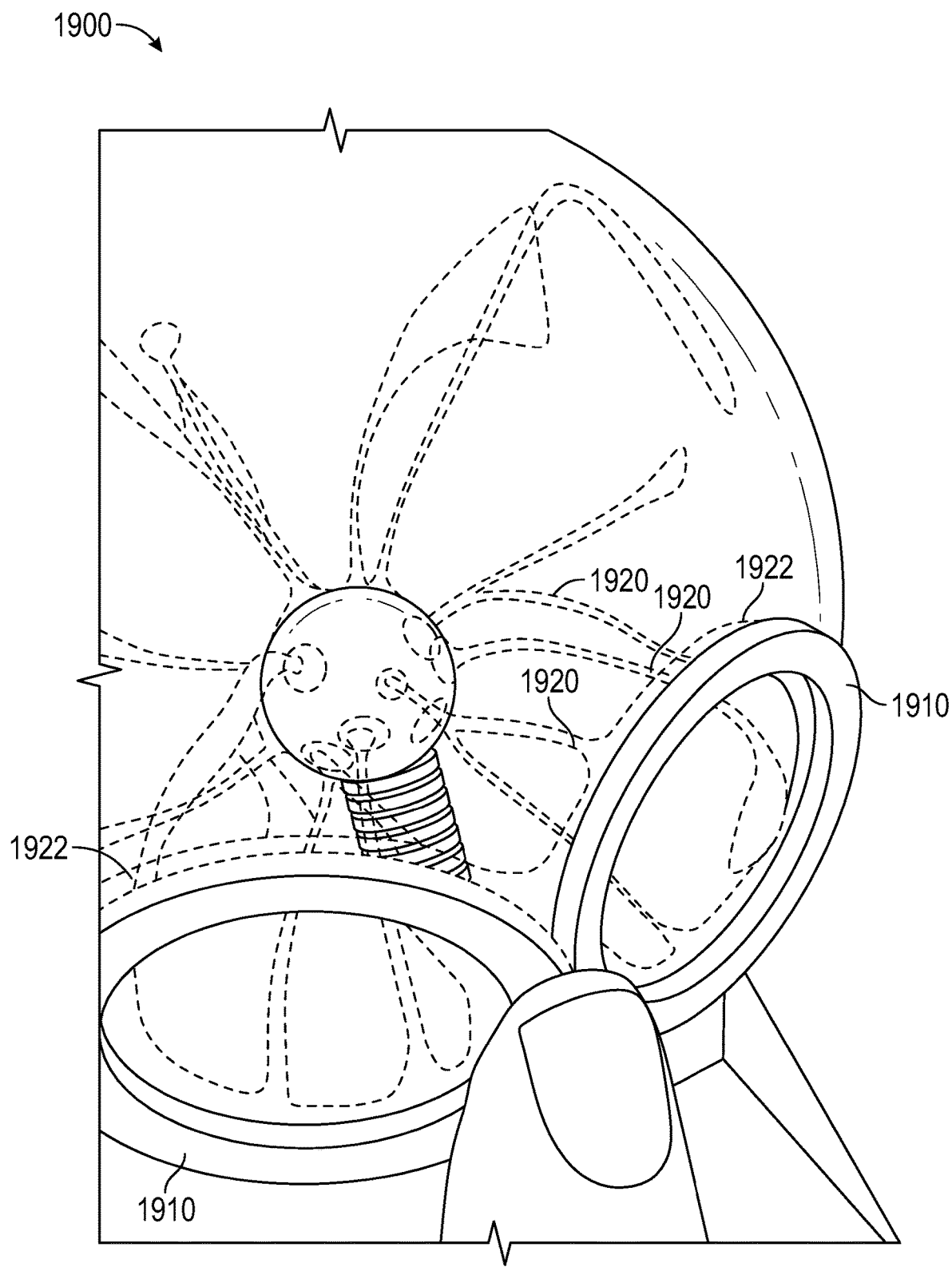
FIG. 73 is a perspective view of the plasma globe and attached magnets of FIG. 70 for the user's point of view.
Figure 74:
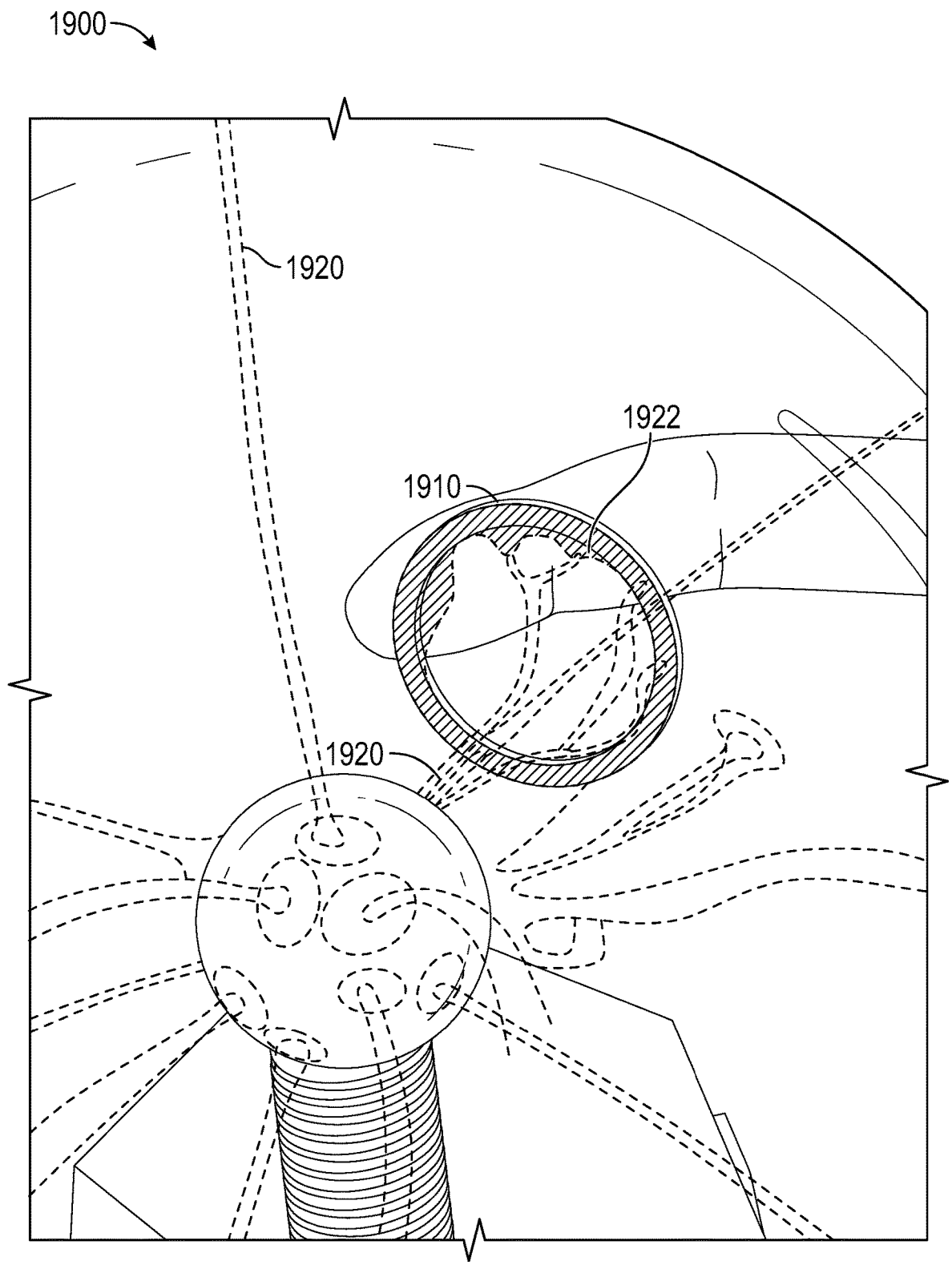
FIG. 74 is a perspective view of the plasma globe and an attached ring magnet when a user is toughing the magnet.

The effect of electricity with regard to ring magnets was tested using a plasma globe 1900. FIGS. 70 and 71 shown two ring magnets 1910 attached to a plasma globe 1900. The two magnets 1910 we taped to the globe with the north poles facing inwards. As seen in FIG. 70, plasma filaments 1920 are directed to the magnets. FIGS. 72 and 73 show the ring magnets 1910 when being held in place by a user's hand. When held in place by the hand of a user, a larger amount of plasma filaments 1920 are directed to the magnets 1910 resulting in plasma ring 1922 forming around the entire circumference of each magnet 1910. FIG. 74 shows a single magnet 1910 attracting enough plasma filaments 1920 to create a plasma ring 1922 around the globe 1900 facing side of the magnet 1910, similar to the two magnets 1910 shown in FIGS. 70 and 71.

Figure 75:
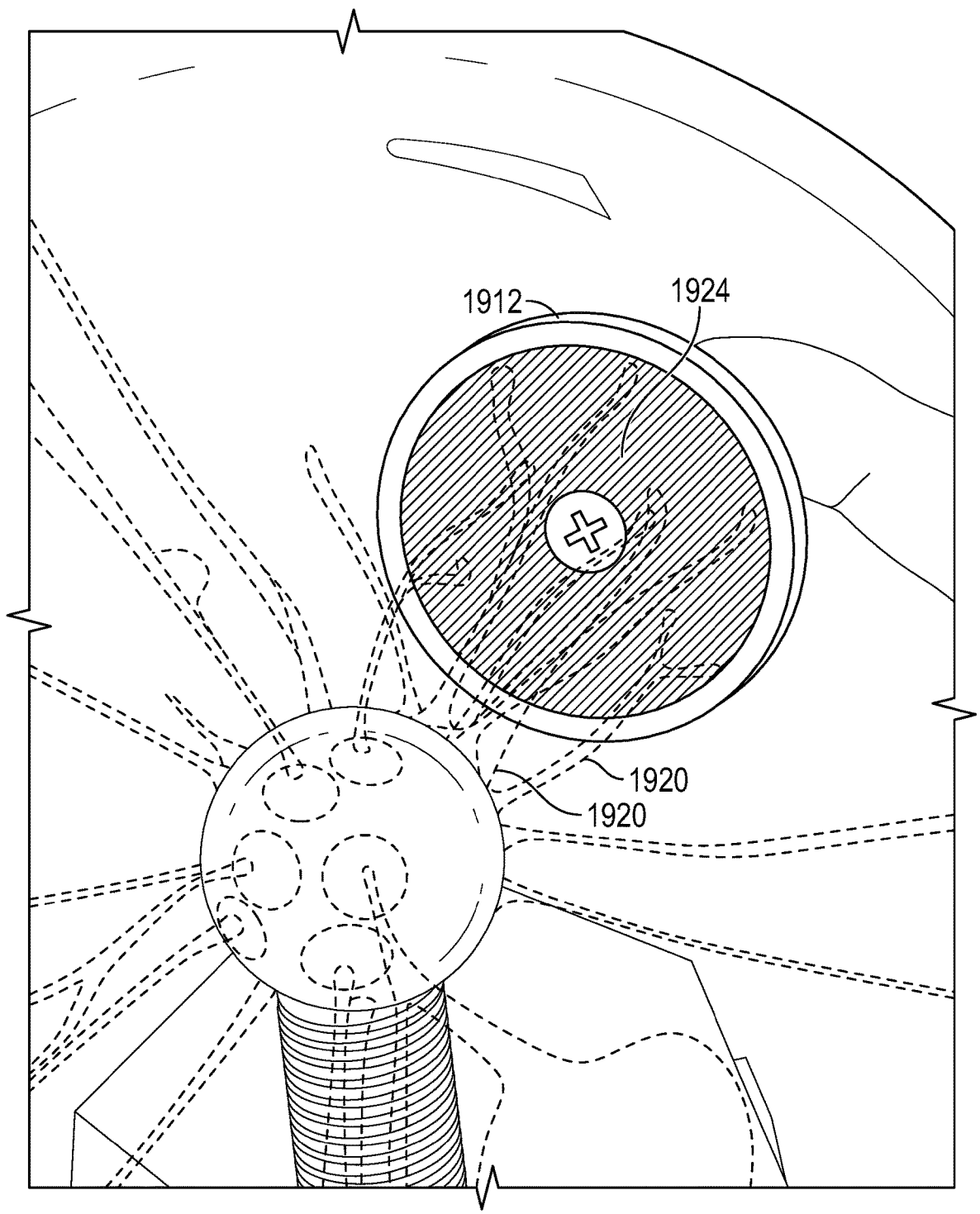
FIG. 75 is a perspective view of the plasma globe and an attached mounting magnet.

FIG. 75 shows a mounting magnet 1912 placed on the globe 1900 with the north pole facing inwards. Only the central magnetic portion of the mounting magnet was contacting the globe, the outer shell, which is separated from the magnetic portion by an insulating polymer, was not touching the globe. The mounting magnet attracted more plasma filaments 1920 than the ring magnets 1910, resulting in a large plasma donut 1924 forming below the magnet 1912. A concentration of the plasma filaments were directed at the central opening of the mounting magnet indicating the electricity was being pulled through the central opening by the magnetic field. To confirm that the magnetic field was pulling electricity through the central opening of the magnetic, a voltmeter used to read the voltage present on the outer shell of the mounting magnet (which was not contacting the globe and was separated from the magnetic portion by an insulating polymer). The voltmeter indicated the voltage of the shell was fluctuating between 0.07 and 0.13 mV, thus indicating the electricity was being carried to the shell by the magnetic field.

Each of the experiments was also performed with the south pole of the magnets 1910, 1912 facing towards the globe 1900 and resulted in the similar plasma attraction.

Experiment 6

The effect of magnets on the electricity produced by the body was tested by placing a grade 45 neodymium housing magnet having a 3 inch diameter and a ⅝ inch thickness on different portions of a patient's head and determining the effect on the EEG readings. The EEG electrodes were attached to the patient's head using the 10-20 system which is well known in the art. The 10-20 system uses 19 electrodes with the location of the electrode indicated by letters based on the brain region or lobes (Fp=fronto-polar; F=frontal; C=central; P=parietal; O=occipital; T=temporal) flowed by a number or letter indicating the distance to the midline (numbers range from 1-6 with large numbers indicate greater distance to the midline, odd numbers indicating left hemisphere and even numbers indicating right hemisphere; the letter "z" indicated on the midline). When the magnet was placed in between electrodes, the readout of the electrodes surrounding the magnet would produce very large inconsistent waves indicating the electrical signal to the electrode would fell below the detectable levels of the EEG machine. For example, when the patient was connected to each electrode and the machine recorded the electrical signals of the patient's head, each electrode detected a recordable signal resulting in a consistent, readable wave being produced for each electrode. When the magnet was placed on the left rear quadrant of the head, each of electrodes T3, C3, P3, O1, and T5, which are located in the rear left quadrant of the head, were exposed to electrical signals too small for the EEG machine to detect resulting in the large unreadable waves. This indicated the electricity is the brain was being pulled to the magnet and away from the electrodes.

Experiment 7

A strength of a magnetic field produced by a 2 inch by ½ inch grade n45 neodymium ring mounting magnet was measured using a gaussmeter placed on the face of the strong pole. The gaussmeter measured 2.03 kilogauss (kG). A subject them completely covered the magnet with his hand and measured the strength of the magnetic field that had traveled through his hand. The magnetic field was measured at 0.02 kG, thus indicating the magnetic field retain significant strength through approximately 1 inch of tissue.

A strength of a magnetic field produced by a 3 inch by ¾ inch grade n45 neodymium ring mounting magnet was measured using a gaussmeter placed on the face of the strong pole. The gaussmeter measured 2.05 kG. A subject then placed the gaussmeter on a side of his calf, with no magnet near the calf, which resulted in a reading of 0.0 Gauss. The subject then placed the magnet on the side of his calf opposite the gaussmeter, with the circumference of the magnet being completely covered. The strength of the magnetic field was then measure, resulting in a strength of 0.1 Gauss on the opposing side of the calf from the magnet. A width of the calf was measured to be approximately 6 inches. The reading of 0.1 Gauss indicates the magnetic field retains significant strength through approximately 6 inches of tissue.

Example 8

An embodiment of a static magnet capable of producing a strong static magnetic field through a human body, or a body of other living animals, was created and the static magnetic field was measured. Table 1 shows the strength of the static magnetic field on the strong surface of the magnet at the points shown in FIG. 76A.

TABLE 1

| Location on Magnet | Magnetic field strength (kilogauss "kG") |
|---|---|
| Z1 | 5.37 |
| Z2 | 6.39 |
| Z3 | 5.79 |
| Z4 | 5.71 |
| Z5 | 5.16 |
| Z6 | 5.28 |
| Z7 | 5.01 |
| Z8 | 4.90 |
| Z9 | −5.24 |
| Z10 | −9.11 |
| Z11 | −5.11 |
| Z12 | −5.4 |
| Z13 | −8.58 |
| Z14 | −5.44 |
| Z15 | −5.13 |
| Z16 | −8.73 |
| Z17 | −5.30 |
| Z18 | −5.52 |

TABLE 1-continued

| Location on Magnet | Magnetic field strength (kilogauss "kG") |
|---|---|
| Z19 | −8.89 |
| Z20 | −5.10 |

Figure 76A:
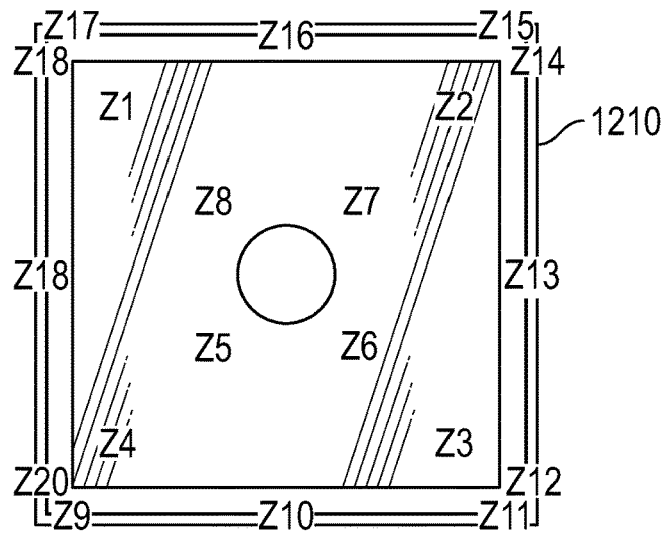
FIG. 76A shows a strong side of an embodiment of a magnet.

Table 2 shows the strength of the static magnetic field extending out from the strong surface of the magnet, with air as the medium, at the points shown in FIG. 76A, as well as the center.

TABLE 2

|  | Center | Point Z1 | Point Z2 | Point Z3 | Point Z4 |
|---|---|---|---|---|---|
| 1" from surface | 2.14 kG | 2.03 kG | 2.33 kG | 2.40 kG | 2.17 kG |
| 2" from surface | 1.51 kG | 1.06 kG | 1.06 kG | 1.19 kG | 1.13 kG |
| 3" from surface | 0.91 kG | 0.62 kG | 0.62 kG | 0.68 kG | 0.67 kG |
| 4" from surface | 0.56 kG | 0.40 kG | 0.40 kG | 0.43 kG | 0.44 kG |
| 5" from surface | 0.35 kG | 0.28 kG | 0.28 kG | 0.29 kG | 0.29 kG |
| 6" from surface | 0.24 kG | 0.18 kG | 0.18 kG | 0.20 kG | 0.20 kG |
| 7" from surface | 0.16 kG | 0.13 kG | 0.13 kG | 0.14 kG | 0.15 kG |
| 8" from surface | 0.12 kG | 0.10 kG | 0.10 kG | 0.10 kG | 0.11 kG |
| 9" from surface | 0.09 kG | 0.07 kG | 0.07 kG | 0.08 kG | 0.08 kG |
| 10" from surface | 0.07 kG | 0.06 kG | 0.06 kG | 0.06 kG | 0.06 kG |

Figure 76B:
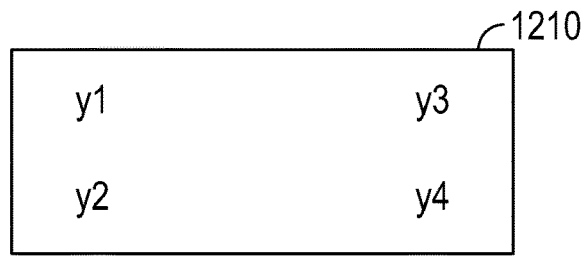
FIG. 76B shows a peripheral side of the magnet of FIG. 76A.

Table 3 shows the strength of the magnetic field on the side surface of the magnet 1210 (on the surface of the metal shield) at the points shown in FIG. 76B.

TABLE 3

| Location on side of magnet | Strength (Kg) |
|---|---|
| Y1 | 1.00 |
| Y2 | −3.60 |
| Y3 | 1.02 |
| Y4 | −3.21 |

Figure 76C:
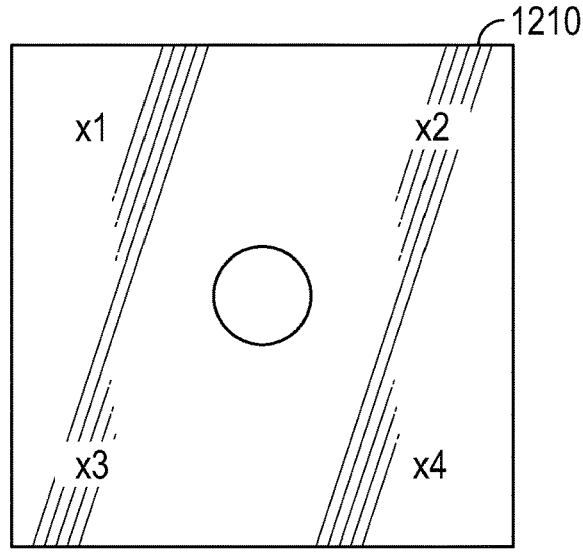
FIG. 76C shows the weak side of the magnet of FIG. 76A.

Table 4 shows the strength of the magnetic field on the weak surface of the magnet 1210 (on the surface of the metal shield) at the points shown in FIG. 76C.

TABLE 4

| Location on side of magnet | Strength (Kg) |
|---|---|
| X1 | 1.24 |
| X2 | 1.31 |
| X3 | 1.34 |
| X4 | 1.33 |

It is to be understood that the devices and methods for stimulating the immune system to treat abnormal and damaged tissue using compressed magnetic fields is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

What is claimed is:

1. A device for treating a patient for damaged or abnormal tissue and causing full regrowth and regeneration of tissue comprising:
    a first static mounting magnet;
    a second static mounting magnet;
    a first securing strip configured to secure the first static mounting magnet and the second static mounting magnet to sandwich the patient's head or neck and to form a first compressed static magnetic field;
    a third static mounting magnet;
    a fourth static mounting magnet;
    a second securing strip configured to secure the third static mounting magnet and the fourth static mounting magnet to sandwich the patient's jaw and to form a second compressed static magnetic field; and
    a collar, wherein the first securing strip and the second securing strip are attached to the collar.

2. The device as claimed in claim 1, further comprising:
    a fifth static mounting magnet; and
    a sixth static mounting magnet;
    wherein the fifth static mounting magnet and the sixth static mounting magnet are secured by the second securing strip to form a third compressed static magnetic field.

3. The device as claimed in claim 1, further comprising:
    a muzzle cage attached to the second securing strip.

* * * * *